(12) United States Patent
Quan et al.

(10) Patent No.: US 7,709,646 B2
(45) Date of Patent: May 4, 2010

(54) TETRAHYDROQUINOLINE DERIVATIVES USEFUL AS SERINE PROTEASE INHIBITORS

(75) Inventors: Mimi L. Quan, Yardley, PA (US); Cailan Wang, New Hope, PA (US); Jinglan Zhou, San Diego, CA (US); Jon J. Hangeland, Morrisville, PA (US); Dietmar A. Seiffert, Boothwyn, PA (US); Robert M. Knabb, Avondale, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 991 days.

(21) Appl. No.: 11/430,588

(22) Filed: May 9, 2006

(65) Prior Publication Data

US 2006/0223854 A1 Oct. 5, 2006

Related U.S. Application Data

(62) Division of application No. 10/796,396, filed on Mar. 9, 2004, now Pat. No. 7,138,412.

(60) Provisional application No. 60/453,812, filed on Mar. 11, 2003.

(51) Int. Cl.
*C07D 215/38* (2006.01)
(52) U.S. Cl. ...................... 546/159; 514/312
(58) Field of Classification Search ................. 546/159; 514/312
See application file for complete search history.

(56) References Cited

U.S. PATENT DOCUMENTS

| 6,262,269 | B1 * | 7/2001 | Hayes et al. | 546/159 |
| 6,388,081 | B1 * | 5/2002 | Hayes et al. | 506/15 |
| 6,605,615 | B2 | 8/2003 | Medina et al. | |
| 7,138,412 | B2 * | 11/2006 | Quan et al. | 514/311 |
| 2004/0220206 | A1 | 4/2004 | Smallheer et al. | |
| 2006/0183771 | A1 | 8/2006 | Seiffert et al. | |

FOREIGN PATENT DOCUMENTS

| EP | 0379145 A | 7/1990 |
| FR | 1605038 | 8/1972 |
| WO | WO98/34115 A1 | 8/1998 |
| WO | WO99/12935 A1 | 3/1999 |
| WO | WO01/02356 A1 | 1/2001 |
| WO | WO01/27079 A2 | 4/2001 |
| WO | WO02/42273 A2 | 5/2002 |
| WO | WO2004/094372 | 11/2004 |

OTHER PUBLICATIONS

Kubitza, Exp Opin Investig Drugs,2006, pp. 843-855.*
Buu-Hoi et al., "Friedel Crafts Acylations of 3-Clhoro-4-methoxybiphenyl", contribution from the Department of Organic Chemistry, Radium Institute, University of Paris, Dec. 26, 1956, vol. 22, pp. 668-671.
Bouma, B.N. et al., Thrombin-Activatable Fibrinolysis Inhibitor (TAFI, Plasma Procarboxypeptidase B, Procarboxypeptidase R, Procarbopeptidase U), Thrombosis Research, vol. 101, pp. 329-354 (2001).
Colman, R.W., Chapter 6: "Contact Activation Pathway: Inflammatory, Fibrinolytic, Anticoagulant, Antiadhesive, and Antiangiogenic Activities", Hemostasis and Thrombosis: Basic Principles and Clinical Practice, Fourth Edition, Lippincott Williams & Wilkins, publ. pp. 103-121 (2001).
Gailani, D., "Activation of Factor 1X by Factor Xia", Trends Cardiovasc. Med., vol. 10, No. 5, pp. 198-204 (2000).
Gailani, D., "Gene Targeting in Hemostasis, Factor XI", Frontiers in Bioscience, vol. 6, pp. d201-d207 (2001).
Gailani, D., et al., "A murine model of factor XI deficiency", Blood Coagulation and Fibinolysis, vol. 8, pp. 134-144 (1997).
Meijers, J.C.M., et al., "High Levels of Coagulation Factor XI as a Risk Factor for Venous Thrombosis", The New England Journal of Medicine, vol. 342, No. 10, pp. 696-701 (2000).
Minnema, M.C. et al., "Activation of Clotting Factors XI and IX in Patients with Acute Myocardial Infarction", Arterioscler. Thromb. Vasc, Biol., vol. 20, pp. 2489-2493 (2000).
Murakami, T., et al., "Evaluation of Factor XIa-$\alpha_1$-Antitrypsin in Plasma, a Contract Phase-Activated Coagulation Factor-Inhibitor Complex, in Patients with Coronary Artery Disease", Arterioscler, Thromb. Vasc. Biol., vol. 15, No. 8, pp. 1107-1113 (1995).

(Continued)

*Primary Examiner*—D. Margaret Seaman
(74) *Attorney, Agent, or Firm*—Jing G. Sun

(57) ABSTRACT

The present invention provides compounds of Formula (I):

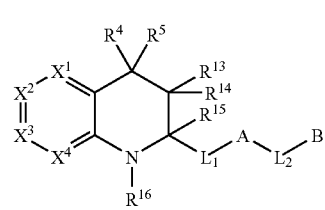

or a stereoisomer or pharmaceutically acceptable salt form thereof, wherein the variables A, B, $L_1$, $L_2$, $X^1$, $X^2$, $X^3$, $X^4$, $R^4$, $R^5$, $R^{13}$, $R^{14}$, $R^{15}$ and $R^{16}$ are as defined herein. The compounds of Formula (I) are useful as selective inhibitors of serine protease enzymes of the coagulation cascade and/or contact activation system; for example thrombin, factor Xa, factor XIa, factor IXa, factor VIIa and/or plasma kallikrein. In particular, it relates to compounds that are selective factor XIa inhibitors. This invention also relates to pharmaceutical compositions comprising these compounds and methods of treating thromboembolic and/or inflammatory disorders using the same.

8 Claims, No Drawings

OTHER PUBLICATIONS

Schmaier, A.H., Chapter 5: "Contact Activation", Thrombosis and Hemorrhage, Williams & Wilkins, publ., Loscaizo, J. et al., eds., pp. 105-127 (1998).

Walsh, P.N., "Platelets and Factor XI Bypass the Contact System of Blood Coagulation", Thrombosis and Haemostasis, vol. 82, No. 2, pp. 234-242 (1999).

* cited by examiner

TETRAHYDROQUINOLINE DERIVATIVES USEFUL AS SERINE PROTEASE INHIBITORS

CROSS-REFERENCE TO RELATED APPLICATIONS

This application is a divisional of U.S. application Ser. No. 10/796,396, filed Mar. 9, 2004, now U.S. Pat. No. 7,138,412 now allowed, which claims priority of U.S. Provisional Application Ser. No. 60/453,812, filed Mar. 11, 2003. The entire disclosure of each of the foregoing applications is herein incorporated by reference in its entirety.

FIELD OF THE INVENTION

The present invention relates generally to compounds that inhibit serine proteases. In particular it is directed to novel 1,2,3,4-tetrahydroquinoline compounds of formula (I):

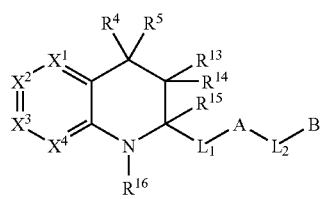

or a stereoisomer or pharmaceutically acceptable salt form thereof, which are useful as selective inhibitors of serine protease enzymes of the coagulation cascade and/or contact activation system; for example thrombin, factor XIa, factor Xa, factor IXa, factor VIIa, and/or plasma kallikrein. In particular, it relates to compounds that are selective factor XIa inhibitors. This invention also relates to pharmaceutical compositions comprising these compounds and methods of using the same.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood coagulation is initiated in vivo by the binding of tissue factor (TF) to Factor VII (FVII) to generate Factor VIIa (FVIIa). The resulting TF:FVIIa complex activates Factor IX (FIX) and Factor X (FX) which leads to the production of Factor Xa (FXa). The FXa that is generated catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N. *Thromb. Haemostasis*. 1999, 82, 234-242.) Factor XIa plays a key role in propagating this amplification loop and is thus an attractive target for anti-thrombotic therapy.

An alternative way of initiation of coagulation is operative when blood is exposed to artificial surfaces (e.g., during hemodialysis, 'on-pump' cardiovascular surgery, vessel grafts, bacterial sepsis). This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D. *Trends Cardiovasc. Med.* 2000, 10, 198-204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al. *Thromb. Res.* 2001, 101, 329-354.) Thus, inhibitors of factor XIa are expected to be anticoagulant and profibrinolytic.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of APTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The APTT (intrinsic system) is prolonged in a gene dose-dependent fashion. Interestingly, even after severe stimulation of the coagulation system (tail transaction), the bleeding time is not significantly prolonged compared to wild-type and heterozygous litter mates. (Gailani, D. *Frontiers in Bioscience* 2001, 6, 201-207; Gailani, D. et al. *Blood Coagulation and Fibrinolysis* 1997, 8, 134-144.) Taken together, these observations suggest that high levels of inhibition of factor XIa should be well tolerated. This is in contrast to gene targeting experiments with other coagulation factors.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al. *Arterioscler. Thromb. Vasc. Biol.* 2000, 20, 2489-2493). A second study establishes a positive correlation between the extent of coronary arteriosclerosis and factor XIa in complex with alpha 1 antitrypsin (Murakami, T. et al. *Arterioscler Thromb Vasc Biol* 1995, 15, 1107-1113.). In another study, Factor XI levels above the 90$^{th}$ percentile in patients were associated with a 2.2-fold increased risk for venous thrombosis (Meijers, J. C. M. et al. *N. Engl. J. Med.* 2000, 342, 696-701.).

Plasma kallikrein is a zymogen of a trypsin-like serine protease and is present in plasma at 35 to 50 μg/mL. The gene structure is similar to that of factor XI, overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Proteins or peptides that reportedly inhibit Factor XIa are disclosed in WO 01/27079. There are advantages in using small organic compounds, however, in preparing pharmaceuticals, e.g., small compounds generally have better oral bioavailability and compatibility in making formulations to aid in delivery of the drug as compared with large proteins or peptides. Small molecule inhibitors of Factor XIa are disclosed in WO 99/12935 and WO02/42273.

In addition to the above, WO 01/02356 describes 2-aryl substituted tetrahydroquinoline compounds as inhibitors of Factor Xa and WO 98/34115 discloses combinatorial libraries of 2,4-diaryltetrahydoisoquinoline compounds with potential use as antibacterials, NMDA antagonists or analgesics.

The present invention discloses novel tetrahydroquinoline compounds that are selective, non-peptide inhibitors of coagulation Factor XIa and/or plasma kallikrein and as such are useful in the treatment of thromboembolic and/or inflammatory disorders.

In addition, it is also desirable to find new compounds with improved pharmacological characteristics compared with known serine protease inhibitors. For example, it is preferred to find new compounds with improved factor XIa inhibitory activity and selectivity for factor XIa versus other serine proteases. Also, it is preferred to find new compounds with improved plasma kallikrein inhibitory activity and selectivity for plasma kallikrein versus other serine proteases. It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

SUMMARY OF THE INVENTION

Accordingly, the present invention provides novel tetrahydroquinoline derivatives, and analogues thereof, which are useful as selective inhibitors of serine protease enzymes, especially factor XIa and/or plasma kallikrein, or stereoisomers or pharmaceutically acceptable salts or prodrugs thereof.

The present invention also provides pharmaceutical compositions comprising a pharmaceutically acceptable carrier and a therapeutically effective amount of at least one of the compounds of the present invention or a pharmaceutically acceptable salt or prodrug form thereof.

The present invention also provides a method for modulation of the coagulation cascade and/or the contact activation system comprising administering to a host in need of such treatment a therapeutically effective amount of at least one of the compounds of the present invention or a pharmaceutically acceptable salt or prodrug form thereof.

The present invention also provides a method for treating thromboembolic diseases disorders comprising administering to a host in need of such treatment a therapeutically effective amount of at least one of the compounds of the present invention or a pharmaceutically acceptable salt or prodrug form thereof.

The present invention also provides a method for treating inflammatory diseases disorders comprising administering to a host in need of such treatment a therapeutically effective amount of at least one of the compounds of the present invention or a pharmaceutically acceptable salt or prodrug form thereof.

The present invention also provides novel tetrahydroquinoline derivatives, and analogues thereof, for use in therapy.

The present invention also provides the use of tetrahydroquinoline derivatives, and analogues thereof, for the manufacture of a medicament for the treatment of a thromboembolic disorder.

The present invention also provides the use of tetrahydroquinoline derivatives, and analogues thereof, for the manufacture of a medicament for the treatment of an inflammatory disorder.

These and other embodiments, which will become apparent during the following detailed description, have been achieved by the inventors' discovery that the presently claimed novel compounds of the present invention, or pharmaceutically acceptable salt or prodrug forms thereof, are effective factor XIa inhibitors and/or plasma kallikrein inhibitors.

DETAILED DESCRIPTION OF PREFERRED EMBODIMENTS

In a first aspect, the present invention provides, inter alia, compounds of Formula (I):

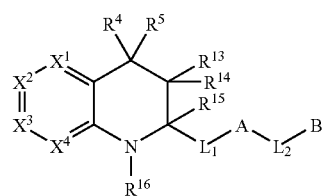

(I)

or a stereoisomer or pharmaceutically acceptable salts, hydrates, or prodrugs thereof, wherein:

$L_1$ is a bond, —$CH_2$—, —$CH_2CH_2$—, —$CH_2O$—, —$CH_2S(O)_p$—, —$CH_2NR^{10}$—, —$CH_2C(O)$—, or —$CONR^{10}$—;

$L_2$ is a bond, —(CR$^6$R$^{6a}$)$_{1-2}$—, —O—, —NR$^{10}$—, —C(O)—, —S(O)$_p$—, —(CR$^6$R$^{6a}$)C(O)—, —C(O)(CR$^6$R$^{6a}$)—, —(CR$^6$R$^{6a}$)O—, —O(CR$^6$R$^{6a}$)—, —(CR$^6$R$^{6a}$)NR$^{10}$—, —NR$^{10}$(CR$^6$R$^{6a}$)—, —(CR$^6$R$^{6a}$)S(O)$_p$—, —S(O)$_p$(CR$^6$R$^{6a}$)—, —C(O)O—, —OC(O)—, —C(O)NR$^8$—, —NR$^8$C(O)—, —S(O)NR$^8$—, —S(O)$_2$NR$^8$—, —NR$^8$S(O)—, or —NR$^8$S(O)$_2$—;

A is $C_{3-10}$ carbocycle substituted with 0-3 R$^{11}$ and 0-1 R$^{12}$, or a 5-12 membered heterocycle consisting of: carbon atoms and 1-4 heteroatoms selected from the group consisting of N, O, and S(O)$_p$, and substituted 0-3 R$^{11}$ and 0-1 R$^{12}$;

B is $C_{1-6}$ alkyl substituted with 0-2 R$^{11}$ and 0-1 R$^{12}$, $C_{2-6}$ alkenyl substituted with 0-2 R$^{11}$ and 0-1 R$^{12}$, $C_{2-6}$ alkynyl substituted with 0-2 R$^{11}$ and 0-1 R$^{12}$, $C_{3-10}$ carbocycle substituted with 0-3 R$^{11}$ and 0-1 R$^{12}$, or a 5-12 membered heterocycle consisting of: carbon atoms and 1-4 heteroatoms selected from the group consisting of N, O, and S(O)$_p$, and substituted with 0-3 R$^{11}$ and 0-1 R$^{12}$;

$X^1$, $X^2$, $X^3$ and $X^4$ independently represent CR$^1$, CR$^2$, CR$^3$ or N;

R$^1$ is H, —NH$_2$, —NH(C$_1$-C$_3$ alkyl), —N(C$_1$-C$_3$ alkyl)$_2$, —C(=NH)NH$_2$, —NHC(=NH)NH$_2$, —C(O)NH$_2$, —CH$_2$NH$_2$, —CH$_2$NH(C$_1$-C$_3$ alkyl), —CH$_2$N(C$_1$-C$_3$ alkyl)$_2$, —CH$_2$CH$_2$NH$_2$, —CH$_2$CH$_2$NH(C$_1$-C$_3$ alkyl), —CH$_2$CH$_2$N(C$_1$-C$_3$ alkyl)$_2$, —C(=NR$^8$)NR$^7$R$^9$, —NHC(=NR$^8$)NR$^7$R$^9$, —ONHC(=NR$^8$)NR$^7$R$^9$, —NR$^8$CH(=NR$^7$), —C(=NR$^{8a}$)NR$^7$R$^9$, —NHC(=NR$^{8a}$)NR$^7$R$^9$, —NR$^7$R$^8$, —C(O)NR$^{7a}$R$^8$, —S(O)$_p$NR$^8$R$^9$, F, Cl, Br, I, OCF$_3$, CF$_3$, OR$^a$, SR$^a$, CN or $C_{1-6}$ alkyl substituted with 1 R$^{1a}$;

R$^{1a}$ is —C(=NR$^8$)NR$^7$R$^9$, —NHC(=NR$^8$)NR$^7$R$^9$, —ONHC(=NR$^8$)NR$^7$R$^9$, —NR$^8$CH(=NR$^7$), —NR$^7$R$^8$, —C(O)NR$^{7a}$R$^8$, —S(O)$_p$NR$^8$R$^9$, F, OCF$_3$, CF$_3$, OR$^a$, SR$^a$, or CN;

R$^2$ is H, F, Cl, Br, I, OCF$_3$, CF$_3$, OR$^a$, SR$^a$, CN, NO$_2$, —NR$^7$R$^8$, —C(O)NR$^{7a}$R$^8$, —NR$^{10}$C(O)R$^b$, —S(O)$_p$NR$^8$R$^9$, —S(O)R$^c$, —S(O)$_2$R$^c$, $C_{1-6}$ alkyl substituted with 0-2 R$^{2a}$, $C_{2-6}$ alkenyl substituted with 0-2 R$^{2a}$, $C_{2-6}$ alkynyl substituted with 0-2 R$^{2a}$, —(CH$_2$)$_r$—$C_{3-10}$ carbocycle substituted with 0-3 R$^{2b}$, or —(CH$_2$)$_r$-5-10 membered heterocycle consisting of: carbon atoms and 1-4 heteroatoms selected from the group consisting of N, O, and S(O)$_p$, and substituted with 0-3 R$^{2b}$;

each R$^{2a}$ is, independently at each occurrence, H, F, OCF$_3$, CF$_3$, OR$^a$, SR$^a$, CN, —NR$^7$R$^8$, —C(O)NR$^{7a}$R$^8$, —NR$^{10}$C(O)R$^b$, —S(O)$_p$NR$^8$R$^9$, —S(O)R$^c$, or —S(O)$_2$R$^c$;

each R$^{2b}$ is, independently at each occurrence, H, F, Cl, Br, I, OR$^a$, SR$^a$, CN, NO$_2$, CF$_3$, —SO$_2$R$^c$, —NR$^7$R$^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, or $C_{1-4}$ alkyl-C(O)NH—;

alternately, when R$^1$ and R$^2$ are substituted on adjacent ring carbon atoms, they can be taken together with the ring carbon atoms to which they are attached to form a 5-7 membered carbocycle or heterocycle substituted with 0-2 R$^{2b}$;

R$^3$ is H, F, Cl, Br, I, OCF$_3$, CF$_3$, OR$^a$, SR$^a$, CN, NO$_2$, —NR$^7$R$^8$, —C(O)NR$^{7a}$R$^8$, —NR$^{10}$C(O)R$^b$, —S(O)$_p$NR$^8$R$^9$, —S(O)R$^c$, —S(O)$_2$R$^c$, $C_{1-6}$ alkyl substituted with 0-2 R$^{3a}$, $C_{2-6}$ alkenyl substituted with 0-2 R$^{3a}$, $C_{2-6}$ alkynyl substituted with 0-2 R$^{3a}$, —(CH$_2$)$_r$—$C_{3-10}$ carbocycle substituted with 0-3 R$^{3b}$, or —(CH$_2$)$_r$-5-10 membered heterocycle consisting of: carbon atoms and 1-4 heteroatoms selected from the group consisting of N, O, and S(O)$_p$, and substituted with 0-3 R$^{3b}$;

each R$^{3a}$ is, independently at each occurrence, H, F, OCF$_3$, CF$_3$, OR$^a$, SR$^a$, CN, —NR$^7$R$^8$, —C(O)NR$^{7a}$R$^8$, —NR$^{10}$C(O)R$^b$, —S(O)$_p$NR$^8$R$^9$, —S(O)R$^c$, or —S(O)$_2$R$^c$;

each R$^{3b}$ is, independently at each occurrence, H, F, Cl, Br, I, OR$^a$, SR$^a$, CN, NO$_2$, CF$_3$, —SO$_2$R$^c$, —NR$^7$R$^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, or $C_{1-4}$ alkyl-C(O)NH—;

R$^4$ is H, F, OR$^a$, SR$^a$, —NR$^7$R$^8$, —NR$^{10}$C(O)NR$^{7a}$R$^8$, —NR$^{10}$SO$_2$R$^c$, —C(O)OR$^a$, —C(O)NR$^{7a}$R$^8$, $C_{1-4}$ haloalkyl, $C_{1-6}$ alkyl substituted with 0-3 R$^{4a}$, $C_{2-6}$ alkenyl substituted with 0-3 R$^{4a}$, $C_{2-6}$ alkynyl substituted with 0-3 R$^{4a}$, —(CH$_2$)$_r$—$C_{3-10}$ carbocycle substituted with 0-3 R$^{4b}$, or —(CH$_2$)$_r$-5-10 membered heterocycle consisting of: carbon atoms and 1-4 heteroatoms selected from the group consisting of N, O, and S(O)$_p$, and substituted with 0-3 R$^{4b}$;

each R$^{4a}$ is, independently at each occurrence, H, $C_{1-4}$ alkyl, OR$^a$, F, =O, CF$_3$, CN, —C(O)R$^a$, C(O)OR$^a$, —C(O)NR$^{7a}$R$^8$, —NR$^{10}$COR$^c$, or —S(O)$_p$R$^b$;

each R$^{4b}$ is, independently at each occurrence, H, OH, Cl, F, Br, I, CN, NO$_2$, CF$_3$, —C(O)OR$^a$, —SO$_2$R$^c$, —NR$^7$R$^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-C(O)NH—, —C(O)NR$^{7a}$R$^8$, —NR$^{10}$C(O)R$^b$, —NR$^{10}$S(O)$_2$NR$^8$R$^9$, or —S(O)$_2$NR$^8$R$^9$;

R$^5$ is H, F, $C_{1-4}$ haloalkyl, $C_{1-6}$ alkyl substituted with 0-3 R$^{5a}$, $C_{2-6}$ alkenyl substituted with 0-3 R$^{5a}$, $C_{2-6}$ alkynyl substituted with 0-3 R$^{5a}$, —(CH$_2$)$_r$—$C_{3-10}$ carbocycle substituted with 0-3 R$^{5b}$, or —(CH$_2$)$_r$-5-10 membered heterocycle consisting of: carbon atoms and 1-4 heteroatoms selected from the group consisting of N, O, and S(O)$_p$, and substituted with 0-3 R$^{5b}$;

each R$^{5a}$ is, independently at each occurrence, H, $C_{1-4}$ alkyl, OR$^a$, F, =O, CF$_3$, CN, —C(O)R$^a$, —C(O)OR$^a$, —C(O)NR$^{7a}$R$^8$, or —S(O)$_p$R$^c$;

each R$^{5b}$ is, independently at each occurrence, H, OH, Cl, F, Br, I, CN, NO$_2$, CF$_3$, —C(O)OR$^a$, —SO$_2$R$^c$, —NR$^7$R$^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, or $C_{1-4}$ alkyl-C(O)NH—;

each R$^6$ is, independently at each occurrence, H, $C_{1-4}$ alkyl, —(CH$_2$)$_r$C(O)OR$^a$, —(CH$_2$)$_r$S(O)$_2$NR$^{7a}$R$^8$, or —(CH$_2$)$_r$OR$^a$;

each R$^{6a}$ is, independently at each occurrence, H or $C_{1-4}$ alkyl;

each R$^7$ is, independently at each occurrence, H, $C_{1-6}$ alkyl, —(CH$_2$)$_n$-phenyl, ($C_{1-6}$ alkyl)C(O)—, ($C_{6-10}$ aryl)-$C_{0-4}$ alkyl-C(O)—, ($C_{3-6}$ cycloalkyl)-$C_{0-4}$ alkyl-C(O)—, (5-10 membered heteroaryl)-$C_{0-4}$ alkyl-C(O)—, ($C_{1-4}$ alkyl)OC(O)—, ($C_{6-10}$ aryl)-$C_{0-4}$ alkyl-OC(O)—, ($C_{1-4}$ alkyl)-C(O)O—($C_{1-4}$ alkyl)-OC(O)—, ($C_{6-10}$ aryl)-C(O)O—($C_{1-4}$ alkyl)-OC(O)—, (5-10 membered heteroaryl)-CH$_2$—OC(O)—, ($C_{1-6}$ alkyl)-NHC(O)—, ($C_{6-10}$ aryl)-$C_{0-4}$ alkyl-NHC(O)—, (5-10 membered heteroaryl)-$C_{0-4}$ alkyl-NHC(O)—, ($C_{1-6}$ alkyl)-S(O)$_2$—, ($C_{6-10}$ aryl)-($C_{0-4}$ alkyl)-S(O)$_2$—, (5-10 membered heteroaryl)-$C_{0-4}$ alkyl-S(O)$_2$—, ($C_{1-6}$ alkyl)$_2$NC(O)—, phenyl-NHC(O)—, benzyl-NHC(O)—, (phenyl)($C_{1-6}$ alkyl)NC(O)—, or (benzyl)($C_{1-6}$ alkyl)NC(O)—, wherein said phenyl, aryl and heteroaryl are substituted with 0-2 R$^f$;

each R$^{7a}$ is, independently at each occurrence, H, $C_{1-4}$ alkyl substituted with 0-2 R$^{7b}$ or 0-2 R$^{7c}$, —(CH$_2$)$_r$—$C_{3-10}$ carbocycle substituted with 0-3 R$^f$, or a —(CH$_2$)$_r$-5-12 membered heterocycle consisting of: carbon atoms and 1-4 heteroatoms selected from the group consisting of N, O, and S(O)$_p$, and substituted 0-3 R$^f$;

each R$^{7b}$ is, independently at each occurrence, =O, OR$^g$, F, Cl, Br, I, CN, NO$_2$, —NR$^7$R$^8$, —C(O)R$^g$, —C(O)OR$^g$, —NR$^8$C(O)R$^g$, —C(O)NR$^8$R$^9$, —NR$^8$C(O)NR$^8$R$^9$, —SO$_2$NR$^8$R$^9$, —NR$^8$SO$_2$NR$^8$R$^9$, —NR$^8$SO$_2$—$C_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{7c}$ is, independently at each occurrence, C$_{3-10}$ carbocycle substituted with 0-3 R$^f$; or a 5-12 membered heterocycle consisting of: carbon atoms and 1-4 heteroatoms selected from the group consisting of N, O, and S(O)$_p$, and substituted 0-3 R$^f$;

each R$^8$ is, independently at each occurrence, H, C$_{1-6}$ alkyl, or —(CH$_2$)$_n$-phenyl;

each R$^{8a}$ is, independently at each occurrence, H, OH, C$_{1-6}$ alkyl, —(CH$_2$)$_n$-phenyl, (C$_{1-6}$ alkyl)C(O)—, (C$_{6-10}$ aryl)-C$_{0-4}$ alkyl-C(O)—, (C$_{3-6}$ cycloalkyl)-C$_{0-4}$ alkyl-C(O)—, (5-10 membered heteroaryl)-C$_{0-4}$ alkyl-C(O)—, (C$_{1-4}$ alkyl)OC(O)—, (C$_{6-10}$ aryl)-C$_{0-4}$ alkyl-OC(O)—, (C$_{1-4}$ alkyl)-C(O)O—(C$_{1-4}$ alkyl)-OC(O)—, (C$_{6-10}$ aryl)-C(O)O—(C$_{1-4}$ alkyl)-OC(O)—, (5-10 membered heteroaryl)-CH$_2$—OC(O)—, (C$_{1-6}$ alkyl)-NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-S(O)$_2$—, (C$_{6-10}$ aryl)-(C$_{0-4}$ alkyl)-S(O)$_2$—, (5-10 membered heteroaryl)-C$_{0-4}$ alkyl-S(O)$_2$—, C$_{1-4}$ alkoxy, (C$_{1-4}$ alkyl)C(O)O—, or (C$_{6-10}$ aryl)-(C$_{0-4}$ alkyl)-C(O)O—; wherein said phenyl, aryl and heteroaryl are substituted with 0-2 R$^f$;

alternatively, R$^7$ and R$^8$, or R$^{7a}$ and R$^8$, when attached to the same nitrogen, combine to form a 5-10 membered heterocyclic ring consisting of carbon atoms and 0-2 additional heteroatoms selected from the group consisting of N, O, and S(O)$_p$;

each R$^9$ is, independently at each occurrence, H, C$_{1-6}$ alkyl, or —(CH$_2$)$_n$-phenyl;

each R$^{10}$ is, independently at each occurrence, H, C$_{1-6}$ alkyl substituted with 0-2 R$^{10a}$, C$_{2-6}$ alkenyl substituted with 0-2 R$^{10a}$, C$_{2-6}$ alkynyl substituted with 0-2 R$^{10a}$, (C$_{1-6}$ alkyl)C(O)—, (C$_{3-6}$ cycloalkyl)C$_{1-3}$ alkyl-C(O)—, (C$_{3-6}$ cycloalkyl)C(O)—, phenyl-C(O)—, benzyl-C(O)—, benzyl-S(O)$_2$—, (C$_{3-6}$ alkyl)NHC(O)—, (C$_{1-6}$ alkyl)$_2$NC(O)—, phenyl-NHC(O)—, benzyl-NHC(O)—, (phenyl)(C$_{1-6}$ alkyl)NC(O)—, (benzyl)(C$_{1-6}$ alkyl)NC(O)—, (C$_{1-6}$ alkyl)-S(O)$_2$—, phenyl-S(O)$_2$—, —(CH$_2$)$_r$—C$_{3-10}$ carbocycle substituted with 0-3 R$^d$, or —(CH$_2$)$_r$-5-10 membered heterocycle consisting of carbon atoms and 1-4 heteroatoms selected from the group consisting of N, O, and S(O)$_p$, and substituted with 0-3 R$^d$;

each R$^{10a}$ is, independently at each occurrence, H, C$_{1-4}$ alkyl, OR$^a$, Cl, F, Br, I, =O, CF$_3$, CN, NO$_2$, —C(O)R$^a$, —C(O)OR$^a$, —C(O)NR$^{7a}$R$^8$, or —S(O)$_p$R$^c$;

each R$^{11}$ is, independently at each occurrence, H, =O, —(CH$_2$)$_r$—OR$^a$, F, Cl, Br, I, CN, NO$_2$, —(CH$_2$)$_r$—NR$^7$R$^8$, —C(O)R$^a$, —C(O)OR$^a$, —NR$^8$C(O)R$^a$, —NR$^8$C(O)OR$^a$, —C(O)NR$^{7a}$R$^8$, —NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^{11a}$, C$_{2-6}$ alkenyl substituted with 0-2 R$^{11a}$, C$_{2-6}$ alkynyl substituted with 0-2 R$^{11a}$, C$_{1-6}$ alkyl substituted with 0-2 R$^{11b}$, C$_{2-6}$ alkenyl substituted with 0-2 R$^{11b}$, or C$_{2-6}$ alkynyl substituted with 0-2 R$^{11b}$;

each R$^{11a}$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^a$, —C(O)NR$^{7a}$R$^8$, —NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{11b}$ is, independently at each occurrence, C$_{3-10}$ carbocycle substituted with 0-3 R$^d$; or a 5-12 membered heterocycle consisting of: carbon atoms and 1-4 heteroatoms selected from the group consisting of N, O, and S(O)$_p$, and substituted 0-3 R$_d$;

each R$^{12}$ is, independently at each occurrence, OR$^{12a}$, —C(O)NR$^{7a}$R$^8$, —(CH$_2$)$_r$CO$_2$R$^{12a}$, —(CH$_2$)$_r$SO$_3$H, —OSO$_3$H, —(CH$_2$)$_r$PO$_3$H, —OPO$_3$H$_2$, —PO$_3$H$_2$, —NHPO$_3$H$_2$, —NHCOCF$_3$, —NHSO$_2$CF$_3$, —CONHNHSO$_2$CF$_3$, —C(CF$_3$)$_2$OH, —SO$_2$NHR$^{12a}$, —CONHSO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, —CONHOR$^{12b}$,

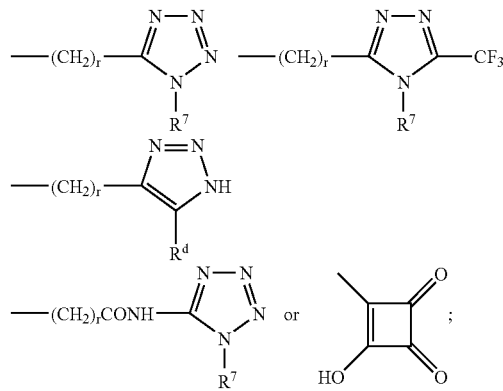

each R$^{12a}$ is, independently at each occurrence, H, C$_{1-6}$ alkyl, —(CH$_2$)$_r$—C$_{3-10}$ carbocycle substituted with 0-3 R$^d$; or —(CH$_2$)$_r$-5-10 membered heterocycle consisting of carbon atoms and 1-4 heteroatoms selected from the group consisting of N, O, and S(O)$_p$, and substituted with 0-3 R$^d$;

each R$^{12b}$ is, independently at each occurrence, C$_{1-6}$ alkyl substituted with 0-2 R$^{12c}$, C$_{2-6}$ alkenyl substituted with 0-2 R$^{12c}$, C$_{2-6}$ alkynyl substituted with 0-2 R$^{12c}$, —(CH$_2$)$_r$—C$_{3-10}$ carbocycle substituted with 0-3 R$^{12c}$, or —(CH$_2$)$_r$-5-10 membered heterocycle consisting of: carbon atoms and 1-4 heteroatoms selected from the group consisting of N, O, and S(O)$_p$, and substituted with 0-3 R$^{12c}$;

each R$^{12c}$ is, independently at each occurrence, H, F, Cl, Br, I, CF$_3$, OCF$_3$, CN, NO$_2$, OR$^a$, —CO$_2$R$^a$, —NR$^7$R$^8$, —SO$_2$R$^c$, C$_{1-6}$ alkyl, C$_{2-6}$ alkenyl, C$_{2-6}$ alkynyl, —(CH$_2$)$_r$—C$_{3-10}$ carbocycle substituted with 0-3 R$^d$; or —(CH$_2$)$_r$-5-10 membered heterocycle consisting of carbon atoms and 1-4 heteroatoms selected from the group consisting of N, O, and S(O)$_p$, and substituted with 0-3 R$^d$;

R$^{13}$ is H, C$_{1-4}$ alkyl, (NR$^7$R$^8$)C$_{1-4}$ alkyl, (SR$^c$)C$_{1-4}$ alkyl, (OR$^a$)C$_{1-4}$ alkyl, OR$^a$, F, CF$_3$, —C(O)R$^a$, —C(O)OR$^a$, —C(O)NR$^{7a}$R$^8$, or —S(O)$_p$R$^c$;

R$^{14}$ is H, C$_{1-4}$ alkyl, (NR$^7$R$^8$)C$_{1-4}$ alkyl, (SR$^c$)C$_{1-4}$ alkyl, (OR$^a$)C$_{1-4}$ alkyl, OR$^a$, F, CF$_3$, —C(O)R$^a$, —C(O)OR$^a$, —C(O)NR$^{7a}$R$^8$, or —S(O)$_p$R$^c$;

alternately, R$^{13}$ and R$^{14}$ may be taken together to be =O;

R$^{15}$ is H or C$_{1-4}$ alkyl;

R$^{16}$ is H, C$_{1-4}$ alkyl, benzyl, C$_{1-4}$ alkyl-C(O)—, C$_{1-4}$ alkyl-S(O)$_2$—, or C$_{1-4}$ alkyl-OC(O)—;

each R$^a$ is, independently at each occurrence, H, C$_{1-4}$ alkyl, —(CH$_2$)$_r$—CO$_2$R$^g$, —(CH$_2$)$_r$—C$_{3-7}$ cycloalkyl, —(CH$_2$)$_r$—C$_{6-10}$ aryl, or —(CH$_2$)$_r$-5-10 membered heteroaryl, wherein said aryl or heteroaryl groups are substituted with 0-2 R$^f$;

each R$^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-2 R$^d$, or —(CH$_2$)$_r$-5-10 membered heterocycle containing from 1-4 heteroatoms selected from the group consisting of N, O, and S(O)$_p$ and substituted with 0-2 R$^d$;

each R$^c$ is, independently at each occurrence, C$_{1-4}$ alkyl, C$_{6-10}$ aryl, 5-10 membered heteroaryl, (C$_{6-10}$ aryl)-C$_{1-4}$ alkyl, or (5-10 membered heteroaryl)-$C_{1-4}$ alkyl, wherein said aryl and heteroaryl groups are substituted with 0-2 $R^d$;

each $R^d$ is, independently at each occurrence, H, =O, $OR^a$, F, Cl, Br, I, CN, $NO_2$, $-NR^7R^8$, $-C(O)R^a$, $-C(O)OR^a$, $-NR^8C(O)R^a$, $-C(O)NR^{7a}R^8$, $-SO_2NR^8R^9$, $-NR^8SO_2NR^8R^9$, $-NR^8SO_2-C_{1-4}$ alkyl, $-NR^8SO_2CF_3$, $-NR^8SO_2$-phenyl, $-S(O)_2CF_3$, $-S(O)_p-C_{1-4}$ alkyl, $-S(O)_p$-phenyl, $-(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

each $R^e$ is, independently at each occurrence, =O, $OR^a$, F, Cl, Br, I, CN, $NO_2$, $-NR^8R^9$, $-C(O)R^a$, $-C(O)OR^a$, $-NR^8C(O)R^a$, $-C(O)NR^{7a}R^8$, $-SO_2NR^8R^9$, $-NR^8SO_2NR^8R^9$, $-NR^8SO_2-C_{1-4}$ alkyl, $-NR^8SO_2CF_3$, $-NR^8SO_2$-phenyl, $-S(O)_2CF_3$, $-S(O)_p-C_{1-4}$ alkyl, $-S(O)_p$-phenyl, or $-(CF_2)_rCF_3$;

each $R^f$ is, independently at each occurrence, H, =O, $OR^g$, F, Cl, Br, I, CN, $NO_2$, $-NR^8R^9$, $-C(O)R^g$, $-C(O)OR^g$, $-NR^8C(O)R^9$, $-C(O)NR^8R^9$, $-SO_2NR^8R^9$, $-NR^8SO_2NR^8R^9$, $-NR^8SO_2-C_{1-4}$ alkyl, $-NR^8SO_2CF_3$, $-NR^8SO_2$-phenyl, $-S(O)_2CF_3$, $-S(O)_p-C_{1-4}$ alkyl, $-S(O)_p$-phenyl, $-(CF_2)_rCF_3$, $C_{1-6}$ alkyl, $C_2-C_6$ alkenyl, or $C_2-C_6$ alkynyl;

each $R^g$ is, independently at each occurrence, H, $C_{1-6}$ alkyl, or $-(CH_2)_n$-phenyl;

n, at each occurrence, is selected from 0, 1, 2, 3, and 4;

p, at each occurrence, is selected from 0, 1, and 2;

r, at each occurrence, is selected from 0, 1, 2, 3, and 4; and provided that when $L_1$ is a bond and A is phenyl or a 6-membered aromatic N-heterocycle, then ring A is not substituted ortho to $L_1$ with OH, halogen, $-CO_2H$, $-C(O)O-C_{1-4}$ alkyl, $-O$-phenyl, $-O$-benzyl, $-NR^7R^8$, $-CH_2OR^a$, haloalkyl, $-S-C_{1-4}$ alkyl, or $-NHSO_2-C_{1-4}$ alkyl.

In a second aspect, the present invention includes a compound of Formula (I):

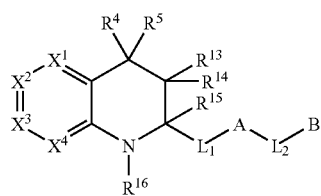

(I)

or a stereoisomer or a pharmaceutically acceptable salt, hydrate, or prodrug thereof, wherein:

$L_1$ is a bond;

$L_2$ is a bond, $-CH_2-$, or $-O-$;

A is phenyl substituted with 1 $R^{11c}$ and 0-1 $R^{12}$;

B is phenyl substituted with 0-3 $R^{11}$ and 0-1 $R^{12}$;

$X^1$, $X^2$, $X^3$ and $X^4$ independently represent $CR^1$, $CR^2$, or $CR^3$;

$R^1$ is H, $-NH_2$, $-NH(C_1-C_3$ alkyl), $-N(C_1-C_3$ alkyl)$_2$, $-C(=NH)NH_2$, $-NHC(=NH)NH_2$, $-C(O)NH_2$, $-CH_2NH_2$, $-CH_2NH(C_1-C_3$ alkyl), $-CH_2N(C_1-C_3$ alkyl)$_2$, $-CH_2CH_2NH_2$, $-CH_2CH_2NH(C_1-C_3$ alkyl), $-CH_2CH_2N(C_1-C_3$ alkyl)$_2$, $-C(=NR^8)NR^7R^9$, $-NHC(=NR^8)NR^7R^9$, $-ONHC(=NR^8)NR^7R^9$, $-NR^8CH(=NR^7)$, $-C(=NR^{8a})NR^7R^9$, $-NHC(=NR^{8a})NR^7R^9$, $-NR^7R^8$, $-C(O)NR^{7a}R^8$, $-S(O)_pNR^8R^9$, F, Cl, Br, I, $OCF_3$, $CF_3$, $OR^a$, $SR^a$, CN or $C_{1-6}$ alkyl substituted with 1 $R^{1a}$;

$R^{1a}$ is $-C(=NR^8)NR^7R^9$, $-NHC(=NR^8)NR^7R^9$, $-ONHC(=NR^8)NR^7R^9$, $-NR^8CH(=NR^7)$, $-NR^7R^8$, $-C(O)NR^{7a}R^8$, $-S(O)_pNR^8R^9$, F, $OCF_3$, $CF_3$, $OR^a$, $SR^a$, or CN;

$R^2$ is H, F, Cl, Br, I, $OCF_3$, $CF_3$, $OR^a$, $SR^a$, CN, $NO_2$, $-NR^7R^8$, $-C(O)NR^{7a}R^8$, $-NR^{10}C(O)R^b$, $-S(O)_pNR^8R^9$, $-S(O)R^c$, $-S(O)_2R^c$, $C_{1-6}$ alkyl substituted with 0-2 $R^{2a}$, $C_{2-6}$ alkenyl substituted with 0-2 $R^{2a}$, $C_{2-6}$ alkynyl substituted with 0-2 $R^{2a}$, $C_{3-10}$ carbocycle substituted with 0-3 $R^{2b}$, or $-(CH_2)_r$-5-10 membered heterocycle consisting of: carbon atoms and 1-4 heteroatoms selected from the group consisting of N, O, and $S(O)^p$, and substituted with 0-3 $R^{2b}$;

each $R^{2a}$ is, independently at each occurrence, H, F, $OCF_3$, $CF_3$, $OR^a$, $SR^a$, CN, $-NR^7R^8$, $-C(O)NR^{7a}R^8$, $-NR^{10}C(O)R^b$, $-S(O)_pNR^8R^9$, $-S(O)R^c$, or $-S(O)_2R^c$;

each $R^{2b}$ is, independently at each occurrence, H, F, Cl, Br, I, $OR^a$, $SR^a$, CN, $NO_2$, $CF_3$, $-SO_2R^c$, $-NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, or $C_{1-4}$ alkyl-C(O)NH—;

$R^3$ is H, F, Cl, Br, I, $OCF_3$, $CF_3$, $OR^a$, $SR^a$, CN, $NO_2$, $-NR^7R^8$, $-C(O)NR^{7a}R^8$, $-NR^{10}C(O)R^b$, $-S(O)_pNR^8R^9$, $-S(O)R^c$, $-S(O)_2R^c$, $C_{1-6}$ alkyl substituted with 0-2 $R^{3a}$, $C_{2-6}$ alkenyl substituted with 0-2 $R^{3a}$, $C_{2-6}$ alkynyl substituted with 0-2 $R^{3a}$, $C_{3-10}$ carbocycle substituted with 0-3 $R^{3b}$, or $-(CH_2)_r$-5-10 membered heterocycle consisting of: carbon atoms and 1-4 heteroatoms selected from the group consisting of N, O, and $S(O)_p$, and substituted with 0-3 $R^{3b}$;

each $R^{3a}$ is, independently at each occurrence, H, F, $OCF_3$, $CF_3$, $OR^a$, $SR^a$, CN, $-NR^7R^8$, $-C(O)NR^{7a}R^8$, $-NR^{10}C(O)R^b$, $-S(O)_pNR^8R^9$, $-S(O)R^c$, or $-S(O)_2R^c$;

each $R^{3b}$ is, independently at each occurrence, H, F, Cl, Br, I, $OR^a$, $SR^a$, CN, $NO_2$, $CF_3$, $-SO_2R^c$, $-NR^7R^8$, $C_{1-6}$ alkyl, $C_{2-6}$ alkenyl, $C_{2-6}$ alkynyl, $C_{3-6}$ cycloalkyl $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, or $C_{1-4}$ alkyl-C(O)NH—;

$R^4$ is phenyl substituted with 0-3 $R^{4b}$;

each $R^{4b}$ is, independently at each occurrence, H, OH, Cl, F, Br, I, CN, $NO_2$, $CF_3$, $-C(O)OR^a$, $-SO_2R^c$, $-NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-C(O)NH—, $-C(O)NR^{7a}R^8$, $-NR^{10}C(O)R^b$, $-NR^{10}S(O)_2NR^8R^9$, or $-S(O)_2NR^8R^9$;

$R^5$ is H, $C_{1-4}$ haloalkyl, or $C_{1-6}$ alkyl substituted with 0-3 $R^{5a}$;

each $R^{5a}$ is, independently at each occurrence, H, $C_{1-4}$ alkyl, $OR^a$, F, =O, $CF_3$, CN, $-C(O)R^a$, $-C(O)OR^a$, $-C(O)NR^{7a}R^8$, or $-S(O)_pR^c$;

each $R^7$ is, independently at each occurrence, H, $C_{1-6}$ alkyl, $-(CH_2)_n$-phenyl, $(C_{1-6}$ alkyl)C(O)—, $(C_{6-10}$ aryl)-$C_{0-4}$ alkyl-C(O)—, $(C_{3-6}$ cycloalkyl)-$C_{0-4}$ alkyl-C(O)—, $(C_{6-10}$ aryl)-$C_{0-4}$ alkyl-OC(O)—, $(C_{1-4}$ alkyl)-C(O)O—$(C_{1-4}$ alkyl)-OC(O)—, $(C_{6-10}$ aryl)-C(O)O—$(C_{1-4}$ alkyl)-OC(O)—, $(C_{1-6}$ alkyl)-NHC(O)—, $(C_{6-10}$ aryl)-$C_{0-4}$ alkyl-NHC(O)—, $(C_{1-6}$ alkyl)-S(O)$_2$—, $(C_{6-10}$ aryl)-$(C_{0-4}$ alkyl)-S(O)$_2$—, $(C_{1-6}$ alkyl)$_2$NC(O)—, phenyl-NHC(O)—, benzyl-NHC(O)—, (phenyl)($C_{1-6}$ alkyl)NC(O)—, or (benzyl)($C_{1-6}$ alkyl)NC(O)—, wherein said phenyl and aryl are substituted with 0-2 $R^f$;

each $R^{7a}$ is, independently at each occurrence, H, $C_{1-4}$ alkyl substituted with 0-2 $R^{7b}$ or 0-2 $R^{7c}$, or $-(CH_2)_r$—$C_{3-10}$ carbocycle substituted with 0-3 $R^f$;

each $R^{7b}$ is, independently at each occurrence, =O, $OR^g$, F, Cl, Br, I, CN, $NO_2$, $-NR^7R^8$, $-C(O)R^g$, $-C(O)OR^g$, $-NR^8C(O)R^g$, $-C(O)NR^8R^9$, $-NR^8C(O)NR^8R^9$, $-SO_2NR^8R^9$, $-NR^8SO_2NR^8R^9$, $-NR^8SO_2-C_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{7c}$ is, independently at each occurrence, C$_{3-10}$ carbocycle substituted with 0-3 R$^f$;

R$^{7d}$ is —(CH$_2$)$_r$-5-12 membered heterocycle consisting of: carbon atoms and 1-4 heteroatoms selected from the group consisting of N, O, and S(O)$_p$, and substituted 0-3 R$^f$;

each R$^8$ is, independently at each occurrence, H, C$_{1-6}$ alkyl, or —(CH$_2$)$_n$-phenyl;

each R$^{8a}$ is, independently at each occurrence, H, OH, C$_{1-6}$ alkyl, —(CH$_2$)$_r$-phenyl, (C$_{1-6}$ alkyl)C(O)—, (C$_{6-10}$ aryl)-C$_{0-4}$ alkyl-C(O)—, (C$_{3-6}$ cycloalkyl)-C$_{0-4}$ alkyl-C(O)—, (C$_{1-4}$ alkyl)OC(O)—, (C$_{6-10}$ aryl)-C$_{0-4}$ alkyl-OC(O)—, (C$_{1-4}$ alkyl)-C(O)O—(C$_{1-4}$ alkyl)-OC(O)—, (C$_{6-10}$ aryl)-C(O)O—(C$_{1-4}$ alkyl)-OC(O)—, (C$_{1-6}$ alkyl)-NHC(O)—, (C$_{6-10}$ aryl)-C$_{0-4}$ alkyl-NHC(O)—, (C$_{1-6}$ alkyl)-S(O)$_2$—, (C$_{6-10}$ aryl)-(C$_{0-4}$ alkyl)-S(O)$_2$—, C$_{1-4}$ alkoxy, (C$_{1-4}$ alkyl)C(O)O—, or (C$_{6-10}$ aryl)-(C$_{0-4}$ alkyl)-C(O)O—; wherein said phenyl and aryl are substituted with 0-2 R$^f$;

each R$^9$ is, independently at each occurrence, H, C$_{1-6}$ alkyl, or —(CH$_2$)$_n$-phenyl;

each R$^{10}$ is, independently at each occurrence, H, C$_{1-6}$ alkyl substituted with 0-2 R$^{10a}$, C$_{2-6}$ alkenyl substituted with 0-2 R$^{10a}$, C$_{2-6}$ alkynyl substituted with 0-2 R$^{10a}$, (C$_{1-6}$ alkyl)C(O)—, (C$_{3-6}$ cycloalkyl)C$_{1-3}$ alkyl-C(O)—, (C$_{3-6}$ cycloalkyl)C(O)—, phenyl-C(O)—, benzyl-C(O)—, benzyl-S(O)$_2$—, (C$_{1-6}$ alkyl)NHC(O)—, (C$_{1-6}$ alkyl)$_2$NC(O)—, phenyl-NHC(O)—, benzyl-NHC(O)—, (phenyl)(C$_{1-6}$ alkyl)NC(O)—, (benzyl)(C$_{1-6}$ alkyl)NC(O)—, (C$_{1-6}$ alkyl)-S(O)$_2$—, phenyl-S(O)$_2$—, —(CH$_2$)$_r$—C$_{3-10}$ carbocycle substituted with 0-3 R$^d$, or —(CH$_2$)$_r$-5-10 membered heterocycle consisting of carbon atoms and 1-4 heteroatoms selected from the group consisting of N, O, and S(O)$_p$, and substituted with 0-3 R$^d$;

each R$^{10a}$ is, independently at each occurrence, H, C$_{1-4}$ alkyl, OR$^a$, Cl, F, Br, I, =O, CF$_3$, CN, NO$_2$, —C(O)R$^a$, —C(O)OR$^a$, —C(O)NR$^{7a}$R$^8$, or —S(O)$_p$R$^c$;

each R$^{11}$ is, independently at each occurrence, H, =O, —(CH$_2$)$_r$—OR$^a$, F, Cl, Br, I, CN, NO$_2$, —(CH$_2$)$_r$—NR$^7$R$^8$, —C(O)R$^a$, —C(O)OR$^a$, —NR$^8$C(O)R$^a$, —NR$^8$C(O)OR$^a$, —C(O)NR$^{7a}$R$^8$, —NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^{11a}$, C$_{2-6}$ alkenyl substituted with 0-2 R$^{11a}$, C$_{2-6}$ alkynyl substituted with 0-2 R$^{11a}$, C$_{1-6}$ alkyl substituted with 0-2 R$^{11b}$, C$_{2-6}$ alkenyl substituted with 0-2 R$^{11b}$, or C$_{2-6}$ alkynyl substituted with 0-2 R$^{11b}$;

each R$^{11a}$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^a$, —C(O)NR$^{7a}$R$^8$, NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{11b}$ is, independently at each occurrence, C$_{3-10}$ carbocycle substituted with 0-3 R$^d$; or a 5-12 membered heterocycle consisting of: carbon atoms and 1-4 heteroatoms selected from the group consisting of N, O, and S(O)$_p$, and substituted 0-3 R$^d$;

R$^{11c}$ is —C(O)R$^{a1}$, —C(O)OR$^{a1}$, —NR$^8$C(O)R$^{a1}$, —NR$^8$C(O)OR$^{a1}$, —C(O)NR$^{7a}$R$^8$, C$_{1-6}$ alkyl substituted with 1 R$^{11d}$, C$_{2-6}$ alkenyl substituted with 1 R$^{11d}$, or C$_{2-6}$ alkynyl substituted with 1 R$^{11d}$;

each R$^{11d}$ is, independently at each occurrence, a 5-12 membered heterocycle consisting of: carbon atoms and 1-4 heteroatoms selected from the group consisting of N, O, and S(O)$_p$, and substituted 0-3 R$^d$;

each R$^{12}$ is, independently at each occurrence, OR$^{12a}$, —C(O)NR$^{7a}$R$^8$, —(CH$_2$)$_r$CO$_2$R$^{12a}$, —(CH$_2$)$_r$SO$_3$H, —OSO$_3$H, —(CH$_2$)$_r$PO$_3$H, —OPO$_3$H$_2$, —PO$_3$H$_2$, —NHPO$_3$H$_2$, —NHCOCF$_3$, —NHSO$_2$CF$_3$, —CONHNHSO$_2$CF$_3$, —C(CF$_3$)$_2$OH, —SO$_2$NHR$^{12a}$, —CONHSO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, —CONHOR$^{12b}$,

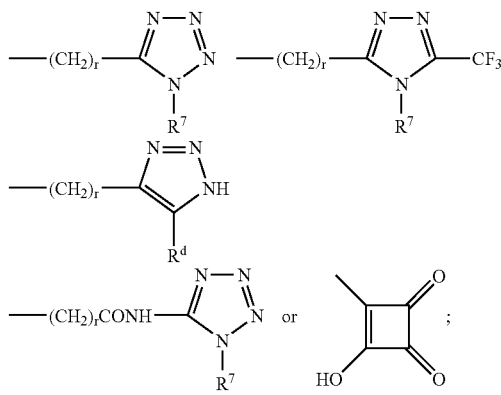

each R$^{12a}$ is, independently at each occurrence, H, C$_{1-6}$ alkyl, —(CH$_2$)$_r$—C$_{3-10}$ carbocycle substituted with 0-3 R$^d$; or —(CH$_2$)$_r$-5-10 membered heterocycle consisting of carbon atoms and 1-4 heteroatoms selected from the group consisting of N, O, and S(O)$_p$, and substituted with 0-3 R$^d$;

each R$^{12b}$ is, independently at each occurrence, C$_{1-6}$ alkyl substituted with 0-2 R$^{12c}$, C$_{2-6}$ alkenyl substituted with 0-2 R$^{12c}$, C$_{2-6}$ alkynyl substituted with R$^{12c}$, —(CH$_2$)$_r$—C$_{3-10}$ carbocycle substituted with 0-3 R$^{12c}$, or —(CH$_2$)$_r$-5-10 membered heterocycle consisting of: carbon atoms and 1-4 heteroatoms selected from the group consisting of N, O, and S(O)$_p$, and substituted with 0-3 R$^{12c}$;

each R$^{12c}$ is, independently at each occurrence, H, F, Cl, Br, I, CF$_3$, OCF$_3$, CN, NO$_2$, OR$^a$, —CO$_2$R$^a$, —NR$^7$R$^8$, —SO$_2$R$^c$, C$_{1-6}$ alkyl, C$_{2-6}$ alkenyl, C$_{2-6}$ alkynyl, —(CH$_2$)$_r$—C$_{3-10}$ carbocycle substituted with 0-3 R$^d$; or —(CH$_2$)$_r$-5-10 membered heterocycle consisting of carbon atoms and 1-4 heteroatoms selected from the group consisting of N, O, and S(O)$_p$, and substituted with 0-3 R$^d$;

R$^{13}$ is H, C$_{1-4}$ alkyl, (NR$^7$R$^8$)C$_{1-4}$ alkyl, (SR$^c$)C$_{1-4}$ alkyl, (OR$^a$)C$_{1-4}$ alkyl, OR$^a$, F, CF$_3$, —C(O)R$^a$, —C(O)OR$^a$, —C(O)NR$^{7a}$R$^8$, or —S(O)$_p$R$^c$;

R$^{14}$ is H, C$_{1-4}$ alkyl, (NR$^7$R$^8$)C$_{1-4}$ alkyl, (SR$^c$)C$_{1-4}$ alkyl, (OR$^a$)C$_{1-4}$ alkyl, OR$^a$, F, CF$_3$, —C(O)R$^a$, —C(O)OR$^a$, —C(O)NR$^{7a}$R$^8$, or —S(O)$_p$R$^c$;

alternately, R$^{13}$ and R$^{14}$ may be taken together to be =O;

R$^{15}$ is H or C$_{1-4}$ alkyl;

R$^{16}$ is H, C$_{1-4}$ alkyl, benzyl, C$_{1-4}$ alkyl-C(O)—, C$_{1-4}$ alkyl-S(O)$_2$—, or C$_{1-4}$ alkyl-OC(O)—; each R$^a$ is, independently at each occurrence, H, C$_{1-4}$ alkyl, —(CH$_2$)$_r$—CO$_2$R$^g$, —(CH$_2$)$_r$—C$_{3-7}$ cycloalkyl, —(CH$_2$)$_r$—C$_{6-10}$ aryl, or —(CH$_2$)$_r$-5-10 membered heteroaryl, wherein said aryl or heteroaryl groups are substituted with 0-2 R$^f$;

each R$^{a1}$ is, independently at each occurrence, —(CH$_2$)$_r$-5-10 membered heteroaryl consisting of: carbon atoms and 1-4 heteroatoms selected from the group consisting of N, O, and S(O)$_p$, wherein said heteroaryl group is substituted with 0-2 R$^f$;

each R$^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-2 R$^d$, or —(CH$_2$)$^r$-5-10 membered heterocycle containing from 1-4 heteroatoms selected from the group consisting of N, O, and $S(O)_p$ and substituted with 0-2 $R^d$;

each $R^c$ is, independently at each occurrence, $C_{1-4}$ alkyl, $C_{6-10}$ aryl, 5-10 membered heteroaryl, $(C_{6-10}$ aryl$)$-$C_{1-4}$ alkyl, or (5-10 membered heteroaryl)-$C_{1-4}$ alkyl, wherein said aryl and heteroaryl groups are substituted with 0-2 $R^d$;

each $R^d$ is, independently at each occurrence, H, =O, $OR^a$, F, Cl, Br, I, CN, $NO_2$, —$NR^7R^8$, —$C(O)R^a$, —$C(O)OR^a$, —$NR^8C(O)R^a$, —$C(O)NR^{7a}R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

each $R^e$ is, independently at each occurrence, =O, $OR^a$, F, Cl, Br, I, CN, $NO_2$, —$NR^8R^9$, —$C(O)R^a$, —$C(O)OR^a$, —$NR^8C(O)R^a$, —$C(O)NR^{7a}R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

each $R^f$ is, independently at each occurrence, H, =O, $OR^g$, F, Cl, Br, I, CN, $NO_2$, —$NR^8R^9$, —$C(O)R^g$, —$C(O)OR^g$, —$NR^8C(O)R^g$, —$C(O)NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_2$-$C_6$ alkenyl, or $C_2$-$C_6$ alkynyl;

each $R^g$ is, independently at each occurrence, H, $C_{1-6}$ alkyl, or —$(CH_2)_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4.

In a third aspect, the present invention includes a compound of Formula (Ia):

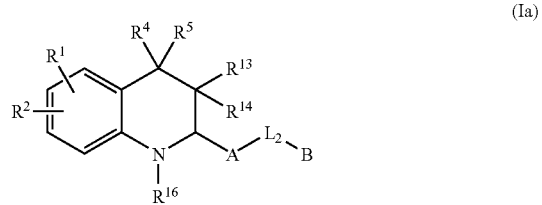

(Ia)

or a stereoisomer or a pharmaceutically acceptable salt, hydrate, or prodrug thereof, wherein:

A is phenyl substituted with 1 $R^{11c}$;

B is phenyl substituted with 0-2 $R^{11}$ and 0-1 $R^{12}$;

$R^1$ is H, —$NH_2$, —$NH(C_{1-3}$ alkyl), —$N(C_{1-3}$ alkyl$)_2$, —$C(=NH)NH_2$, —$NHC(=NH)NH_2$, —$C(O)NH_2$, —$CH_2NH_2$, —$CH_2NH(C_{1-3}$ alkyl), —$CH_2N(C_{1-3}$ alkyl$)_2$, —$CH_2CH_2NH_2$, —$CH_2CH_2NH(C_{1-3}$ alkyl), —$CH_2CH_2N(C_{1-3}$ alkyl$)_2$, —$C(=NR^8)NR^7R^9$, —$NHC(=NR^8)NR^7R^9$, —$ONHC(=NR^8)NR^7R^9$, —$NR^8CH(=NR^7)$, —$C(=NR^{8a})NR^7R^9$, —$NHC(=NR^{8a})$—$NR^7R^8$, —$C(O)NR^{7a}R^8$, —$S(O)_pNR^8R^9$, F, Cl, Br, I, $OCF_3$, $CF_3$, $OR^a$, $SR^a$, CN or $C_{1-6}$ alkyl substituted with 1 $R^{1a}$;

$R^{1a}$ is —$C(=NR^8)NR^7R^9$, —$NHC(=NR^8)NR^7R^9$, —$ONHC(=NR^8)NR^7R^9$, —$NR^8CH(=NR^7)$, —$NR^7R^8$, —$C(O)NR^{7a}R^8$, —$S(O)_pNR^8R^9$, F, $OCF_3$, $CF_3$, $OR^a$, $SR^a$, or CN;

$R^2$ is H, F, $OR^a$, CN, —$NR^7R^8$, —$C(O)NR^{7a}R^8$, —$NR^{10}C(O)R^b$, —$S(O)_pNR^8R^9$, —$S(O)R^c$, —$S(O)_2R^c$, $C_{1-6}$ alkyl substituted with 0-2 $R^{2a}$, —$(CH_2)_r$—$C_3$-$C_7$ carbocycle substituted with 0-2 $R^{2b}$, or —$(CH_2)_r$-5-7 membered heterocycle consisting of: carbon atoms and 1-4 heteroatoms selected from the group consisting of N, O, and $S(O)_p$, and substituted with 0-2 $R^{2b}$;

each $R^{2a}$ is, independently at each occurrence, H, F, $OCF_3$, $CF_3$, $OR^a$, $SR^a$, CN, —$NR^7R^8$, —$C(O)NR^{7a}R^8$, —$NR^{10}C(O)R^b$, —$S(O)_pNR^8R^9$, —$S(O)R^c$, or —$S(O)_2R^c$;

each $R^{2b}$ is, independently at each occurrence, H, F, $OR^a$, $SR^a$, CN, $NO_2$, $CF_3$, —$SO_2R^c$, —$NR^7R^8$, $C_1$-$C_6$ alkyl, $C_2$-$C_6$ alkenyl, $C_2$-$C_6$ alkynyl, $C_3$-$C_6$ cycloalkyl, $C_1$-$C_4$ haloalkyl, $C_1$-$C_4$ haloalkyloxy-, $C_1$-$C_4$ alkyloxy-, $C_1$-$C_4$ alkylthio-, $C_1$-$C_4$ alkyl-C(O)—, or $C_1$-$C_4$ alkyl-C(O)NH—;

$R^4$ is phenyl substituted with 0-3 $R^{4b}$;

each $R^{4b}$ is, independently at each occurrence, H, OH, Cl, F, Cl, Br, CN, $NO_2$, $CF_3$, —$C(O)OR^a$, —$SO_2R^c$, —$NR^7R^8$, $C_1$-$C_6$ alkyl, $C_2$-$C_6$ alkenyl, $C_2$-$C_6$ alkynyl, cycloalkyl, $C_1$-$C_4$ haloalkyl, $C_1$-$C_4$ haloalkyloxy-, $C_1$-$C_4$ alkyloxy-, $C_1$-$C_4$ alkylthio-, $C_1$-$C_4$ alkyl-C(O)—, $C_1$-$C_4$ alkyl-C(O)NH—, —$C(O)NR^{7a}R^8$, —$NR^{10}C(O)R^b$, —$NR^{10}S(O)_2NR^8R^9$, or —$S(O)_2NR^8R^9$;

$R^5$ is H, $C_1$-$C_4$ haloalkyl, or $C_1$-$C_6$ alkyl substituted with 0-2 $R^{5a}$;

each $R^7$ is, independently at each occurrence, H, $C_{1-6}$ alkyl, —$(CH_2)_n$-phenyl, $(C_{1-6}$ alkyl$)C(O)$—, $(C_{6-10}$ aryl$)$-$C_{0-4}$ alkyl-C(O)—, $(C_{3-6}$ cycloalkyl$)$-$C_{0-4}$ alkyl-C(O)—, $(C_{1-4}$ alkyl$)OC(O)$—, $(C_{6-10}$ aryl$)$-$C_{0-4}$ alkyl-OC(O)—, $(C_{1-4}$ alkyl$)$-C(O)O—$(C_{1-4}$ alkyl$)$-OC(O)—, $(C_{6-10}$ aryl$)$-C(O)O—$(C_{1-4}$ alkyl$)$-OC(O)—, $(C_{1-6}$ alkyl$)$-NHC(O)—, $(C_{6-10}$ aryl$)$-$C_{0-4}$ alkyl-NHC(O)—, $(C_{1-6}$ alkyl$)$-$S(O)_2$—, $(C_{6-10}$ aryl$)$-$(C_{0-4}$ alkyl$)$-$S(O)_2$—, $(C_{1-6}$ alkyl$)_2NC(O)$—, phenyl-NHC(O)—, benzyl-NHC(O)—, (phenyl)($C_{1-6}$ alkyl)NC(O)—, or (benzyl)($C_{1-6}$ alkyl)NC(O)—, wherein said phenyl and aryl are substituted with 0-2 $R^f$;

each $R^{7a}$ is, independently at each occurrence, H, $C_{1-4}$ alkyl substituted with 0-1 $R^{7b}$ or 0-1 $R^{7c}$, —$(CH_2)_r$—$C_{3-7}$ cycloalkyl substituted with 0-2 $R^f$, or —$(CH_2)_r$-phenyl substituted with 0-3 $R^f$;

$R^{7b}$ is =O, $OR^g$, F, Cl, Br, I, CN, $NO_2$, —$NR^7R^8$, —$C(O)R^g$, —$C(O)OR^g$, —$NR^8C(O)R^g$, —$C(O)NR^8R^9$, —$NR^8C(O)NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

$R^{7c}$ is $C_{3-10}$ carbocycle substituted with 0-3 $R^f$;

$R^{7d}$ is —$(CH_2)_r$-5-6 membered heterocycle consisting of: carbon atoms and 1-4 heteroatoms selected from the group consisting of N, O, and $S(O)_p$, and substituted 0-3 $R^f$;

each $R^8$ is, independently at each occurrence, H, $C_{1-6}$ alkyl, or —$(CH_2)_n$-phenyl;

each $R^{8a}$ is, independently at each occurrence, H, OH, $C_{1-6}$ alkyl, —$(CH_2)_n$-phenyl, $(C_{1-6}$ alkyl$)C(O)$—, $(C_{6-10}$ aryl$)$-$C_{0-4}$ alkyl-C(O)—, $(C_{3-6}$ cycloalkyl$)$-$C_{0-4}$ alkyl-C(O)—, $(C_{1-4}$ alkyl$)OC(O)$—, $(C_{6-10}$ aryl$)$-$C_{0-4}$ alkyl-OC(O)—, $(C_{1-4}$ alkyl$)$-C(O)O—$(C_{1-4}$ alkyl$)$-OC(O)—, $(C_{6-10}$ aryl$)$-C(O)O—$(C_{1-4}$ alkyl$)$-OC(O)—, $(C_{1-6}$ alkyl$)$-NHC(O)—, $(C_{6-10}$ aryl$)$-$C_{0-4}$ alkyl-NHC(O)—, $(C_{1-6}$ alkyl$)$-$S(O)_2$—, $(C_{6-10}$ aryl$)$-$(C_{0-4}$ alkyl$)$-$S(O)_2$—, $C_{1-4}$ alkoxy, $(C_{1-4}$ alkyl$)C(O)O$—, or $(C_{6-10}$ aryl$)$-$(C_{0-4}$ alkyl$)$-C(O)O—; wherein said phenyl and aryl are substituted with 0-2 $R^f$;

each $R^9$ is, independently at each occurrence, H, $C_{1-6}$ alkyl, or —$(CH_2)_n$-phenyl;

each $R^{10}$ is, independently at each occurrence, H, $C_{1-6}$ alkyl substituted with 0-2 $R^{10a}$, $C_{2-6}$ alkenyl substituted with 0-2 $R^{10a}$, $C_{2-6}$ alkynyl substituted with 0-2 $R^{10a}$, $(C_{1-6}$ alkyl$)C(O)$—, $(C_{3-6}$ cycloalkyl$)C_{1-3}$ alkyl-C(O)—, $(C_{3-6}$ cycloalkyl$)C(O)$—, phenyl-C(O)—, benzyl-C(O)—, benzyl-$S(O)_2$—, $(C_{1-6}$ alkyl$)NHC(O)$—, $(C_{1-6}$ alkyl$)_2NC(O)$—, phenyl-NHC(O)—, benzyl-NHC(O)—, (phenyl)($C_{1-6}$ alkyl)NC(O)—, (benzyl)($C_{1-6}$ alkyl)NC(O)—, ($C_{1-6}$ alkyl)-S(O)$_2$—, phenyl-S(O)$_2$—, or —(CH$_2$)$_r$—C$_{3-10}$ carbocycle substituted with 0-3 $R^d$;

each $R^{10a}$ is, independently at each occurrence, H, $C_{1-4}$ alkyl, OR$^a$, Cl, F, Cl, Br, I, =O, CF$_3$, CN, NO$_2$, —C(O)R$^a$, —C(O)OR$^a$, —C(O)NR$^{7a}$R$^8$, or —S(O)$_p$R$^c$;

each $R^{11}$ is, independently at each occurrence, H, =O, —(CH$_2$)$_r$—OR$^a$, F, Cl, Br, I, CN, NO$_2$, —(CH$_2$)$_r$—NR$^7$R$^8$, —C(O)R$^a$, —C(O)OR$^a$, —NR$^8$C(O)R$^a$, —NR$^8$C(O)OR$^a$, —C(O)NR$^{7a}$R$^8$, —NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, $C_{1-6}$ alkyl substituted with 0-2 $R^{11a}$, $C_{2-6}$ alkenyl substituted with 0-2 $R^{11a}$, $C_{2-6}$ alkynyl substituted with 0-2 $R^{11a}$, $C_{1-6}$ alkyl substituted with 0-2 $R^{11b}$, $C_{2-6}$ alkenyl substituted with 0-2 $R^{11b}$, or $C_{2-6}$ alkynyl substituted with 0-2 $R^{11b}$;

each $R^{11a}$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^a$, —C(O)NR$^{7a}$R$^8$, —NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each $R^{11b}$ is, independently at each occurrence, a 5-12 membered heterocycle consisting of: carbon atoms and 1-4 heteroatoms selected from the group consisting of N, O, and S(O)$_p$, and substituted 0-3 $R^d$;

$R^{11c}$ is —C(O)R$^{a1}$, —C(O)OR$^{a1}$, —NR$^8$C(O)R$^{a1}$, —NR$^8$C(O)OR$^{a1}$, —C(O)NR$^{7a}$R$^8$, $C_{1-6}$ alkyl substituted with 1 $R^{11d}$, $C_{2-6}$ alkenyl substituted with 1 $R^{11d}$, or $C_{2-6}$ alkynyl substituted with 1 $R^{11d}$;

each $R^{11d}$ is, independently at each occurrence, a 5-12 membered heterocycle consisting of: carbon atoms and 1-4 heteroatoms selected from the group consisting of N, O, and S(O)$_p$, and substituted 0-3 $R^d$;

each $R^{12}$ is, independently at each occurrence, OR$^{12a}$, —C(O)NR$^{7a}$R$^8$, —(CH$_2$)$_r$CO$_2$R$^{12a}$, —(CH$_2$)$_r$SO$_3$H, —OSO$_3$H, —(CH$_2$)$_r$PO$_3$H, —OPO$_3$H$_2$, —PO$_3$H$_2$, —NHPO$_3$H$_2$, —NHCOCF$_3$, —NHSO$_2$CF$_3$, —CONHNHSO$_2$CF$_3$, —C(CF$_3$)$_2$OH, —SO$_2$NHR$^{12a}$, —CONHSO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, —CONHOR$^{12b}$,

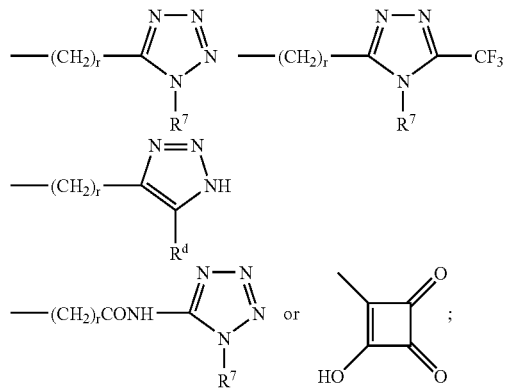

each $R^{12a}$ is, independently at each occurrence, H, $C_{1-6}$ alkyl, —(CH$_2$)$_r$—C$_{3-10}$ carbocycle substituted with 0-3 $R^d$; or —(CH$_2$)$_r$-5-10 membered heterocycle consisting of carbon atoms and 1-4 heteroatoms selected from the group consisting of N, O, and S(O)$_p$, and substituted with 0-3 $R^d$;

each $R^{12b}$ is, independently at each occurrence, $C_1$-$C_6$ alkyl substituted with 0-2 $R^{12c}$, $C_2$-$C_6$ alkenyl substituted with 0-2 $R^{12c}$, $C_2$-$C_6$ alkynyl substituted with 0-2 $R^{12c}$, —(CH$_2$)$_r$—C$_3$-C$_{10}$ carbocycle substituted with 0-3 $R^{12c}$, or —(CH$_2$)$_r$-5-10 membered heterocycle consisting of: carbon atoms and 1-4 heteroatoms selected from the group consisting of N, O, and S(O)$_p$, and substituted with 0-3 $R^{12c}$;

each $R^{12c}$ is, independently at each occurrence, H, F, Cl, Br, I, CF$_3$, OCF$_3$, CN, NO$_2$, OR$^a$, —CO$_2$R$^a$, —NR$^7$R$^8$, —SO$_2$R$^c$, $C_1$-$C_6$ alkyl, $C_2$-$C_6$ alkenyl, $C_2$-$C_6$ alkynyl, —(CH$_2$)$_r$—C$_{3-10}$ carbocycle substituted with 0-3 $R^d$; or —(CH$_2$)$_r$-5-10 membered heterocycle consisting of carbon atoms and 1-4 heteroatoms selected from the group consisting of N, O, and S(O)$_p$, and substituted with 0-3 $R^d$;

$R^{13}$ is H or $C_{1-4}$ alkyl;

$R^{14}$ is H or $C_{1-4}$ alkyl;

$R^{1-6}$ is H, $C_{1-4}$ alkyl, benzyl, $C_{1-4}$ alkyl-C(O)—, $C_{1-4}$ alkyl-S(O)$_2$—, or $C_{1-4}$ alkyl-OC(O)—;

each $R^a$ is, independently at each occurrence, H, $C_{1-4}$ alkyl, —(CH$_2$)$_r$—CO$_2$R$^g$, —(CH$_2$)$_r$—C$_{3-7}$ cycloalkyl, —(CH$_2$)$_r$—C$_{6-10}$ aryl, or —(CH$_2$)$_r$-5-10 membered heteroaryl, wherein said aryl or heteroaryl groups are substituted with 0-2 $R^f$;

each $R^{a1}$ is, independently at each occurrence, —(CH$_2$)$_r$-5-10 membered heteroaryl consisting of: carbon atoms and 1-4 heteroatoms selected from the group consisting of N, O, and S(O)$_p$, wherein said heteroaryl group is substituted with 0-2 $R^f$;

each $R^b$ is, independently at each occurrence, CF$_3$, OH, $C_{1-4}$ alkoxy, $C_{1-6}$ alkyl, —(CH$_2$)$_r$—C$_{3-10}$ carbocycle substituted with 0-2 $R^d$, or —(CH$_2$)$_r$-5-10 membered heterocycle containing from 1-4 heteroatoms selected from the group consisting of N, O, and S(O)$_p$ and substituted with 0-2 $R^d$;

each $R^c$ is, independently at each occurrence, $C_{1-4}$ alkyl, $C_{6-10}$ aryl, 5-10 membered heteroaryl, ($C_{6-10}$ aryl)-$C_{1-4}$ alkyl, or (5-10 membered heteroaryl)-$C_{1-4}$ alkyl, wherein said aryl and heteroaryl groups are substituted with 0-2 $R^d$;

each $R^d$ is, independently at each occurrence, H, =O, OR$^a$, F, Cl, Br, I, CN, NO$_2$, —NR$^7$R$^8$, —C(O)R$^a$, —C(O)OR$^a$, —NR$^8$C(O)R$^a$, —C(O)NR$^{7a}$R$^8$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, $C_1$-$C_6$ alkyl substituted with 0-2 $R^e$, $C_2$-$C_6$ alkenyl substituted with 0-2 $R^e$, or $C_2$-$C_6$ alkynyl substituted with 0-2 $R^e$;

each $R^e$ is, independently at each occurrence, =O, OR$^a$, F, Cl, Br, I, CN, NO$_2$, —NR$^8$R$^9$, —C(O)R$^a$, —C(O)OR$^a$, —NR$^8$C(O)R$^a$, —C(O)NR$^{7a}$R$^8$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each $R^f$ is, independently at each occurrence, H, =O, OR$^g$, F, Cl. Br, I, CN, NO$_2$, —NR$^8$R$^9$, —C(O)R$^g$, —C(O)OR$^g$, —NR$^8$C(O)R$^g$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, $C_{1-6}$ alkyl, $C_2$-$C_6$ alkenyl, or $C_2$-$C_6$ alkynyl;

each $R^g$ is, independently at each occurrence, H, $C_{1-6}$ alkyl, or —(CH$_2$)$_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4.

In a fourth aspect, the present invention includes a compound of Formula (Ib):

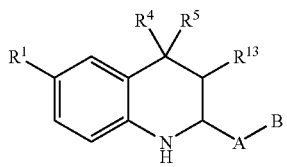

or a stereoisomer or a pharmaceutically acceptable salt hydrate, or prodrug thereof, wherein:

B is phenyl substituted with 0-2 $R^{11}$ and 0-1 $R^{12}$;

$R^1$ is H, F, Cl, —C(=NH)NH$_2$, —CH$_2$NH$_2$, —C(O)NR$^{7a}$R$^8$, OMe, or CN;

$R^4$ is phenyl substituted with 0-3 $R^{4b}$;

each $R^{4b}$ is, independently at each occurrence, H, OH, Cl, F, Cl, Br, CN, NO$_2$, CF$_3$, —C(O)OR$^a$, —SO$_2$R$^c$, —NR$^7$R$^8$, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_1$-$C_4$ haloalkyloxy-, $C_1$-$C_4$ alkyloxy-, $C_1$-$C_4$ alkylthio-, $C_1$-$C_4$ alkyl-C(O)—, or $C_1$-$C_4$ alkyl-C(O)NH—;

$R^5$ is H or $C_1$-$C_3$ alkyl;

each $R^7$ is, independently at each occurrence, H, $C_{1-6}$ alkyl, or benzyl;

each $R^{7a}$ is, independently at each occurrence, H, $C_{1-4}$ alkyl substituted with 0-1 $R^{7b}$ or 0-1 $R^{7c}$, —(CH$_2$)$_r$—$C_{3-7}$ cycloalkyl substituted with 0-1 $R^f$, or —(CH$_2$)$_r$-phenyl substituted with 0-2 $R^f$;

$R^{7b}$ is OR$^g$, F, CN, —NR$^7$R$^8$, —C(O)R$^g$, —C(O)OR$^g$, —NR$^8$C(O)R$^g$, —C(O)NR$^8$R$^9$, —SO$_2$NR$^8$R$^9$, or —NR$^8$SO$_2$—$C_{1-4}$ alkyl;

$R^{7c}$ is $C_{3-7}$ cycloalkyl substituted with 0-1 $R^f$, phenyl substituted with 0-2 $R^f$, or a 5-6 membered heterocycle consisting of: carbon atoms and 1-4 heteroatoms selected from the group consisting of N, O, and S(O)$_p$, and substituted 0-2 $R^f$;

$R^{7d}$ is —(CH$_2$)$_r$-5-6 membered heterocycle consisting of: carbon atoms and 1-4 heteroatoms selected from the group consisting of N, O, and S(O)$_p$, and substituted 0-2 $R^f$;

each $R^8$ is, independently at each occurrence, H, $C_{1-6}$ alkyl, or benzyl;

each $R^9$ is, independently at each occurrence, H, $C_{1-6}$ alkyl, or benzyl;

each $R^{11}$ is, independently at each occurrence, H, F, —(CH$_2$)$_r$—OR$^a$, CN, —(CH$_2$)$_r$—NR$^7$R$^8$, —C(O)OR$^a$, —NR$^8$C(O)R$^a$, —NR$^8$C(O)OR$^a$, —C(O)NR$^{7a}$R$^8$, —NR$^8$C(O)NR$^8$R$^9$, —SO$_2$NR$^8$R$^9$, or —NR$^8$SO$_2$—$C_{1-4}$ alkyl;

$R^{11c}$ is —C(O)R$^{a1}$, —C(O)OR$^{a1}$, —NR$^8$C(O)R$^{a1}$, —NR$^8$C(O)OR$^{a1}$, —C(O)NR$^{7d}$R$^8$, $C_{1-6}$ alkyl substituted with 1 $R^{11d}$, $C_{2-6}$ alkenyl substituted with 1 $R^{11d}$, or $C_{2-6}$ alkynyl substituted with 1 $R^{11d}$;

each $R^{11d}$ is, independently at each occurrence, a heterocycle substituted 0-3 $R^d$ and selected from the group: tetrazolyl, imidazolyl, thiazolyl, oxazolyl, isoxazolyl, triazolyl, pyrazolyl, thienyl, thiadiazolyl, oxadiazolyl, pyridinyl, pyrimidinyl, pyrazinyl, pyridazinyl, tetrahydropyranyl, morpholinyl, piperidinyl, piperazinyl, and pyrrolidinyl;

$R^{12}$ is —C(O)NR$^{7a}$R$^8$, —(CH$_2$)$_r$CO$_2$R$^{12a}$, —SO$_2$NHR$^{12a}$, —CONHSO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, —CONHSO$_2$R$^{12b}$, —CONHOR$^{12b}$, or —(CH$_2$)$_r$-5-tetrazolyl-;

each $R^{12a}$ is, independently at each occurrence, H or $C_{1-6}$ alkyl;

each $R^{12b}$ is, independently at each occurrence, $C_1$-$C_4$ alkyl substituted with 0-1 $R^{12c}$, $C_2$-$C_4$ alkenyl substituted with 0-1 $R^{12c}$, $C_2$-$C_4$ alkynyl substituted with 0-1 $R^{2c}$, —(CH$_2$)$_r$—$C_3$-$C_7$ carbocycle substituted with 0-2 $R^{12c}$, or —(CH$_2$)$_r$-5-6 membered heterocycle consisting of: carbon atoms and 1-4 heteroatoms selected from the group consisting of N, O, and S(O)$_p$, and substituted with 0-2 $R^{12c}$;

each $R^{12c}$ is, independently at each occurrence, H, F, Cl, Br, I, CF$_3$, OCF$_3$, CN, NO$_2$, OR$^a$, —CO$_2$R$^a$, —NR$^7$R$^8$, —SO$_2$R$^c$, $C_{1-6}$ alkyl, $C_2$-$C_6$ alkenyl, $C_2$-$C_6$ alkynyl, —(CH$_2$)$_r$—$C_{3-10}$ carbocycle substituted with 0-3 $R^d$; or —(CH$_2$)$_r$-5-10 membered heterocycle consisting of carbon atoms and 1-4 heteroatoms selected from the group consisting of N, O, and S(O)$_p$, and substituted with 0-3 $R^d$;

$R^{13}$ is H or $C_1$-$C_4$ alkyl;

each $R^a$ is, independently at each occurrence, H, $C_{1-4}$ alkyl, —(CH$_2$)$_r$—CO$_2$R$^g$, —(CH$_2$)$_r$—$C_{3-7}$ cycloalkyl, or —(CH$_2$)$_r$—$C_{6-10}$ aryl;

each $R^{a1}$ is, independently at each occurrence, a heteroaryl substituted with 0-2 $R^f$ and selected from the group: tetrazolyl, imidazolyl, thiazolyl, thienyl, oxazolyl, isoxazolyl, triazolyl, pyrazolyl, thiadiazolyl, oxadiazolyl, pyridinyl, pyrimidinyl, pyrazinyl, pyridazinyl, and triazinyl;

each $R^f$ is, independently at each occurrence, H, =O, OR$^g$, F, Cl, Br, CF$_3$, CN, NO$_2$, —NR$^8$R$^9$, —C(O)R$^g$, —C(O)OR$^g$, —NR$^8$C(O)R$^g$, —C(O)NR$^8$R$^9$, —SO$_2$NR$^8$R$^9$, —NR$^8$SO$_2$—$C_{1-4}$ alkyl, —NR$^8$SO$_2$CF$_3$, —S(O)$_2$CF$_3$, —S(O)$_p$—$C_{1-4}$ alkyl, $C_1$-$C_6$ alkyl, $C_2$-$C_6$ alkenyl, or $C_2$-$C_6$ alkynyl;

each $R^g$ is, independently at each occurrence, H or $C_{1-4}$ alkyl;

p, at each occurrence, is selected from 0, 1, and 2; and r, at each occurrence, is selected from 0, 1, 2, 3, and 4.

In a fifth aspect, the present invention includes compounds of Formula (Ib) or a stereoisomer or pharmaceutically acceptable salts, hydrates, or prodrugs thereof, wherein:

B is phenyl substituted with 0-2 $R^{11}$ and 0-1 $R^{12}$;

$R^1$ is —C(=NH)NH$_2$, —C(=O)NH$_2$, —CH$_2$NH$_2$, or OMe;

$R^4$ is phenyl substituted with 0-1 $R^{4b}$;

$R^{4b}$ is H, OH, or F;

$R^5$ is H, Me, Et, or Pr;

each $R^{11}$ is, independently at each occurrence, H, F, OH, OMe, CN, —NH$_2$, —CH$_2$OH, —CO$_2$H, —CO$_2$Me, —NHCOMe, —NHCOEt, —NHCOPr, —NHCO(i-Pr), —NHCO(i-Bu), —NHCO(cyclopropyl), —NHCO(phenyl), —NHCO(2-CO$_2$H-phenyl), —NHCO(3-CO$_2$H-phenyl), —NHCO(4-CO$_2$H-phenyl), —NHCO(3,5-(CO$_2$H)$_2$-phenyl)-, —NHCO(3,5-(CF$_3$)$_2$-phenyl), —NHCO(3-Me-5-CO$_2$H-phenyl), —NHCO(3-(t-Bu)-5-CO$_2$H-phenyl), —NHCO(3-CONH$_2$-5-CO$_2$H-phenyl), —NHCO(3-NH$_2$-5-CO$_2$H-phenyl), —NHCO(benzyl), —NHCO(phenethyl), —NHCO(phenylpropyl), —NHCO[2-(2-pyridyl)-ethyl], —NHCO(tetrazol-5-yl), —NHCOCH$_2$(tetrazol-5-yl), —NHCO(CH$_2$)$_2$(tetrazol-5-yl), —CONH$_2$, —CONHMe, —CONH(i-Pr), —CONH(i-Bu), —CONH(t-Bu), —CONH(benzyl), —CONH(phenethyl), —CONH(phenylpropyl), —CONH[2-(2-pyridyl)-ethyl], —NHCONHMe, —NHCONHEt, —NHCH$_2$CO$_2$H, —NHCOCO$_2$H, —NHCOCH$_2$CO$_2$H, —NHCO(CH$_2$)$_2$CO$_2$H, —NHCO(CH$_2$)$_3$CO$_2$H, —NHSO$_2$Me, —NHSO$_2$Et, or —CH$_2$NMe$_2$;

$R^{12}$ is —CO$_2$H, —CH$_2$(CO$_2$H), —CO$_2$Me, —SO$_2$NH$_2$, or —CONH$_2$;

$R^{13}$ is H or Me; and provided ring A is not substituted ortho to its attachment to the tetrahydroquinoline with OH, —CO$_2$H, —CO$_2$Me, —NH$_2$, or —NHSO$_2$C$_{1-4}$ alkyl.

In a sixth aspect, the present invention includes compounds of Formula (Ib) or a stereoisomer or pharmaceutically acceptable salts, hydrates, or prodrugs thereof, wherein:

A is 5-NHCO(tetrazol-5-yl)-1,3-phenylene, 5-NHCOCH$_2$(tetrazol-5-yl)-1,3-phenylene, or 5-NHCO(CH$_2$)$_2$(tetrazol-5-yl)-1,3-phenylene;

B is 2-CO$_2$H-phenyl, 4-CO$_2$H-phenyl, 2-SO$_2$NH$_2$-phenyl, 3-CH$_2$(CO$_2$H)-phenyl, 2,4-(CO$_2$H)$_2$-phenyl, 2,4-(CO$_2$Me)$_2$-phenyl, 2,4-(CONH$_2$)$_2$-phenyl, 2-CO$_2$H-4-CO$_2$Me-phenyl, 2-CO$_2$H-4-NH$_2$-phenyl, 2-CO$_2$H-4-CN-phenyl, 2-CO$_2$H-4-OMe-phenyl, 2-CO$_2$H-4-NHAc-phenyl, 2-CO$_2$H-4-CONH$_2$-phenyl, 2-CO$_2$H-4-CONH(i-Pr)-phenyl, 2-CO$_2$H-4-C(O)NH(i-Bu)-phenyl, 2-CO$_2$H-4-C(O)NH(t-Bu)-phenyl, 2-CO$_2$H-4-NHCOMe-phenyl, 2-CO$_2$H-4-NHCONHMe-phenyl, 2-CO$_2$H-4-CH$_2$NMe$_2$-phenyl, or 2-CO$_2$H-4-NHSO$_2$Me-phenyl;

$R^1$ is —C(=NH)NH$_2$, —C(=O)NH$_2$, —CH$_2$NH$_2$, or OMe;

$R^4$ is phenyl, 4-OH-phenyl or 4-F-phenyl;

$R^5$ is H, Me, Et, or Pr; and $R^{13}$ is H or Me.

In a seventh aspect, the present invention provides a compound selected from:

3'-(6-carbamimidoyl-4-methyl-4-phenyl-1,2,3,4-tetrahydroquinolin-2-yl)-4-carbamoyl-5'-[(5-tetrazolyl)methylcarbonylamino]-biphenyl-2-carboxylic acid;

3'-(6-carbamimidoyl-4-methyl-4-phenyl-1,2,3,4-tetrahydroquinolin-2-yl)-4-carbamoyl-5'-[(5-tetrazoyl)carbonylamino]-biphenyl-2-carboxylic acid; and 3'-(6-carbamimidoyl-4-methyl-4-phenyl-1,2,3,4-tetrahydroquinolin-2-yl)-4-carbamoyl-5'-[2-(5-tetrazolyl)ethylcarbonylamino]-biphenyl-2-carboxylic acid;

or a stereoisomer or a pharmaceutically acceptable salt, hydrate, or prodrug thereof.

In another embodiment, the present invention provides a novel pharmaceutical composition, comprising: a pharmaceutically acceptable carrier and a therapeutically effective amount of a compound of the present invention or a stereoisomer or a pharmaceutically acceptable salt or prodrug form thereof.

In another embodiment the present invention provides a method for modulation of the coagulation cascade and/or contact activation system comprising administering to a patient in need of such treatment a therapeutically effective amount of at least one of the compounds of the present invention or a pharmaceutically acceptable salt or prodrug form thereof.

In another embodiment, the present invention provides a method for treating thromboembolic disorders comprising: administering to a patient in need of such treatment a therapeutically effective amount of at least one of the compounds of the present invention or a pharmaceutically acceptable salt or prodrug form thereof.

In another embodiment, the present invention provides a method, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the present invention provides a method, wherein the thromboembolic disorder disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a pharmaceutically acceptable salt or prodrug form thereof.

In another embodiment, the present invention provides a method, wherein the inflammatory disorder is selected from the group consisting of sepsis, acute respiratory dystress syndrome, and systemic inflammatory response syndrome.

In another embodiment, the present invention provides a method of treating a patient in need of thromboembolic disorder treatment, comprising: administering a compound of the present invention or a pharmaceutically acceptable salt form thereof in an amount effective to treat a thromboembolic disorder.

In another embodiment, the present invention provides a method of treating a patient in need of inflammatory disorder treatment, comprising: administering a compound of the present invention or a pharmaceutically acceptable salt form thereof in an amount effective to treat an inflammatory disorder.

In another embodiment, the present invention provides a pharmaceutical composition further comprising at least one additional herapeutic agent selected from one or more of potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning.

In a preferred embodiment, the present invention provides a pharmaceutical composition wherein the at least one additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, or an antithrombotic agent selected from anticoagulants selected from thrombin inhibitors, other factor XIa inhibitors, other plasma kallikrein inhibitors, factor VIIa inhibitors and factor Xa inhibitors, and antiplatelet agents selected from GPIIb/IIIa blockers, P2Y$_1$ and P2Y$_{12}$ antagonists, thromboxane receptor antagonists, and aspirin.

In a preferred embodiment, the present invention provides a pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent clopidogrel.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used for the treatment of a thromboembolic and/or inflammatory disorder.

In another preferred embodiment, the present invention provides a novel article of manufacture, further comprising:
(d) a second container;

wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat a thromboembolic and/or inflammatory disorder.

In another preferred embodiment, the present invention provides a novel article of manufacture, further comprising:
(d) a second container;

wherein components (a) and (b) are located within the second container and component (c) is located within or outside of the second container.

In another embodiment, the present invention provides a novel method, comprising: administering a compound of the present invention or a pharmaceutically acceptable salt form thereof in an amount effective to treat a thromboembolic and/or inflammatory disorder.

In another embodiment, the present invention provides a compound of the present invention for use in therapy.

In another embodiment, the present invention also provides the use of a compound of the present invention for the manufacture of a medicament for the treatment of a thromboembolic and/or inflammatory disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Accordingly, the present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_1$-$C_{10}$ alkyl" (or alkylene), is intended to include $C_1$, $C_2$, $C_3$, $C_4$, $C_5$, $C_6$, $C_7$, $C_8$, $C^9$, and $C^{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_2$-$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_2$-$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo. "Haloalkyl" refers to branched and straight-chained, having one or more halogen substituents. Example haloalkyl groups include, but are not limited to, $CF_3$, $C_2F_5$, $CHF_2$, $CCl_3$, $CHCl_2$, $C_2Cl_5$, and the like.

The term "alkoxy" or "alkyloxy" refers to an —O-alkyl group. "$C_1$-$C_6$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulphur bridge; for example methyl-S—, ethyl-S—, and the like.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, and sulfate.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When any variable (e.g., $R^{2a}$, $R^{2b}$, etc.) occurs more than one time in any constituent or formula for a compound, its definition at each occurrence is independent of its definition at every other occurrence. Thus, for example, if a group is shown to be substituted with 0-3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to acid or base salts of the compounds described herein. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety. Examples of pharmaceutically acceptable salts include, but are not limited to, mineral or organic acid salts of basic residues such as amines; alkali or organic salts of acidic residues such as carboxylic acids; and the like.

Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Prodrugs" refer to inactive compounds that can be converted upon absorption by a mammalian subject to an active compound of the present invention. Prodrugs of the compounds of the present invention can be prepared by modifying functional groups present in the compounds of the present invention in such a way that the modifications are cleaved in vivo to produce the parent compounds. Examples of prodrugs include, but are not limited to, acetate, formate and benzoate derivatives of alcohol and amine functional groups in the compounds of the present invention. Preparation of prodrugs is well known in the art and described in, for example, *Medicinal Chemistry: Principles and Practice*, ed. F. D. King, The Royal Society of Chemistry, Cambridge, UK, 1994, which is incorporated herein by reference in its entirety.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa and/or plasma kallikrein. "Therapeutically effective amount" is also intended to include an amount of the combination of compounds claimed that is effective to inhibit factor XIa and/or plasma kallikrein. The combination of compounds is preferably a synergistic combination. Synergy, as described, for example, by Chou and Talalay, *Adv. Enzyme Regul.* 1984, 22:27-55, occurs when the effect (in this case, inhibition of factor XIa and/or plasma kallikrein) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1999).

All references cited herein are hereby incorporated in their entirety herein by reference.

Standard Procedure for Tetrahydroquinoline Synthesis:

The tetrahydroquinoline moieties, THQ, of the present invention can be constructed according to the general method outlined in Scheme 1. An aniline, A, or salt thereof, is suspended in a suitable solvent, such as acetonitrile. The suspension is treated with a suitably substituted aldehyde, B, and a suitably substituted olefin, C, in stochiometric proportions. A catalyst, such as indium triflate or scandium triflate, is added and the reaction is allowed to react at temperatures ranging from room temperature to 70° C. Reaction times vary from a few hours to 48 hours. The desired products are purified using chromatography.

Scheme 1

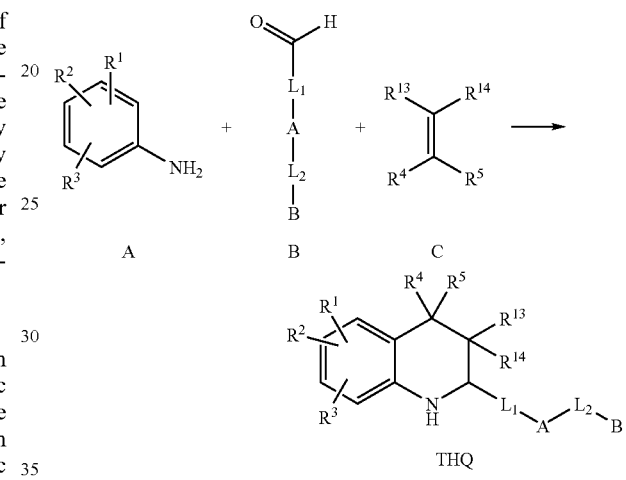

For example, as shown in Scheme 2, a suitably substituted aniline, such as 4-aminobenzamidine mono HCl salt, is suspended in acetonitrile. The suspension is treated with a suitably substituted aldehyde, such as 4-acetoxy-3-methoxybenzaldehyde and a suitably substituted olefin, such as 4-vinylphenol, in stochiometric proportions. A catalyst such as indium triflate or scandium triflate is added and the reaction is allowed to react at temperatures ranging from room temperature to 70° C. Reaction times vary from few hours to 48 hours. The desired product is purified using reverse phase chromatography to provide THQ1. Alternately, 4-aminobenzonitrile can be used instead of 4-aminobenzamidine in this reaction. This enables further modifications at other parts of the molecule to introduce other alternate functionalities as described in the scope of the invention. The cyano group can be subsequently converted to the corresponding benzamidine by various methods known in the art, for example using a Pinner reaction.

Scheme 2

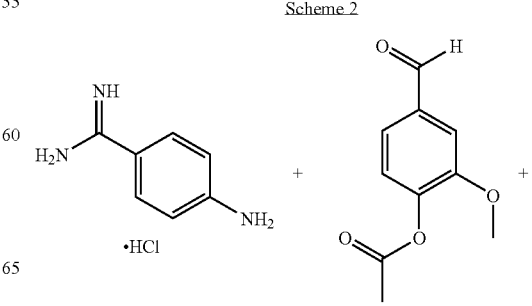

-continued

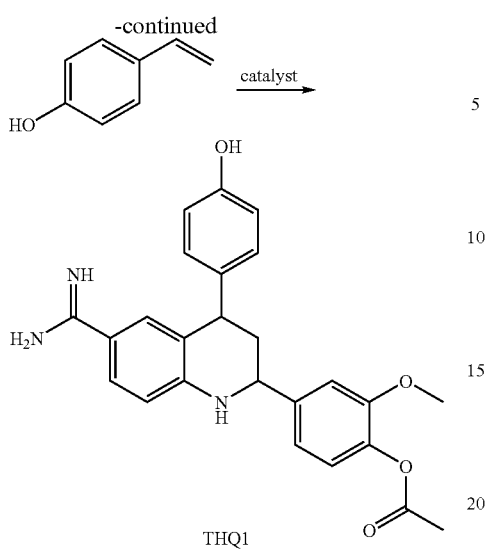

THQ1

Using similar methodology as is outlined in Scheme 2, additional compounds of the invention wherein the amidine group is replaced by a benzyl amine can be prepared from protected amines, for example 4-N-Boc-aminomethylphenyl amine, may be used in place of 4-aminobenzamidine to construct THQ2 compounds of this invention, that incorporate a protected aminomethyl function onto the tetrahydroquinoline ring system (Scheme 3). The R' and R'' groups can then be further modified to provide additional compounds within the scope of the present invention. Other benzamidine mimics can be prepared using the methods described in U.S. Pat. No. 6,339,099 and U.S. Pat. No. 6,413,980, the disclosures of which are hereby incorporated by reference in their entirety.

Scheme 3

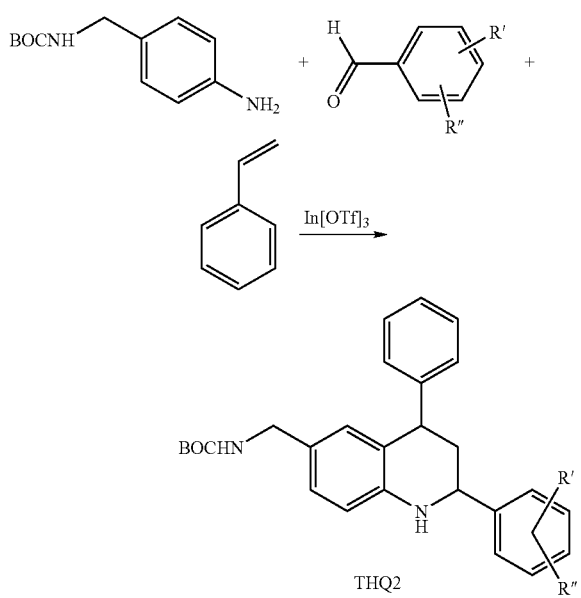

THQ2

The basic reaction for the synthesis of the compounds of formula THQ requires three components: an aryl amine, A, an aldehyde, B, and an olefin, C. When the desired inputs for the reaction are not commercially available, they can be synthesized according to the methods described below and/or methods readily known to one skilled in the art of organic synthesis.

Synthesis of Aryl Amines A:

Non-commercial aryl amines of general formula A may be readily accessed from reduction of the corresponding nitro aromatics as depicted in Scheme 4 using any of the methods known in the art for reducing aromatic nitro groups to the corresponding anilines, for example, tin(II)chloride, catalytic hydrogenation, sodium dithionite, etc. (see "*Advanced Organic Chemistry*" Jerry March, Wiley Interscience p. 1103 and references therein).

Scheme 4

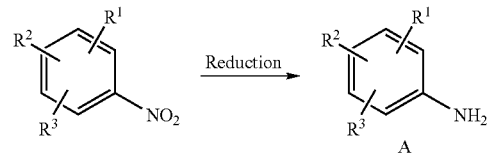

Synthesis of Substituted Aldehydes:

Aldehydes of the general formula B are accessible from a variety of straightforward chemical transformations known to one skilled in the art. As outlined in Scheme 5, aldehydes suitable for use in preparing compounds of this invention may be obtained through oxidation of the corresponding alcohols or halides as taught in "*Advanced Organic Chemistry*" (Jerry March, Wiley Interscience pp 1057-60 and p. 1081 and references therein). Alternatively aldehydes B may be prepared by hydrogenation of the corresponding carboxylic acid (Scheme 5, R=H) in the presence of palladium complexes and pivalic anhydride (Nagayama et al. *Chemistry Letters* 1998, 27, 1143-1144) or by reduction of an ester (R=alkyl) with DIBAL-H (Chandrasekhar et al. *Tetrahedron Letters* 1998, 39, 909-910).

Scheme 5

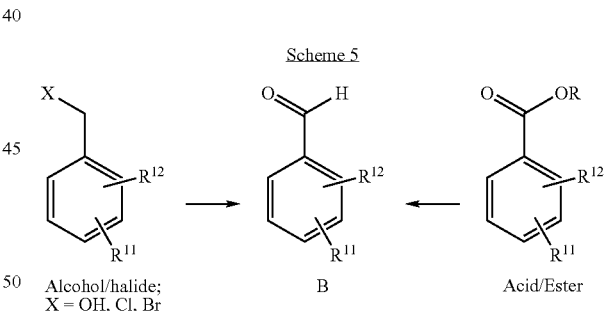

Alcohol/halide;   B   Acid/Ester
X = OH, Cl, Br

Additional aldehydes of general Formulae (III), (IV) and (V) suitable for the synthesis of the THQ compounds of the present invention may be prepared according to one or more of the methods described for the examples shown below.

(III)

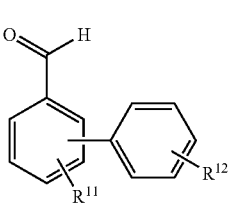

-continued

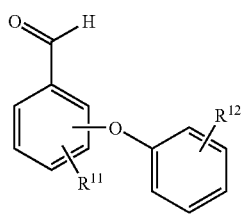
(IV)

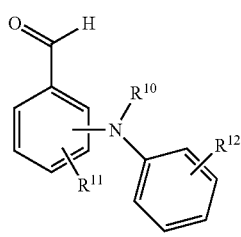
(V)

Aryl-substituted aldehyde intermediates of general Formulae (III) may be prepared as outlined in Scheme 6. It is appreciated that one skilled in the art could readily apply the methods described below to make additional substituted biphenyl aldehydes of Formula (III). In this approach, a suitably substituted aryl bromide is either commercially available or is prepared through electorphilic bromination of the corresponding benzaldehyde. The resulting bromide can then serve as a common intermediate for the preparation of bi-aryl aldehydes through metal mediated cross coupling reactions of the type described by Fu et al. (*J. Amer. Chem. Soc.* 2000, 122, 4020-4028).

In the example shown in Scheme 6, 4-acetoxy-2-bromo-3-methoxybenzaldehyde, 1, is treated with a brominating reagent, such as $Br_2$, in a suitable solvent, such as $CCl_4$, to provide the corresponding bromide, 2. Suzuki coupling between 2 and a suitably substituted boronic acid, such as commercially available 2-carboxyphenylboronic acid yields the 2-carboxy substituted biphenyl (3, R=H) that may be used directly in Scheme 1 above as component B for the synthesis of additional THQ compounds of the present invention. In cases where R is alkyl, an intermediate deprotection step using alkali base may be utilized to generate the desired acid substituted biphenyl.

Scheme 6

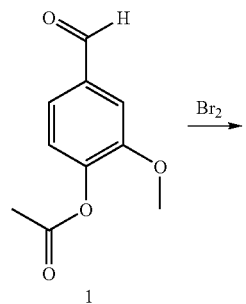

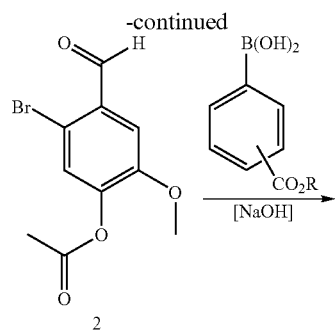

In cases where suitable boronic acids are not commercially available, a modification to this approach may be adopted as is outlined in Scheme 6a. In this case the aryl bromide intermediate, for example, 4-acetoxy-2-bromo-3-methoxybenzaldehyde 3, is subjected to a palladium mediated coupling with a diboron species such as bis(pinacolato)diboron to provide a 4,4,5,5-tetramethyl-[1,3,2]dioxaborolane intermediate, in this example, 4-hydroxy-5-methoxy-2-(4,4,5,5-tetramethyl-[1,3,2]dioxaborolan-2-yl)-benzaldehyde 4. (see *J. Am. Chem. Soc.* 2000, 122 (36), 8717-8727). Alternately, this same intermediate can be prepared by reaction of the intermediate bromide with pinacolborane in the presence of a palladium catalyst (*Synthesis*, 2002, 9, 1163-1170).

Scheme 6a

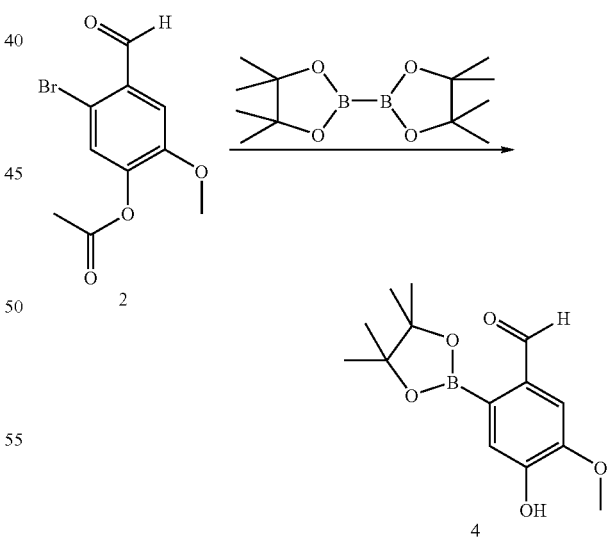

Intermediate pinacolate 4 can be used as a precursor for the synthesis of additional substituted aldehydes of Formula (III) through Pd-catalyzed coupling with suitably substituted aryl bromides, iodides or triflates. For example, as outlined in Scheme 6b, coupling of compound 4 with 4-bromobenzene sulfonamide 5 provides a biphenyl sulfonamide 6 which can be used as component B in Scheme 1 above to provide additional examples of the invention.

Scheme 6b

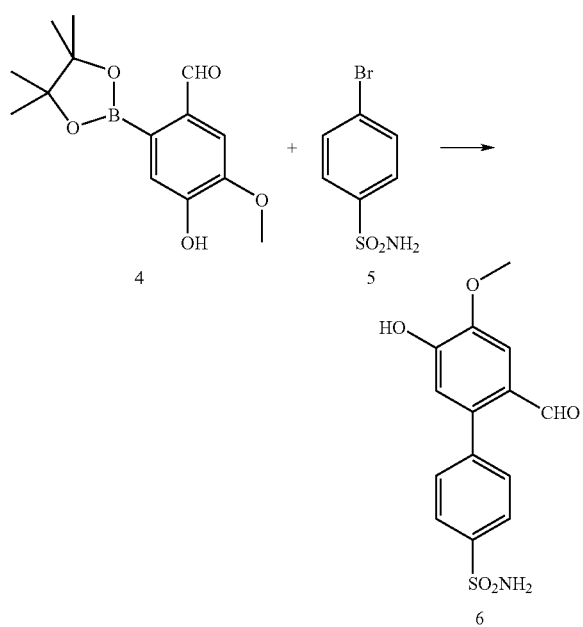

In similar fashion, as outlined in Scheme 6c, compound 4 can be coupled with triflate 7 to provide 8 which can then be used as component B in Scheme 1 to provide THQ compounds of this invention. Suitable conditions for the above Suzuki reactions include, but are not limited to, coupling in the presence of a suitable palladium catalyst, for example tetrakis(triphenylphosphine)palladium, and a suitable base, such as aqueous sodium carbonate or anhydrous potassium carbonate in a suitable solvent such as toluene or dioxane at a temperature between 75-110° C. with a reaction time of 2-24 h.

Scheme 6c

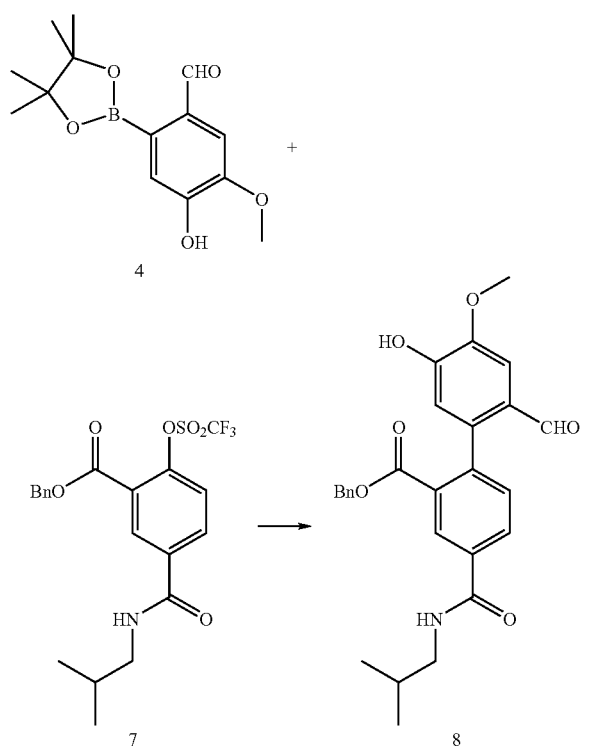

The approaches described herein when applied to the synthesis of biaryl aldehyde intermediates can therefore facilitate the synthesis of a wide range of intermediates derived from either aryl halides or phenols, the precursors to aryl triflates.

It is also realized that the scope of intermediate synthesis can be further extended outside the use of Suzuki methodology since the precursor aryl halides or triflates described above are also precursors for Stille-type cross coupling methodologies. Suitable methodology for the synthesis of substituted aldehydes of Formula III using Stille coupling has been reported by Kohrt et al. (*Tetrahedron Lett.* 2000, 41, 6041-44).

Intermediate aldehydes of the general Formula (IV) may be synthesized according to the example given in Scheme 7. 4-Benzyloxy-2-bromo-3-methoxybenzaldehyde 10 was prepared from 4-benzyloxy-3-methoxybenzaldehyde 9 via electrophilic bromination. The aryl bromide so obtained is a suitable substrate for a copper-mediated displacement of bromide by phenols. In the example shown the ester-substituted phenols can be used to synthesize the intermediate aldehyde 11. This intermediate once isolated can be used directly in the synthesis of the tetrahydroquinolines in an analogous manner to the procedure described in Scheme 2.

Scheme 7

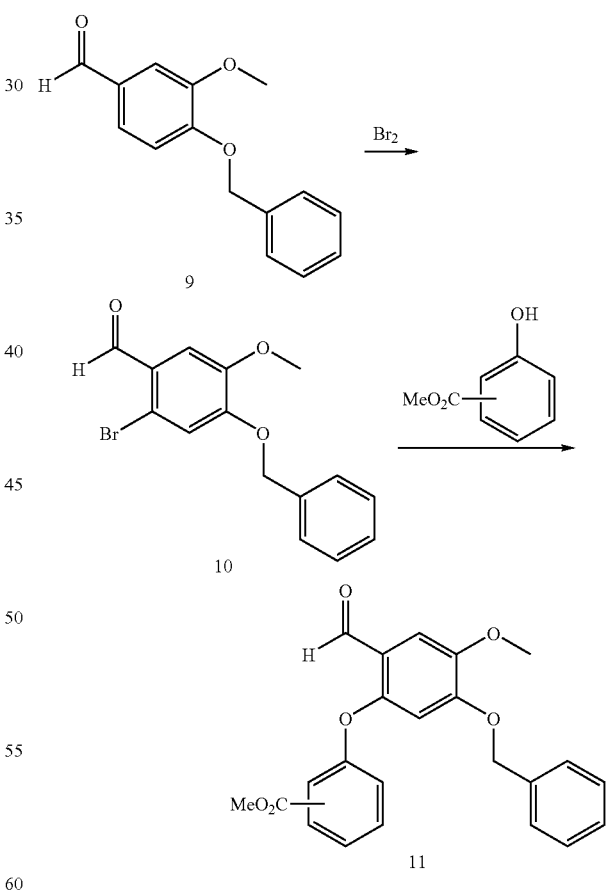

Aldehyde intermediates of the general Formula (V) may be prepared using a boron pinocolate derivative such as compound 4 from Scheme 6a above. Protection of the phenol by treatment with acetic anhydride followed by conversion of the aldehyde to the corresponding 1,3-dioxolane provides compound 4a. This derivative may be effectively coupled with anilines as outlined in Scheme 8 to generate intermediate 12 using methodology similar to that described by Chan et al. (*Tetrahedron Lett.* 1998, 39, 2933-36). Subsequent protection of the aniline as the trifluoroacetate derivative followed by deprotection of the dioxolane function provides aldehyde 13, which may be used directly in the synthesis of the tetrahydroquinolines in an analogous manner to the procedure described in Scheme 2 above.

Scheme 8

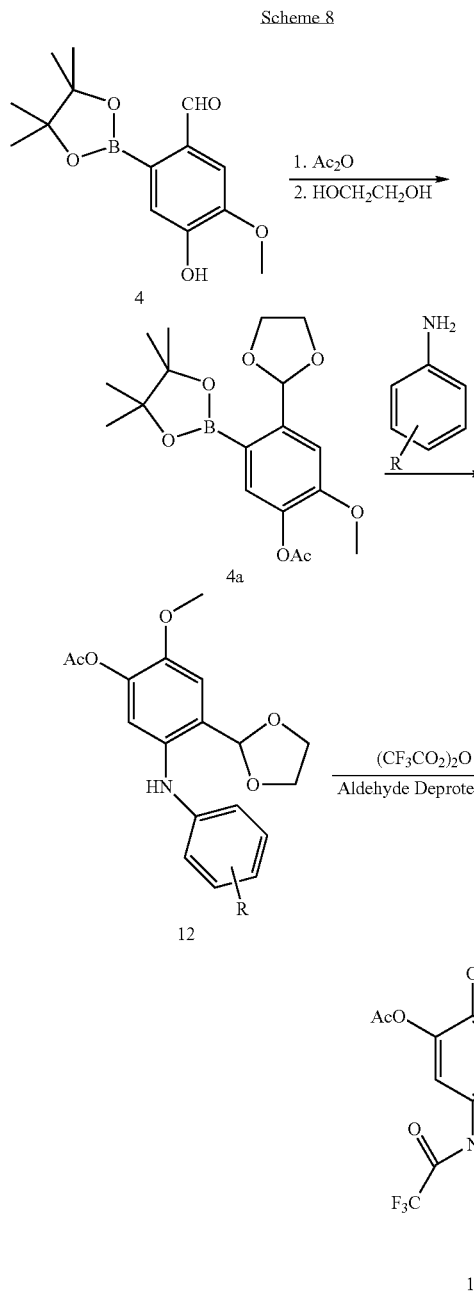

general scheme outlined in Scheme 9 from amines RR'NH, mercaptans RSH, and alcohols ROH, respectively.

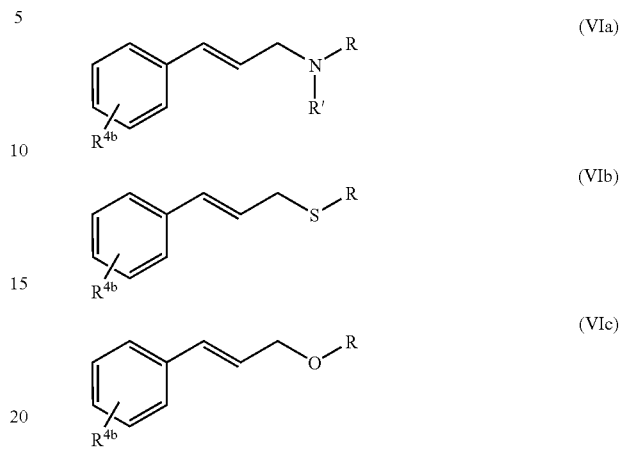

An allylic bromide of formula 14 can be reacted with a nucleophile that is either an amine 15a, a mercaptan 15b, or an alcohol 15c to generate the products 16a-c which can be used according to Scheme 1 above to provide THQ compounds of this invention.

Scheme 9

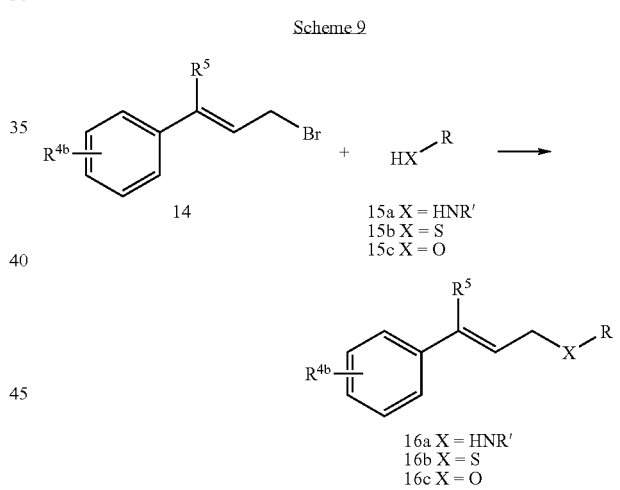

For other embodiments, alternative substitution patterns in the olefin provide the opportunity for expansion of the scope of tetrahydroquinoline synthesis, particularly with respect to functionality within $R^4$.

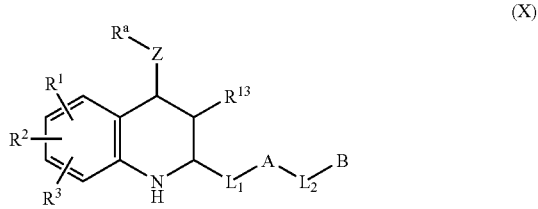

Synthesis of Substituted Olefins C:

Suitably substituted olefins C are either commercially available or can be prepared by various methods known to one skilled the art of organic synthesis. For example, olefins of formulas VIa, VIb, and VIc can derived according to the

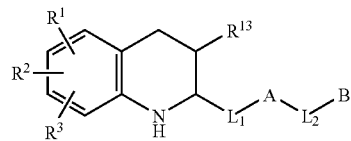

(XI)

THQ Compounds of this invention of general formula (X) wherein Z=O or S ($R^4$ is $OR^a$ or $SR^a$ in Formula (I) above) can be prepared using the method depicted in Scheme 2, by substitution of an appropriately substituted vinyl ether or thioether for the olefin component C in the reaction with aldehyde B and aniline A in the presence of a catalyst such as ytterbium triflate or boron trifluoride etherate. This approach is outlined in Scheme 10 wherein compounds of formula 17a or 17b are converted in compounds of Formula (X) (wherein Z=O or S, respectively.

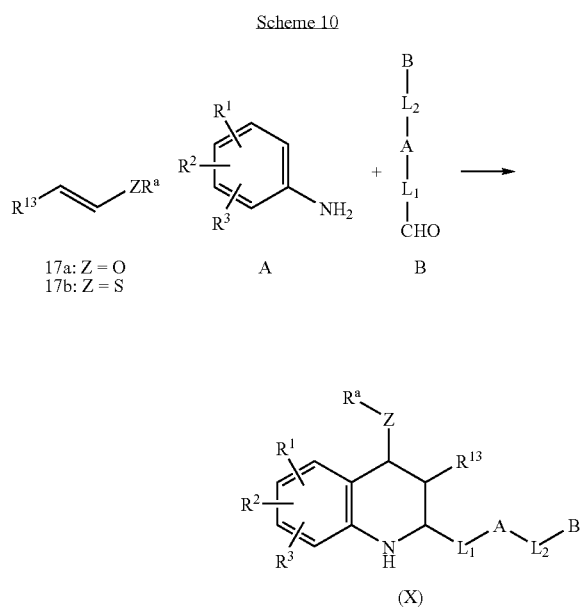

Experimental conditions for the synthesis of compounds of this type have been reported in the work of Kobayashi et al. (*Synthesis*, 1995, (9), 1195-1202), Narasaka et al. (*Heterocycles*, 1993, 35(2), 1039-1053), Crousse et al. (*Tetrahedron Letters*, 1998, 39(32), 5765-5768) and Joh et al. (*Tetrahedron Letters*, 1967, 4199).

The preparation of THQ compounds of general formula (X) wherein Z=NH can be achieved as outlined in Scheme 10a. In this case, the tetrahydroquinoline ring system is derived from the reaction of an aniline A, aldehyde B and an appropriately substituted benzene diazonium salt, such as 18, in the presence of a catalyst such as titanium trichloride to provide THQ compounds of Formula (Xa). Suitable reaction conditions to effect this transformation can be found in the work of Clerici and Porta (*Tetrahedron Letters*, 1990, 31(14), 2069-2072)

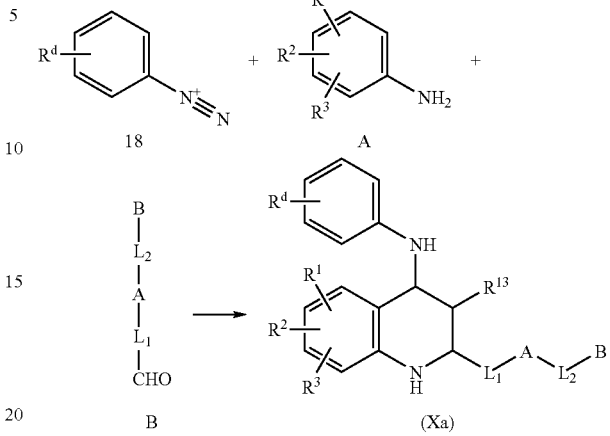

Compounds of general formula (X) may alternatively be synthesized according to methods described by Annunziata et al. (*Tetrahedron*, 1998, 53(28), 9715-9726) as outlined in Scheme 10b, wherein a preformed Schiff's base 20 (derived from an aniline of formula A and an aldehyde 19), is reacted with an aldehyde of formula 22 and an appropriately substituted nucleophile such as alcohol 21a, amine 21b or mercaptan 21c to provide additional target compounds of formula (Xb).

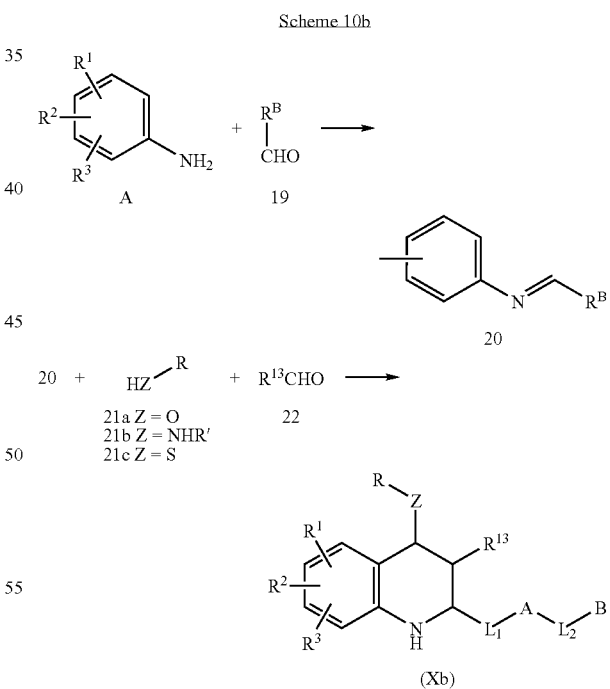

Compounds of general formula (X) wherein Z=S can also serve as starting materials for THQ compounds of formula (XI). As shown in Scheme 11, treatment of a compound of formula (X) wherein Z=S with a reducing agent such as Raney Nickel facilitates a reductive elimination of the thiol group and allows for the preparation of THQ compounds of Formula (I) wherein $R^4$ and $R^5$ both are equal to hydrogen.

Scheme 11

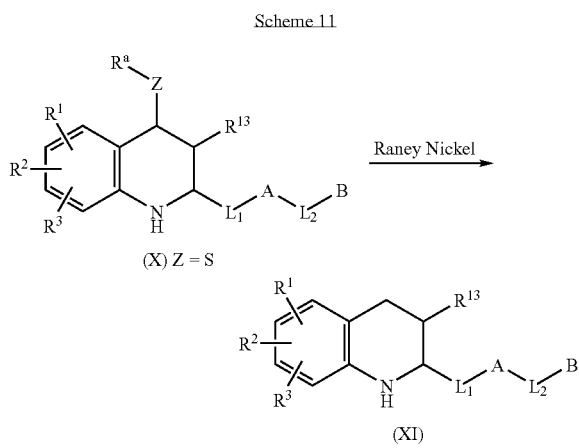

Additional methodology for the synthesis of tetrahydroquinoline ring systems useful in the preparation of THQ compounds described herein has been recently reviewed by Katritzky et al. (*Tetrahedron* 1996, 52, 15031-15070) and can be used by one skilled in the art of organic synthesis to prepare additional examples of the present invention.

Other features of the invention will become apparent in the course of the following descriptions of exemplary embodiments that are given for illustration of the invention and are not intended to be limiting thereof.

EXAMPLES

Solution ratio expresses a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923).

As used throughout the specification, the following abbreviations for chemical reagents apply:
HOAc or AcOH=acetic acid
Bn=benzyl
Bu=butyl
t-Bu=tertiary butyl
Boc=tert-butyl oxycarbonyl
DMF=dimethylformamide
DMSO=dimethyl sulfoxide
Et=ethyl
EtOH=ethanol
EtOAc=ethyl acetate
Me=methyl
MeOH=methanol
NaOAc=sodium actetate
OAc=acetate
Ph=phenyl
Pr=propyl
i-Pr=isopropyl
i-PrOH=isopropanol
TFA=trifluoroacetic acid
THF=tetrahydrofuran
° C.=degrees Celsius
atm=atmosphere
conc.=concentrated
eq=equivalent(s)
h or hr=hour(s)
g=gram(s)
mg=milligram(s)
L=liter(s)
mL=milliliter(s)
µL=microliter(s)
mmol=millimolar
M=molar
meq=milliequivalent(s)
Min=minute(s)
MW=molecular weight
mp=melting point
rt or RT=room temperature
sat or sat'd=saturated
ESI=electrospray ionization mass spectroscopy
HPLC=high performance liquid chromatography
MS=mass spectrometry
LC/MS=liquid chromatography mass spectrometry
NMR=nuclear magnetic resonance spectroscopy
TLC=thin layer chromatography "α", "β", "R", "S", "E", and "Z" are stereochemical designations familiar to one skilled in the art. One stereoisomer of a compound of Formula I may display superior activity compared with the others. Thus, each stereoisomer of a compound of Formula I is considered to be a part of the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of Formula I may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

The following Examples have been prepared, isolated and characterized using the methods disclosed herein. The following Examples demonstrate a partial scope of the invention and are not meant to be limiting of the scope of the invention.

Example 1

2'-(6-Carbamimidoyl-4-phenyl-1,2,3,4-tetrahydroquinolin-2-yl)-4-isobutylcarbamoyl-biphenyl-2-carboxylic acid Part A To a solution of 2-hydroxy-5-formylbenzoic acid (5.0 g, 0.03 mmol) in 80 mL of DMF was added $KHCO_3$ (3.3 g, 0.03 mmol) and benzyl bromide (3.9 mL, 0.03 mmol). The mixture was stirred at room temperature under $N_2$ for 20 h. The reaction mixture was poured into water (240 mL) and it was extracted with EtOAc. The combined organic solution was washed with brine, dried over $MgSO_4$, and concentrated to yellow oil. It was dissolved in $CH_2Cl_2$ (30 mL) and the mixture was cooled at 0° C. Pyridine (11.3 mL, 0.15 mmol) was added, followed by triflate anhydride (8.7 mL, 0.5 mmol, over 30 min). The reaction mixture was stirred at 0° C. for 30 min, poured into water, and extracted with EtOAc. The combined organic solution was washed with brine and dried over $MgSO_4$. It was concentrated and purified by chromatography (silica gel, 10% EtOAc in hexane) to give 6.9 g of colorless oil. MS: 389 (M+1)+.

Part B

The product from Part A (4.6 g, 11.9 mmol) was dissolved in a mixture of t-BuOH (45 mL), $CH_3CN$ (10 mL), and $H_2O$ (15 mL). To the solution was added 2-methyl-2-butene (6.0 mL), sodium dihydrogenphosphate (2.85 g, 23.8 mmoL), and sodium chloride (6.44 g, 71.2 mmol). The reaction mixture was stirred at RT for 2 h and it was poured into water. The precipitate was filtered and dried to give 4.52 g of the corresponding acid as an off while solid. MS: 403.1 (M+1)⁻.

Part C

The acid from Part B (2.5 g, 6.1 mmol) was dissolved in 30 mL of DMF. Isobutylamine (0.8 mL, 7.9 mmol), HBTU (3.8 g, 9.2 mmol), and N-methylmorpholine (1.7 mL, 14.0 mmol) were added. The mixture was stirred at RT under $N_2$ for 12 h. The mixture was poured into water and extracted with EtOAc. The combined organic solution was washed with brine and dried over $MgSO_4$. It was concentrated and purified by chromatography (silica gel, 20% EtOAc in hexane) to give 1.5 g of light yellow solid. Mass spectrum (326.3) and ¹HNMR indicated that it was the phenol. It was dissolved in $CH_2Cl_2$ and cooled to 0° C. Pyridine (1.9 mL) was added, followed by triflate anhydride (1.5 mL). The reaction mixture was stirred at 0° C. for 30 min. It was diluted with $CH_2Cl_2$ and washed with $H_2O$ and brine. It was dried over $MgSO_4$ and concentrated to an off white solid (1.53 g). This material was taken into the next step without further purification. ¹HNMR (DMSO-$d_6$) δ 8.85 (t, 1H), 8.49 (s, 1H), 8.21 (d, 1H), 7.72 (d, 1H), 7.50-7.30 (m, 4H), 5.41 (s, 2H), 3.09 (t, 2H), 1.82 (m, 1H), 0.88 (d, 6H).

Part D

The product from Part C (2.1 g, 4.55 mmol), 2-formylphenylboronic acid (1.0 g, 6.8 mmol), $K_3PO_4$ (1.45 g, 6.8 mmol), and Pd[PPh$_3$]$_4$ (0.53 g, 10%) were dissolved together in 30 mL of DMF. The mixture was de-gassed and heated at 100° C. under $N_2$ for 2 h. The reaction mixture was cooled, poured into water, and extracted with EtOAc. The combined organic solution was washed with brine and dried over $MgSO_4$. It was concentrated and purified by chromatography (silica gel, 10% EtOAc in $CH_2Cl_2$) to give 1.75 g of the biaryl aldehyde. MS: 416.4 (M+1)⁺.

Part E 4-amino-benzamidine mono HCl salt (0.13 g, 0.77 mmol) was suspended in acetonitrile (30 mL). The product from Part D (0.32 g, 0.77 mmol) and styrene (0.88 mL, 7.7 mmol) were added, followed by Indium triflate (0.45 g, 0.77 mmol). The reaction was heated at 70° C. under $N_2$ for 12 h. The mixture was concentrated and dissolved in 30 mL of MeOH and 5 mL of HOAc. This mixture was placed under $H_2$ balloon with 10% Pd/C for 3 h. The reaction mixture was filtered through Celite®, concentrated, and purified by reverse phase HPLC (0.5% TFA in $CH_3CN/H_2O$) to give 100 mg of the desired product as a TFA salt. MS: 547.5 (M+1)⁺.

Example 2

2'-(6-Carbamimidoyl-4-phenyl-1,2,3,4-tetrahydro-quinolin-2-yl)-4-isobutylcarbamoyl-5'-hydroxy-4'-methoxy-biphenyl-2-carboxylic acid Part A The product from Part C of Example 1 was coupled with 4-acetoxy-2-bromo-3-methoxybenzaldehyde (prepared by electrophilic bromonation of 4-acetoxy-3-methoxybenzaldehyde) under Suzuki coupling conditions as described in Part D of Example 1 to give the biaryl aldehyde.

Part B 4-amino-benzamidine mono HCl salt, the product from Part A, styrene, and Indium triflate were reacted in $CH_3CN$ using the same procedure described in Part E of Example 1. The final product was purified by reverse phase HPLC (0.5% TFA in $CH_3CN/H_2O$) as a TFA salt. MS: 594.5 (M+1)⁺.

Example 3

2'-[6-Carbamimidoyl-4-(4-hydroxy-phenyl)-1,2,3,4-tetrahydro-quinolin-2-yl]-5'-hydroxy-4-isobutylcarbamoyl-4'-methoxy-biphenyl-2-carboxylic acid This compound was prepared following the same procedures described in Example 2 using 4-vinyl-phenol instead of styrene. MS: 610.5 (M+1)⁺.

Example 4

2'-(6-Carbamimidoyl-4-phenyl-1,2,3,4-tetrahydro-quinolin-2-yl)-biphenyl-2,4-dicarboxylic acid dimethyl ester Part A 4-Bromoisophthalic acid (0.49 g, 2.0 mmol) was dissolved in MeOH (20 mL) and cooled at 0° C. Thionyl chloride (2.9 mL, 40 mmol) was added dropwise. The cooling bath was removed and the mixture was stirred under $N_2$ for 12 h. The mixture was concentrated, the residue was dried under vacuum to give 0.53 g of the dimethyl ester.

Part B

The dimethyl ester from Part A (0.53 g, 2.0 mmol), 2-formylphenylboronic acid (0.66 g, 4.4 mmol), $K_3PO_4$ (0.59 g, 2.8 mmol), and Pd[PPh$_3$]$_4$ (0.23 g, 10%) were dissolved together in 20 mL of dioxane. The mixture was de-gassed and heated at 110° C. under $N_2$ for 4 h. The reaction mixture was cooled, poured into water, and extracted with EtOAc. The combined organic solution was washed with brine and dried over $MgSO_4$. It was concentrated and purified by chromatography (silica gel, 20-30% EtOAc in hexane) to give 0.35 g of the biaryl aldehyde. ¹HNMR (CDCl$_3$) δ 10.01 (s, 1H), 8.59 (d, 1H), 8.24 (d, 1H), 7.93 (d, 1H), 7.84 (s, 1H), 7.60 (m, 3H), 7.40 (d, 1H), 3.99 (s, 3H), 3.71 (s, 3H).

Part C

The biaryl aldehyde from Part B, 4-amino-benzamidine mono HCl salt, styrene, and Indium triflate were reacted in $CH_3CN$ under the same conditions as described in Part E of Example 1. The final product was purified by reverse phase HPLC (0.5% TFA in $CH_3CN/H_2O$) as a TFA salt. MS: 516.4 (M+1)⁺.

Example 5

2'-(6-Carbamimidoyl-4-phenyl-1,2,3,4-tetrahydro-quinolin-2-yl)-biphenyl-2,4-dicarboxylic acid The product from Example 4 was hydrolyzed with LiOH/THF/$H_2O$ under reflux conditions to give the diacid. The final product was purified by reverse phase HPLC (0.5% TFA in $CH_3CN/H_2O$) as a TFA salt. MS: 492.3 (M+1)⁺.

Example 6

2'-(6-Carbamimidoyl-4-phenyl-1,2,3,4-tetrahydro-quinolin-2-yl)-biphenyl-2-carboxylic acid This compound was prepared using the similar procedures described in Example 5. MS: 448.5 (M+1)⁺.

Example 7

2'-(6-Carbamimidoyl-4-phenyl-1,2,3,4-tetrahydro-quinolin-2-yl)-biphenyl-4-carboxylic acid This compound was prepared using the similar procedures described in Example 5. MS: 448.4 $(M+1)^+$.

Example 8

2'-(6-Carbamimidoyl-4-methyl-4-phenyl-1,2,3,4-tetrahydro-quinolin-2-yl)-biphenyl-2,4-dicarboxylic acid dimethyl ester The biaryl aldehyde from Part B of Example 4, 4-aminobenzamidine mono HCl salt, α-methylstyrene, and indium triflate were reacted in $CH_3CN$ under the same conditions as described in Part E of Example 1. The final product was purified by reverse phase HPLC (0.5% TFA in $CH_3CN/H_2O$) as a TFA salt. MS: 534.3 $(M+1)^+$.

Example 9

2'-(6-Carbamimidoyl-4-methyl-4-phenyl-1,2,3,4-tetrahydro-quinolin-2-yl)-biphenyl-2,4-dicarboxylic acid The product from Example 8 was hydrolyzed with $LiOH/THF/H_2O$ under reflux conditions to give the diacid. The final product was purified by reverse phase HPLC (0.5% TFA in $CH_3CN/H_2O$) as a TFA salt. MS: 506.3 $(M+1)^+$.

Example 10

3'-(6-Carbamimidoyl-4-phenyl-1,2,3,4-tetrahydro-quinolin-2-yl)-4-isobutylcarbamoyl-biphenyl-2-carboxylic acid Part A The product from Part C of Example 1 (1.53 g, 3.33 mmol), 3-formylphenylboronic acid (0.60 g, 4.0 mmol), $K_3PO_4$ (1.06 g, 5.0 mmol), and $Pd[PPh_3]_4$ (0.38 g, 10%) were added together with 20 mL of DMF. The mixture was de-gassed and heated at 100° C. under $N_2$ for 2 h. The reaction mixture was cooled, poured into water, and extracted with EtOAc. The combined organic solution was washed with brine and dried over $MgSO_4$. It was concentrated and purified by chromatography (silica gel, 10% EtOAc in $CH_2Cl_2$) to give 0.73 g of the biaryl aldehyde. MS: 416.4 $(M+1)^+$.

Part B 4-amino-benzamidine bis HCl salt (0.16 g, 0.77 mmol) was suspended in acetonitrile (30 mL). Triethylamine (0.1 mL, 0.77 mmol) was added, followed by the product from Part A (0.32 g, 0.77 mmol), styrene (0.88 mL, 7.7 mmol), and indium triflate (0.45 g, 0.77 mmol). The reaction was heated at 70° C. under $N_2$ for 12 h. The mixture was concentrated and dissolved in 30 mL of MeOH and 5 mL of HOAc. This mixture was placed under $H_2$ balloon with 10% Pd/C for 3 h. The reaction mixture was filtered through celite, concentrated, and purified by reverse phase HPLC (0.5% TFA in $CH_3CN/H_2O$) to yield 100 mg of the desired product as a TFA salt. MS: 547.5 $(M+1)^+$.

Example 11

3'-(6-Carbamimidoyl-4-phenyl-1,2,3,4-tetrahydro-quinolin-2-yl)-4-t-butylcarbamoyl-biphenyl-2-carboxylic acid This compound was prepared following the same methods described in Example 10. MS: 547.3 $(M+1)^+$.

Example 12

3'-(6-Carbamimidoyl-4-phenyl-1,2,3,4-tetrahydro-quinolin-2-yl)-biphenyl-2,4-dicarboxylic acid Part A The dimethyl ester from Part A of Example 5 (0.29 g, 1.96 mmol), 3-formylphenylboronic acid (0.53 g, 1.96 mmol), $K_3PO_4$ (1.66 g, 7.84 mmol), and $Pd[PPh_3]_4$ (0.11 g, 5%) were dissolved together in 10 mL of dioxane. The mixture was de-gassed and heated at 110° C. under $N_2$ for 4 h. The reaction mixture was cooled, poured into water, and extracted with EtOAc. The combined organic solution was washed with brine and dried over $MgSO_4$. It was concentrated and purified by chromatography (silica gel, 20-30% EtOAc in hexane) to give 0.53 g of the biaryl aldehyde. $^1HNMR$ ($CDCl_3$) δ 10.07 (s, 1H), 8.59 (d, 1H), 8.24 (d, 1H), 7.93 (d, 1H), 7.84 (s, 1H), 7.60 (m, 2H), 7.48 (d, 2H), 3.98 (s, 3H), 3.71 (s, 3H).

Part B

The biaryl aldehyde from Part A, 4-amino-benzamidine mono HCl salt, styrene, and Indium triflate were reacted in $CH_3CN$ under the same conditions as described in Part E of Example 1. The crude product was hydrolyzed with $LiOH/THF/H_2O$ under reflux conditions to give the diacid. The final product was purified by reverse phase HPLC (0.5% TFA in $CH_3CN/H_2O$) as a TFA salt. MS: 492.3 $(M+1)^+$.

Example 13

3'-(6-Carbamimidoyl-4-phenyl-1,2,3,4-tetrahydro-quinolin-2-yl)-biphenyl-2-carboxylic acid This compound was prepared following the same methods described for Example 6 using 3-formylphenylboronic acid instead of 2-formylphenylboronic acid. MS: 449.4 $(M+1)^+$.

Example 14

4-Phenyl-2-(2'-sulfamoyl-biphenyl-3-yl)-1,2,3,4-tetrahydro-quinoline-6-carboxamidine Part A 2-(t-Butylanimesulfonyl)phenylboronic acid (1.0 g, 3.98 mmol), 3-formylphenylbromide (0.46 mL, 3.98 mmol), $K_3PO_4$ (1.27 g, 5.97 mmol), and $Pd[PPh_3]_4$ (0.46 g, 10%) were dissolved together in 30 mL of dioxane. The mixture was de-gassed and heated at 110° C. under $N_2$ for 12 h. The reaction mixture was cooled, poured into water, and extracted with EtOAc. The combined organic solution was washed with brine and dried over $MgSO_4$. It was concentrated and purified by chromatography (silica gel, 25% EtOAc in hexane) to give 1.15 g of the biaryl aldehyde. MS: 339.3 $(M+Na)^+$.

Part B

The biaryl aldehyde from Part A, 4-amino-benzamidine mono HCl salt, styrene, and Indium triflate were reacted in $CH_3CN$ under the same conditions as described in Part E of Example 1. The final product was purified by reverse phase HPLC (0.5% TFA in CH$_3$CN/H$_2$O) as a TFA salt. MS: 483.4 (M+1)$^+$.

Example 15

4-Methyl-4-phenyl-2-(2'-sulfamoyl-biphenyl-3-yl)-1,2,3,4-tetrahydro-quinoline-6-carboxamidine This compound was prepared following the same methods described in Example 14 using α-methylstyrene instead of styrene. MS: 497.0 (M+1)$^+$.

Example 16

3'-(6-Carbamimidoyl-4-phenyl-1,2,3,4-tetrahydro-quinolin-2-yl)-biphenyl-2,4-dicarboxylic acid 4-methyl ester The acid from Part B of Example 1 was protected as the methyl ester. It was then coupled with 3-formayphenylboronic acid under Suzuki conditions as described above to give the biaryl aldehyde. Tetrahydeoquinoline formation of the aldehyde with 4-aminobenzamidine and styrene under the same conditions, followed by hydrogenation to remove the benzyl protecting group gave the final product. MS: 506.4 (M+1)$^+$.

Example 17

3'-(6-Carbamimidoyl-4-phenyl-1,2,3,4-tetrahydro-quinolin-2-yl)-biphenyl-2,4-dicarboxylic acid diamide The biaryl aldehyde from Example 16 was reacted under the same THQ formation conditions with styrene and 2-methyl-4-(aminophenyl)oxadiazole. The resulting product underwent hydrolysis in NH$_3$/DMF/ethyleneglycol at 80° C. for 12 h to give the bisamine. The oxadiazole was then converted to the benzamidine by Raney/Ni hydrogenation to give the final product. MS: 490.4 (M+1)$^+$.

Example 18

3'-(6-Carbamimidoyl-4-methyl-4-phenyl-1,2,3,4-tetrahydro-quinolin-2-yl)-4-carbamoyl-biphenyl-2-carboxylic acid Part A 2-Bromo-5-iodobenzoic acid (6.54 g, 20.0 mmol) was dissolved in DMF (70 mL). Potassium bicarbonate (2.2 g, 22.0 mmol) was added, followed by benzyl bromide (2.8 mL, 22.0 mmol). The mixture was stirred at RT under N$_2$ for 12 h. The reaction mixture was poured into water and extracted with EtOAc. The combined organic solution was washed with brine and dried over MgSO$_4$. It was concentrated and dried to give 9.05 g of the benzyl ester.

Part B

The benzyl ester from part A (2.3 g, 7.69 mmol), Zn(CN)$_2$ (1.3 g, 11.5 mmol), and Pd[PPh$_3$]$_4$ were dissolved together in 25 mL of DMF. The mixture was de-gassed and heated at 90° C. for 4 h. It was diluted with 100 mL of NH$_4$OH/H$_2$O and extracted with EtOAc. The combined organic solution was washed with brine and dried over MgSO$_4$. It was concentrated and purified by chromatography (silica gel, 5% EtOAc in hexane) to give 1.8 g of the cyano derivative. MS: 316.0, 317.9 (M+1)$^+$.

Part C

The cyano-intermediate from Part B (1.4 g, 4.4 mmol) was dissolved in 15 mL of DMF. The reaction mixture was cooled at 0° C. Potassium carbonate (0.20 g, 1.45 mmol) was added, followed by dropwise addition of H$_2$O$_2$ (1.2 mL of 30%). The cooling bath was removed and the mixture was stirred at RT for 12 h. The reaction was quenched with aqueous NaHSO$_3$ and water. The precipitate formed was filtered and dried to give 1.1 g of the desired amide. MS: 334.2, 336.3 (M+1)$^+$.

Part D

The product from Part C (7.2 g, 21.6 mmol), 3-formylphenylboronic acid (4.82 g, 32.4 mmol), K$_3$PO$_4$ (7.5 g, 35.7 mmol), and Pd[PPh$_3$]$_4$ (2.42 g, 10%) were dissolved together in 80 mL of dioxane. The mixture was de-gassed and heated at 110° C. under N$_2$ for 2 h. The reaction mixture was cooled, poured into water, and extracted with EtOAc. The combined organic solution was washed with brine and dried over MgSO$_4$. It was concentrated and purified by chromatography (silica gel, a. 25-80% EtOAc in hexane, b. 40:40:1 EtOAc/hexane/MeOH) to give 7.2 g of the biaryl aldehyde. $^1$HNMR (CDCl$_3$) δ 9.93 (s, 1H), 8.35 (d, 1H), 8.05 (dd, 1H), 7.83 (dd, 1H), 7.75 (s, 1H), 7.55-7.43 (m, 4H), 7.28 (m, 3H), 7.08 (m, 2H), 3.10 (s, 2H).

Part E

4-Amino-benzamidine mono HCl salt (0.11 g, 0.58 mmol) was suspended in acetonitrile (30 mL). The product from Part D (0.21 g, 0.58 mmol) and α-methylstyrene (0.34 mL, 2.92 mmol) were added, followed by Indium triflate (0.17 g, 0.29 mmol). The mixture was degassed and heated at 70° C. under N$_2$ for 2 h. The mixture was concentrated and dissolved in 30 mL of MeOH and 5 mL of HOAc. This mixture was placed under H$_2$ balloon with 10% Pd/C for 6 h. The reaction mixture was filtered through celite, concentrated, and purified by reverse phase HPLC (0.5% TFA in CH$_3$CN/H$_2$O) to give 80 mg of the desired product as a TFA salt. MS: 505.3 (M+1)$^+$.

Example 19

3'-(6-Carbamimidoyl-4-phenyl-1,2,3,4-tetrahydro-quinolin-2-yl)-4-carbamoyl-biphenyl-2-carboxylic acid This compound was prepared using the similar procedures described in Example 18 using styrene instead of ax-methylstyrene. MS: 491.3 (M+1)$^+$.

Example 20

3'-(6-Carbamimidoyl-4-methyl-4-phenyl-1,2,3,4-tetrahydro-quinolin-2-yl)-biphenyl-2,4-dicarboxylic acid 4-Amino-benzamidine mono HCl salt (59.0 mg, 0.34 mmol) was suspended in acetonitrile (10 mL). The product from Part A of Example 12 (100.0 mg, 0.34 mmol) and α-methylstyrene (0.22 mL, 1.70 mmol) were added, followed by Indium triflate (96.0 mg, 0.17 mmol). The mixture was heated at 70° C. under N$_2$ for 5 h. The mixture was concentrated and purified by reverse phase HPLC. The product was then dissolved in 5 mL of THF and LiOH (42 mg) was added. The mixture was refluxed under N$_2$ for 1.5 h and then stirred at RT for 12 h. The reaction mixture was concentrated and purified by reverse phase HPLC (0.5% TFA in CH$_3$CN/H$_2$O) to give 25 mg of the desired product as a TFA salt. MS: 506.3 (M+1)$^+$.

Example 21

3'-(6-Carbamimidoyl-4-ethyl-4-phenyl-1,2,3,4-tetrahydro-quinolin-2-yl)-biphenyl-2,4-dicarboxylic acid This compound was prepared following the same methods described in Example 20 using α-ethylstyrene. MS: 520.3 $(M+1)^+$.

Example 22

3'-(6-Carbamimidoyl-4-propylyl-4-phenyl-1,2,3,4-tetrahydro-quinolin-2-yl)-biphenyl-2,4-dicarboxylic acid This compound was prepared following the same methods described in Example 20 using α-propylstyrene. MS: 534.3 $(M+1)^+$.

Example 23

4-Amino-3'-(6-carbamimidoyl-4-methyl-4-phenyl-1,2,3,4-tetrahydro-quinolin-2-yl)-biphenyl-2-carboxylic acid Part A Methyl 2-bromo-5-nitrobenzoate (0.98 g, 3.77 mmol), 3-formylphenylboronic acid (0.57 g, 3.77 mmol), $K_3PO_4$ (3.2 g, 15.1 mmol), and $Pd[PPh_3]_4$ (0.22 g, 5%) were dissolved together in 20 mL of dioxane. The mixture was de-gassed and heated at 110° C. under $N_2$ for 4 h. The reaction mixture was cooled, poured into water, and extracted with EtOAc. The combined organic solution was washed with brine and dried over $MgSO_4$. It was concentrated and purified by chromatography (silica gel, 20% EtOAc in hexane) to give 0.92 g of the biaryl aldehyde. MS: 327.2 $(M+CH_3CN+H)^+$ Part B 2-(4-Aminobphenyl)-5-methyloxadiazole (0.31 g, 1.75 mmol) was suspended in acetonitrile (20 mL). The product from Part A (0.0.50 g, 1.75 mmol) and α-methylstyrene (1.1 mL, 8.75 mmol) were added, followed by Indium triflate (0.49 g, 0.88 mmol). The mixture was heated at 70° C. under $N_2$ for 4 h. The mixture was concentrated and purified by silica gel chromatography (20% EtOAc in hexane) to give 0.60 mg of the desired product. MS: 561.2 $(M+1)^+$.

Part C

A solution of the product from B (0.56 g, 1 mmol) in 15 mL of THF/dioxane mixture (1:1) was added to a mixture of sodium hydrosulfide (0.52 g, 3 mmol) in 5 mL of $H_2O$ at RT. The mixture was stirred at RT under $N_2$ for 2 h. The mixture was concentrated and then dissolved in $CH_2Cl_2$. It was washed with water and brine, dried over $MgSO_4$, and concentrated to a yellow solid (0.49 g). MS: 531.3 $(M+1)^+$.

Part D

The product from Part C (50 mg, 0.094 mmol) was dissolved in MeOH (5 mL) and $H_2O$ (1 mL). LiOH (21.0 mg, 0.5 mmol) was added. The mixture was refluxed under $N_2$ for 2 h. It was diluted with water and extracted with EtOAc. The combined organic mixture was washed with water and brine, dried over $MgSO_4$, and concentrated (47.0 g). MS: 517.3 $(M+1)^+$.

Part E

The product from Part D (46.0 mg, 0.09 mmol) was dissolved in EtOH and HOAc (21 mL/3 mL). It was placed on a hydrogenator under 50 psi with Raney Ni for 7 h. The mixture filtered through Ceilite®, concentrated, and purified by reverse phase HPLC (0.5% TFA in $CH_3CN/H_2O$) to give 13 mg of the desired product as a TFA salt. MS: 477.3 $(M+1)^+$.

Example 24

3'-(6-Carbamimidoyl-4-methyl-4-phenyl-1,2,3,4-tetrahydro-quinolin-2-yl)-4-(3-methyl-ureido)-biphenyl-2-carboxylic acid Part A The product from Part C of Example 23 (100 mg, 0.19 mmol) was dissolved in 5 mL of $CH_2Cl_2$. Triethylamine (100 mg, 1 mmol) was added, followed by methyl isocyanate (29 mg, 0.5 mmol). The mixture was stirred at RT under $N_2$ for 12 h. It was diluted with $CH_2Cl_2$, washed with water and brine, dried over $MgSO_4$, and concentrated (133.0 g). MS: 588.4 $(M+1)^+$.

Part B

The product from Part A was hydrolyzed and then converted to the benzamidine following the same procedures described in Part D and Part E of Example 23. MS: 534.4 $(M+1)^+$.

Example 25

3'-(6-Carbamimidoyl-4-methyl-4-phenyl-1,2,3,4-tetrahydro-quinolin-2-yl)-4-methanesulfonylamino-biphenyl-2-carboxylic acid Part A The product from Part C of Example 23 (100 mg, 0.19 mmol) was dissolved in 5 mL of $CH_2Cl_2$. Triethylamine (100 mg, 1 mmol) was added, followed by methane sulfonylchloride (46 mg, 0.4 mmol). The mixture was stirred at RT under $N_2$ for 4 h. It was diluted with $CH_2Cl_2$, washed with water and brine, dried over $MgSO_4$, and concentrated (48.0 g). MS: 588.4 $(M+1)^+$, 687.3. The crude product mixture contained both the mono and bis-sulfonated products. It was taken into the next step without further purification.

Part B

The product from Part A was hydrolyzed and then converted to the benzamidine following the same procedures described in Part D and Part E of Example 23. MS: 555.4 $(M+1)^+$.

Example 26

4-Acetylamino-3'-(6-carbamimidoyl-4-methyl-4-phenyl-1,2,3,4-tetrahydro-quinolin-2-yl)-biphenyl-2-carboxylic acid Part A The product from Part C of Example 23 (100 mg, 0.19 mmol) was dissolved in 5 mL of $CH_2Cl_2$. Triethylamine (100 mg, 1 mmol) was added, followed by acetyl chloride (39 mg, 0.5 mmol). The mixture was stirred at RT under $N_2$ for 2 h. It was diluted with $CH_2Cl_2$, washed with water and brine, dried over $MgSO_4$, and concentrated (166.0 g). MS: 573.4 $(M+1)^+$.

Part B

The product from Part A was hydrolyzed and then converted to the benzamidine following the same procedures described in Part D and Part E of Example 23. MS: 519.4 (M+1)$^+$.

Example 27

3'-(6-Carbamimidoyl-4-methyl-4-phenyl-1,2,3,4-tetrahydro-quinolin-2-yl)-4-cyano-biphenyl-2-carboxylic acid Part A The product from Part B of Example 18 (0.32 g, 1.0 mmol), 3-formylphenylboronic acid (0.23 g, 1.5 mmol), K$_3$PO$_4$ (0.32 g, 1.5 mmol), and Pd[PPh$_3$]$_4$ (0.12 g, 10%) were dissolved together in 20 mL of DMF. The mixture was de-gassed and heated at 100° C. under N$_2$ for 2 h. More 3-formylphenylboronic acid (50 mg) was added and the mixture was heated at 100° C. for 1.5 h. The reaction mixture was cooled, poured into water, and extracted with EtOAc. The combined organic solution was washed with brine and dried over MgSO$_4$. It was concentrated and purified by chromatography (silica gel, 5-10% EtOAc in hexane) to give 0.21 g of the biaryl aldehyde. $^1$HNMR (CDCl$_3$) δ 9.93 (s, 1H), 8.23 (d, 1H), 7.84 (m, 2H), 7.74 (dd, 1H), 7.50 (m, 3H), 7.30 (m, 2H), 7.12 (m, 2H), 5.12 (s, 2H).

Part B

4-Amino-benzamidine mono HCl salt (30 mg, 0.16 mmol) was suspended in acetonitrile (5 mL). The product from Part A (55 mg, 0.16 mmol) and α-methylstyrene (0.12 mL, 0.81 mmol) were added, followed by Indium triflate (50 mg, 0.08 mmol). The mixture was de-gassed and heated at 70° C. under N$_2$ for 6 h. It was then concentrated, and purified by reverse phase HPLC (0.5% TFA in CH$_3$CN/H$_2$O) to give 50 mg of the benzyl protected product as a TFA salt. MS: 577.7 (M+1)$^+$. The TFA salt was dissolved in 6 mL of MeOH. This mixture was placed under H$_2$ balloon with 10% Pd/C for 1 h. The reaction mixture was filtered through celite, concentrated, and purified by reverse phase HPLC (0.5% TFA in CH$_3$CN/H$_2$O) to give 16 mg of the desired product as a TFA salt. MS: 487.5 (M+1)$^+$.

Example 28

3'-(6-Carbamimidoyl-4-methyl-4-phenyl-1,2,3,4-tetrahydro-quinolin-2-yl)-biphenyl-2,4-dicarboxylic acid 4-methyl ester This compound was prepared following the same methods described in Example 16 using α-methylstyrene instead of styrene. MS: 520.4 (M+1)$^+$.

Example 29

3'-(6-Carbamimidoyl-4-methyl-4-phenyl-1,2,3,4-tetrahydro-quinolin-2-yl)-biphenyl-2-carboxylic acid This compound was prepared following the same methods described in Example 13 using α-methylstyrene instead of styrene. MS: 462.3 (M+1)$^+$.

Example 30

3'-(6-Carbamimidoyl-4-methyl-4-phenyl-1,2,3,4-tetrahydro-quinolin-2-yl)-4-methylcarbamoyl-biphenyl-2-carboxylic acid This compound was prepared following the same methods described in Example 10. MS: 519.3 (M+1)$^+$.

Example 31

3'-(6-Carbamimidoyl-4-methyl-4-phenyl-1,2,3,4-tetrahydro-quinolin-2-yl)-4-isopropylcarbamoyl-biphenyl-2-carboxylic acid This compound was prepared following the same methods described in Example 10. MS: 547.4 (M+1)$^+$.

Example 32

3'-(6-Carbamimidoyl-4-methyl-4-phenyl-1,2,3,4-tetrahydro-quinolin-2-yl)-4-t-butylcarbamoyl-biphenyl-2-carboxylic acid This compound was prepared following the same methods described in Example 10. MS: 561.3 (M+1)$^+$.

Example 33

3'-[6-Carbamimidoyl-4-(4-fluoro-phenyl)-4-methyl-1,2,3,4-tetrahydro-quinolin-2-yl]-4-carbamoyl-biphenyl-2-carboxylic acid This compound was prepared following the same methods described in Example 18 using 4-fluoro-α-methylstyrene instead of α-methylstyrene. MS: 523.4 (M+1)$^+$.

Example 34

3'-(6-Carbamimidoyl-4-methyl-4-phenyl-1,2,3,4-tetrahydro-quinolin-2-yl)-4-dimethylaminomethyl-biphenyl-2-carboxylic acid Part A 2-hydroxy-5-formylbenzoic acid was protected as a methyl ester and then underwent reductive amination with dimethylamine and sodium cyanoborohydride in methanol to give methyl 2-hydroxy-5-(dimethylaminomethyl)benzoate. MS: 209.1 (M+1)$^+$. The phenol was then reacted with triflate anhydride as described in Example 1 to give the triflate. MS: 341.31 (M+1)$^+$.

Part B

The product from Part A (0.44 g, 1.29 mmol), 3-formylphenylboronic acid (0.29 g, 1.94 mmol), K$_3$PO$_4$ (0.41 g, 1.94 mmol), and Pd[PPh$_3$]$_4$ (0.15 g, 10%) were dissolved together in 15 mL of 1,4-dioxane. The mixture was de-gassed and heated at 110° C. under N$_2$ for 2 h. The reaction mixture was cooled, poured into water, and extracted with EtOAc. The combined organic solution was washed with brine and dried over MgSO$_4$. It was concentrated and purified by chromatography (silica gel, 50% EtOAc in CH$_2$Cl$_2$ and 5% MeOH in CHCl$_3$) to give 0.33 g of the biaryl aldehyde. MS: 298.3 (M+1)$^+$.

Part C 2-(4-Aminobphenyl)-5-methyloxadiazole (59 mg, 0.34 mmol) was suspended in acetonitrile (10 mL). The product from Part B (100 mg, 0.34 mmol) and α-methylstyrene (0.22 mL, 1.7 mmol) were added, followed by Indium triflate (95 mg, 0.17 mmol). The mixture was heated at 70° C. under N$_2$ for 4 h. The mixture was concentrated and taken into the next step without purification. MS: 537.4 (M+1)$^+$.

Part D

The product from Part C was dissolved in MeOH (5 mL), THF (5 mL), and H$_2$O (2 mL). LiOH (42 mg) was added. The mixture was refluxed under N₂ for 8 h. It was concentrated and purified by reverse phase HPLC (0.5% TFA in CH₃CN/H₂O) to give 177 mg of the acid as a TFA salt. MS: 559.4 (M+1)⁺.

Part E

The product from Part D (86 mg, 0.15 mmol) was dissolved in EtOH and HOAc (21 mL/3 mL). It was placed on a hydrogenator under 50 psi with Raney Ni for 48 h. The mixture was filtered through CeliteO, concentrated, and purified by reverse phase HPLC (0.5% TFA in CH₃CN/H₂O) to give 36 mg of the desired product as a TFA salt. MS: 519.4 (M+1)⁺.

Example 35

3'-(6-Carbamimidoyl-3-methyl-4-phenyl-1,2,3,4-tetrahydro-quinolin-2-yl)-4-carbamoyl-biphenyl-2-carboxylic acid 4-Amino-benzamidine mono HCl salt (0.21 g, 1.23 mmol) was suspended in acetonitrile (20 mL). The product from Part D of Example 18 (0.42 g, 1.23 mmol) and trans-β-methylstyrene (0.75 mL, 6.2 mmol) were added, followed by Indium triflate (0.33 g, 0.62 mmol). The mixture was de-gassed and heated at 70° C. under N₂ for 22 h. It was then concentrated, and purified by reverse phase HPLC (0.5% TFA in CH₃CN/H₂O) to yield the benzyl protected product as a TFA salt. MS: 595.3 (M+1)⁺. The TFA salt was dissolved in 6 mL of MeOH. This mixture was placed under H₂ balloon with 10% Pd/C for 1 h. The reaction mixture was filtered through celite, concentrated, and purified by reverse phase HPLC (0.5% TFA in CH₃CN/H₂O) to give the desired product as a TFA salt. MS: 505.3 (M+1)⁺.

Example 36

5'-Amino-3'-(6-carbamimidoyl-4-methyl-4-phenyl-1,2,3,4-tetrahydro-quinolin-2-yl)-4-carbamoyl-biphenyl-2-carboxylic acid Part A The product from Part C of Example 18 (4.7 g, 14.1 mmol), 3-carboxyl-5-nitrophenylboronic acid (2.98 g, 14.1 mmol), K₃PO₄ (4.5 g, 21.2 mmol), and Pd[PPh₃]₄ (0.82 g, 5%) were dissolved together in 50 mL of DMF. The mixture was de-gassed and heated at 100° C. under N₂ for 8 h. The reaction mixture was cooled, poured into water, and extracted with EtOAc. The combined organic solution was washed with brine and dried over MgSO₄. It was concentrated and recrystalized from EtOAc and CH₂Cl₂ to give 1.6 g of the biaryl aldehyde. MS: 421.2 (M+1)⁺.

Part B

The product from Part A (0.80 g, 1.9 mmol) was dissolved in 20 mL of THF at RT. Triethylamine (0.32 mL, 2.1 mmol) was added, followed by isobutyl chloroformate (0.30 mL, 2.1 mmol). The mixture was stirred at RT under N₂ for 20 min. NaBH₄ (0.28 g) was added, followed by a few drops of water. The reaction mixture was stirred at RT for 1.5 h. The reaction was quenched with 1N HCl and water. It was extracted with EtOAc. The combined EtOAc solution was washes with water and brine, dried over MgSO₄, concentrated, and purified by chromatography (silica gel, 1-5% MeOH in CH₂Cl₂) to give 0.28 g of the corresponding alcohol. MS: 407.2 (M+1)⁺.

Part C

The product from Part B (0.25 g, 0.62 mmol) and MnO₂ (0.43 g, 4.9 mmol) were refluxed with benzene (15 mL) under N₂ for 20 h. It was filtered through celite, concentrated, and purified by chromatography (silica gel, 3-4% MeOH in CH₂Cl₂) to give 0.18 g of the corresponding aldehyde. ¹HNMR (CDCl₃) δ 9.96 (s, 1H), 8.48 (d, 2H), 8.30 (d, 1H), 8.13 (m, 1H), 8.00 (m, 1H), 7.45 (dd, 1H), 7.26 (m, 3H), 7.08 (m, 2H), 5.11 (s, 2H).

Part D

4-Amino-benzamidine mono HCl salt (16 mg, 0.09 mmol) was suspended in acetonitrile (5 mL). The product from Part C of (33 mg, 0.09 mmol) and α-methylstyrene (0.05 mL, 0.47 mmol) were added, followed by Indium triflate (25 mg, 0.05 mmol). The mixture was de-gassed and heated at 70° C. under N₂ for 2 h. It was then concentrated, and purified by reverse phase HPLC (0.5% TFA in CH₃CN/H₂O) to the benzyl protected product as a TFA salt. MS: 640.3 (M+1)⁺. The TFA salt was dissolved in 6 mL of MeOH. This mixture was placed under 45 psi of H₂ with 10% Pd/C for 2 h. The reaction mixture was filtered through celite, concentrated, and purified by reverse phase HPLC (0.5% TFA in CH₃CN/H₂O) to give the desired product as a TFA salt (6.2 mg). MS: 520.3 (M+1)⁺.

Example 37

5'-Amino-3'-(6-carbamimidoyl-4-phenyl-1,2,3,4-tetrahydro-quinolin-2-yl)-biphenyl-2-carboxylic acid This compound was prepared following the same methods described in Example 36. MS: 463.2 (M+1)⁺.

Example 38

5'-Acetylamino-3'-(6-carbamimidoyl-4-methyl-4-phenyl-1,2,3,4-tetrahydro-quinolin-2-yl)-4-carbamoyl-biphenyl-2-carboxylic acid Part A 2-(4-Aminobphenyl)-5-methyloxadiazole (72 mg, 0.41 mmol) was suspended in acetonitrile (10 mL). The product from Part C of Example 36 (150 mg, 0.37 mmol) and α-methylstyrene (0.25 mL, 1.86 mmol) were added, followed by Indium triflate (104 mg, 0.20 mmol). The mixture was de-gassed and heated at 70° C. under N₂ for 6 h. The mixture was concentrated, and purified by chromatography (silica gel, 30% EtOAc in hexane and then 3% MeOH in CH₂Cl₂) to give 0.17 g of the desired product. MS: 680.3 (M+1)⁺.

Part B

The product from Part A (0.17 g) was dissolved in THF (4 mL) and dioxane (4 mL). A solution of Na₂S₂O₄ in H₂O (4 mL) was added. The mixture was stirred at RT under N₂ for 48 h. It was poured into water and extracted with EtOAc. The combined EtOAc solution was washed with water and brine, dried over MgSO₄, concentrated to give 90 mg of starting material. The aqueous layer was then extracted with CHCl₃. The CHCl₃ solution was washed with water and brine, dried over MgSO₄, concentrated to give 70 mg of the desired amine. MS: 650.4 (M+1)⁺.

Part C

The product from Part B (70 mg, 0.11 mmol) was dissolved in 10 mL of CH₂Cl₂. It was cooled at 0° C. and triethylamine (0.1 mL) was added, followed by acetyl chloride (21 μL). The mixture was stirred at 0° C. under N₂ for 1.5 h. Water and CH₂Cl₂ were added. The two layers were separated. The CH₂Cl₂ layer was washes with water and brine, dried over MgSO₄, concentrated to give 80 mg of crude product. MS: 692.0 (M+1)⁺.

Part D

The product from Part C was dissolved in 10 mL of EtOH and HOAc (7:1). It was placed on a hydrogenator under 50 psi with Raney Ni for 20 h. The mixture was filtered through Celite® and concentrated. The resulting solid was dissolved in 10 mL of EtOH and HOAc (7:1). It was placed on a hydrogenator under 40 psi with 10% Pd/C for 2 h. The mixture was filtered through Celite® and concentrated. The crude product was purified by reverse phase HPLC (0.5% TFA in $CH_3CN/H_2O$) to give 10 mg of the desired product as a TFA salt. MS: 562.4 $(M+1)^+$.

Example 39

3'-(6-Carbamimidoyl-4-methyl-4-phenyl-1,2,3,4-tetrahydro-quinolin-2-yl)-4-carbamoyl-5'-(3-methyl-butyrylamino)-biphenyl-2-carboxylic acid This compound was prepared followed the same procedures described in Example 38. MS: 604.4 $(M+1)^+$.

Example 40

4-Carbamoyl-3'-(6-carbamoyl-4-methyl-4-phenyl-1,2,3,4-tetrahydro-quinolin-2-yl)-biphenyl-2-carboxylic acid This compound was prepared followed the same procedures described in Example 18 using 4-aminobenzamide instead of 4-aminobenzamidine. MS: 506.4 $(M+1)^+$.

Example 41

4-Carbamoyl-3'-(6-methoxy-4-methyl-4-phenyl-1,2,3,4-tetrahydro-quinolin-2-yl)-biphenyl-2-carboxylic acid This compound was prepared followed the same procedures described in Example 18 using 4-methoxyaniline instead of 4-aminobenzamidine. MS: 493.4 $(M+1)^+$.

Example 42

(+) 3'-(6-Carbamimidoyl-4-methyl-4-phenyl-1,2,3,4-tetrahydro-quinolin-2-yl)-4-carbamoyl-5'-(3-methyl-butyrylamino)-biphenyl-2-carboxylic acid Part A 2-(4-Aminobphenyl)-5-methyloxadiazole (0.54 g, 1.34 mmol) was suspended in acetonitrile (55 mL). The product from Part C of Example 36 (0.26 g, 1.47 mmol) and x-methylstyrene (0.89 mL, 6.68 mmol) were added, followed by Indium triflate (0.39 g, 0.67 mmol). The mixture was de-gassed and heated at 70° C. under $N_2$ for 1.5 h. The mixture was concentrated, and purified by flash chromatography (ISCO, silica gel 120 g column, 10% EtOAc in hexane to 100 EtOAc gradient) to give 0.75 g of the desired product. MS: 680.3 $(M+1)^+$.

Part B

The nitro compound from Part A (0.57 g) was dissolved in 50 mL of $EtOH/AcOH/H_2O$ mixture (5:0.2:0.8). Iron powder (0.55 g) was added. The mixture was stirred at 80° C. under $N_2$ for 30 minutes. The mixture was diluted with MeOH and filtered through celite. The filtrate was concentrated and re-dissolved in EtOAc. The EtOAc solution was washed with saturated aqueous $NaHCO_3$, $H_2O$, brine, and then dried over $MgSO_4$, concentrated to give 0.50 g of the desired amine. MS: 650.4 $(M+1)^+$.

Part C

The product from Part B (0.20 g, 0.30 mmol) was dissolved in 13 mL of $CH_2Cl_2$. It was cooled at 0° C. and triethylamine (0.42 mL) was added, followed by isovaleryl chloride (0.14 mL). The mixture was stirred at 0° C. under $N_2$ for 0.5 h. Water and $CH_2Cl_2$ were added. The two layers were separated. The $CH_2Cl_2$ layer was washes with water and brine, dried over $MgSO_4$, concentrated. It was purified by flash chromatography (ISCO, silica gel 40 g column, 25% EtOAc in hexane to 100 EtOAc gradient) and the two enantiomers were separated by chiral separation (chiral OD 4.6×250 mm) using heptane and 1:1 MeOH/EtOH mixture (isocratic). The positive enantiomer (retention time=14 minutes) was taken into the next step (65 mg). MS: 734.48 $(M+1)^+$.

Part D

The product from Part C (65 mg) was dissolved in 12 mL of EtOH and HOAc (7:1). It was placed on a hydrogenator under 50 psi with Raney Ni for 20 h. The mixture was filtered through Celite® and concentrated. The resulting solid was dissolved in 10 mL of EtOH and HOAc (7:1). It was placed on a hydrogenator under 40 psi with 10% Pd/C for 2 h. The mixture was filtered through Celite® and concentrated. The crude product was purified by reverse phase HPLC (0.5% TFA in $CH_3CN/H_2O$) to give 39 mg of the desired product as a TFA salt. MS: 604.38 $(M+1)^+$.

Example 43

3'-(6-aminomethyl-4-methyl-4-phenyl-1,2,3,4-tetrahydro-quinolin-2-yl)-4-carbamoyl-5'-(3-methyl-butyrylamino)-biphenyl-2-carboxylic acid Part A 4-Aminobenzolnitril (36 mg, 0.30 mmol) was suspended in acetonitrile (10 mL). The product from Part C of Example 36 (100 mg, 0.25 mmol) and α-methylstyrene (0.15 mL, 1.25 mmol) were added, followed by Indium triflate (71 mg, 0.13 mmol). The mixture was de-gassed and heated at 70° C. under $N_2$ for 3 h. The mixture was concentrated, and purified by flash chromatography (ISCO, silica gel 40 g column, 20% EtOAc in hexane to 100 EtOAc gradient) to give 135 mg of the desired product. MS: 623.38 $(M+1)^+$.

Part B

The nitro compound from Part A (135 mg) was dissolved in 16 mL of $EtOH/AcOH/H_2O$ mixture (20/1/40). Iron powder (75 mg) was added. The mixture was stirred at 80° C. under $N_2$ for 1.5 h. The mixture was diluted with MeOH and filtered through celite. The filtrate was concentrated and re-dissolved in EtOAc. The EtOAc solution was washed with saturated aqueous $NaHCO_3$, $H_2O$, brine, and then dried over $MgSO_4$, concentrated, purified by flash chromatography (ISCO, silica gel 40 g column, 40% EtOAc in hexane to 100 EtOAc gradient) to give 90 mg of the desired amine. MS: 593.4 $(M+1)^+$.

Part C

The product from Part B (90 mg, 0.15 mmol) was dissolved in 10 mL of $CH_2Cl_2$. It was cooled at 0° C. and triethylamine (0.21 mL) was added, followed by isovaleryl chloride (0.09 mL). The mixture was stirred at 0° C. under $N_2$ for 0.5 h. Water and $CH_2Cl_2$ were added. The two layers were separated. The $CH_2Cl_2$ layer was washes with water and brine, dried over $MgSO_4$, concentrated. It was purified by flash chromatography (ISCO, silica gel 40 g column, 40% EtOAc in hexane to 100 EtOAc gradient) to give 70 mg of the desired product. MS: 677.44 (M+1)$^+$.

Part D

The product from Part C (70 mg) was dissolved in 12 mL of MeOH and 4N HCl in dioxane (1.2 mL). Pd/C (10%) was added and the mixture was placed under a balloon filled with $H_2$ for 12 h. The mixture was filtered through Celite® and concentrated. The crude product was purified by reverse phase HPLC (0.5% TFA in $CH_3CN/H_2O$) to give 13 mg of the desired product as a TFA salt. MS: 591.0 (M+1)$^+$.

Examples 44-72 were prepared following the procedures in Example 38.

Tables 1-3 below provide representative examples, the synthesis of which is described above, of the compounds in the present invention.

TABLE 1

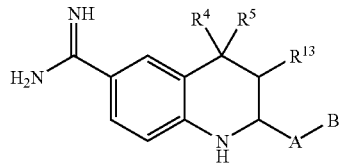

(Ic)

| Ex | $R^4$ | $R^5$ | $R^{13}$ | A | B | MS (M + 1) |
|---|---|---|---|---|---|---|
| 1 | phenyl | H | H | 1,2-phenylene | 2-$CO_2$H-4-CONH(i-Bu)-phenyl | 547.5 |
| 2 | phenyl | H | H | 4-OMe-5-OH-1,2-phenylene | 2-$CO_2$H-4-CONH(i-Bu)-phenyl | 594.5 |
| 3 | 4-OH-phenyl | H | H | 4-OMe-5-OH-1,2-phenylene | 2-$CO_2$H-4-CONH(i-Bu)-phenyl | 610.5 |
| 4 | phenyl | H | H | 1,2-phenylene | 2,4-($CO_2$Me)$_2$-phenyl | 516.4 |
| 5 | phenyl | H | H | 1,2-phenylene | 2,4-($CO_2$H)$_2$-phenyl | 492.3 |
| 6 | phenyl | H | H | 1,2-phenylene | 2-$CO_2$H-phenyl | 448.5 |
| 7 | phenyl | H | H | 1,2-phenylene | 4-$CO_2$H-phenyl | 448.5 |
| 8 | phenyl | Me | H | 1,2-phenylene | 2,4-($CO_2$Me)$_2$-phenyl | 534.3 |
| 9 | phenyl | Me | H | 1,2-phenylene | 2,4-($CO_2$H)$_2$-phenyl | 506.3 |
| 10 | phenyl | H | H | 1,3-phenylene | 2-$CO_2$H-4-CONH(i-Bu)-phenyl | 547.5 |
| 11 | phenyl | H | H | 1,3-phenylene | 2-$CO_2$H-4-CONH(t-Bu)-phenyl | 547.3 |
| 12 | phenyl | H | H | 1,3-phenylene | 2,4-($CO_2$H)$_2$-phenyl | 492.3 |
| 13 | phenyl | H | H | 1,3-phenylene | 2-$CO_2$H-phenyl | 449.4 |
| 14 | phenyl | H | H | 1,3-phenylene | 2-$SO_2NH_2$-phenyl | 483.4 |
| 15 | phenyl | Me | H | 1,3-phenylene | 2-$SO_2NH_2$-phenyl | 497.0 |
| 16 | phenyl | H | H | 1,3-phenylene | 2-$CO_2$H-4-$CO_2$Me-phenyl | 506.4 |
| 17 | phenyl | H | H | 1,3-phenylene | 2,4-($CONH_2$)$_2$-phenyl | 490.4 |
| 18 | phenyl | Me | H | 1,3-phenylene | 2-$CO_2$H-4-$CONH_2$-phenyl | 505.3 |
| 19 | phenyl | H | H | 1,3-phenylene | 2-$CO_2$H-4-$CONH_2$-phenyl | 491.3 |
| 20 | phenyl | Me | H | 1,3-phenylene | 2,4-($CO_2$H)$_2$-phenyl | 506.3 |
| 21 | phenyl | Et | H | 1,3-phenylene | 2,4-($CO_2$H)$_2$-phenyl | 520.3 |
| 22 | phenyl | Pr | H | 1,3-phenylene | 2,4-($CO_2$H)$_2$-phenyl | 534.3 |
| 23 | phenyl | Me | H | 1,3-phenylene | 2-$CO_2$H-4-$NH_2$-phenyl | 477.3 |
| 24 | phenyl | Me | H | 1,3-phenylene | 2-$CO_2$H-4-NHCONHMe-phenyl | 534.4 |
| 25 | phenyl | Me | H | 1,3-phenylene | 2-$CO_2$H-4-$NHSO_2$Me-phenyl | 555.4 |
| 26 | phenyl | Me | H | 1,3-phenylene | 2-$CO_2$H-4-NHCOMe-phenyl | 519.4 |
| 27 | phenyl | Me | H | 1,3-phenylene | 2-$CO_2$H-4-CN-phenyl | 487.5 |

TABLE 1-continued (Ic)

| Ex | R⁴ | R⁵ | R¹³ | A | B | MS (M + 1) |
|---|---|---|---|---|---|---|
| 28 | phenyl | Me | H | 1,3-phenylene | 2-CO₂H-4-CO₂Me-phenyl | 520.4 |
| 29 | phenyl | Me | H | 1,3-phenylene | 2-CO₂H-phenyl | 462.3 |
| 30 | phenyl | Me | H | 1,3-phenylene | 2-CO₂H-4-CONHMe-phenyl | 519.3 |
| 31 | phenyl | Me | H | 1,3-phenylene | 2-CO₂H-4-CONH(i-Pr)-phenyl | 547.4 |
| 32 | phenyl | Me | H | 1,3-phenylene | 2-CO₂H-4-CONH(t-Bu)-phenyl | 561.3 |
| 33 | 4-F-phenyl | Me | H | 1,3-phenylene | 2-CO₂H-4-CONH₂-phenyl | 523.4 |
| 34 | phenyl | Me | H | 1,3-phenylene | 2-CO₂H-4-CH₂NMe₂-phenyl | 519.4 |
| 35 | phenyl | H | Me | 1,3-phenylene | 2-CO₂H-4-CONH₂-phenyl | 505.3 |
| 36 | phenyl | Me | H | 5-NH₂-1,3-phenylene | 2-CO₂H-4-CONH₂-phenyl | 520.3 |
| 37 | phenyl | H | H | 5-NH₂-1,3-phenylene | 2-CO₂H-phenyl | 463.2 |
| 38 | phenyl | Me | H | 5-NHCOMe-1,3-phenylene | 2-CO₂H-4-CONH₂-phenyl | 562.4 |
| 39 | phenyl | Me | H | 5-NHCO(i-Bu)-1,3-phenylene | 2-CO₂H-4-CONH₂-phenyl | 604.4 |

TABLE 2

(Id)

| Ex | R¹ | R⁴ | R⁵ | R¹¹ | MS (M + 1) |
|---|---|---|---|---|---|
| 40 | —CONH₂ | Phenyl | Me | H | 506.4 |
| 41 | OMe | Phenyl | Me | H | 493.4 |
| 43 | —CH₂NH₂ | Phenyl | Me | 5-NHCO-i-Bu | 591.0 |

TABLE 3

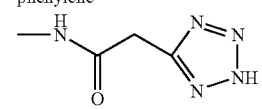

(Ie)

| Ex | A | R[11] | MS (M + 1) |
|---|---|---|---|
| 44 | 5-NHCO(i-Bu)-1,3-phenylene | —CONH$_2$ | 604.38 |
| 45 | 5-NHCO(i-Pr)-1,3-phenylene | —CONH$_2$ | 590.46 |
| 46 | 5-NHCOEt-1,3-phenylene | —CONH$_2$ | 576.26 |
| 47 | 5-NHCO-(cyclopropyl)-1,3-phenylene | —CONH$_2$ | 588.26 |
| 48 | 5-NHCOPr-1,3-phenylene | —CONH$_2$ | 590.28 |
| 49 | 5-NHSO$_2$Et-1,3-phenylene | —CONH$_2$ | 612.23 |
| 50 | 5-NHCONHEt-1,3-phenylene | —CONH$_2$ | 591.27 |
| 51 | 6-OMe-1,3-phenylene | —CONH$_2$ | 535.00 |
| 52 | 6-F-1,3-phenylene | —CONH$_2$ | 522.90 |
| 53 | 5-NHCOCH$_2$CO$_2$H-1,3-phenylene | —CONH$_2$ | 606.20 |
| 54 | 5-NHCOCO$_2$H-1,3-phenylene | —CONH$_2$ | 591.70 |
| 55 | 5-NHCOPh-1,3-phenylene | —CONH$_2$ | 624.26 |
| 56 | 5-NHCOCH$_2$Ph-1,3-phenylene | —CONH$_2$ | 638.28 |
| 57 | 5-NHCO(CH$_2$)$_2$CO$_2$H-1,3-phenylene | —CONH$_2$ | 619.90 |
| 58 | 5-NHCO-(4-CO$_2$H—Ph)-1,3-phenylene | —CONH$_2$ | 667.90 |
| 59 | 5-NHCO-(3-CO$_2$H—Ph)-1,3-phenylene | —CONH$_2$ | 667.60 |
| 60 | 5-NHCO-(2-CO$_2$H—Ph)-1,3-phenylene | —CONH$_2$ | 667.90 |
| 61 | 5-NHCH$_2$CO$_2$H-1,3-phenylene | —CONH$_2$ | 578.00 |
| 62 | 5-NHCO-[3,5-(CO$_2$H)$_2$—Ph]-1,3-phenylene | —CONH$_2$ | 712.20 |
| 63 | 5-NHCO-[3,5-(CF$_3$)$_2$Ph]-1,3-phenylene | —CONH$_2$ | 760.30 |
| 64 | 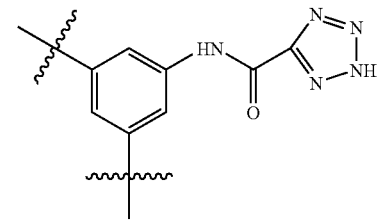 | —CONH$_2$ | 629.80 |
| 65 | 5-NHCO(CH$_2$)$_3$CO$_2$H-1,3-phenylene | —CONH$_2$ | 634.20 |
| 66 | 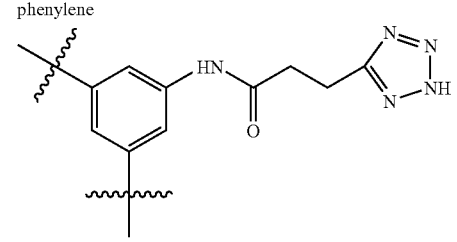 | —CONH$_2$ | 616.24 |
| 67 | 5-NHCO-(3-NH$_2$-5-CO$_2$H—Ph)-1,3-phenylene | —CONH$_2$ | 683.30 |
| 68 | 5-NHCO-(3-Me-5-CO$_2$H—Ph)-1,3-phenylene | —CONH$_2$ | 682.40 |
| 69 | 5-NHCO-(3-(t-Bu)-5-CO$_2$H—Ph)-1,3-phenylene | —CONH$_2$ | 727.40 |
| 70 | 5-NHCO-(3-CONH$_2$-5-CO$_2$H—Ph)-1,3-phenylene | —CONH$_2$ | 711.40 |
| 71 | (3,5-disubstituted phenyl with HN-C(O)-CH$_2$CH$_2$-tetrazole) | —CONH$_2$ | 644.4 |
| 72 | 1,3-phenylene | OMe | 492.1 |

Utility

The compounds of this invention are inhibitors of factor XIa and are useful as anticoagulants for the treatment or prevention of thromboembolic disorders in mammals (i.e., factor XIa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade and/or contact activation system, more specifically, inhibition of the coagulation factors: factor XIa, factor VIIa, factor Ixa, factor Xa, plasma kallikrein or thrombin.

The compounds of this invention also are inhibitors of plasma kallikrein and are useful as anti-inflammatory agents for the treatment or prevention of diseases associated with an activation of the contact activation system (i.e., plasma kallikrein associated disorders). In general, a contact activation system disorder is a disease caused by activation of blood on artificial surfaces, including prosthetic valves or other implants, indwelling catheters, stents, cardiopulmonary bypass, hemodialysis, microorganism (e.g., bacteria, virus), or other procedures in which blood is exposed to an artificial surface that promotes contact activation, blood clots (i.e., diseases involving fibrin formation, platelet activation, and/or platelet aggregation). It also includes systemic inflammatory response syndrome, sepsis, acute respiratory dystress syndrome, hereditary angioedema or other inherited or aquired deficencies of contact activation components or their inhibitors (plasma kallikrein, factor XIIa, high molecular weight kininogen, C1-esterase inhibitor). It may also include acute and chronic inflammations of joints, vessels, or other mammalian organs.

The effectiveness of compounds of the present invention as inhibitors of the coagulation factors XIa, VIIa, IXa, Xa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin, which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. Compounds tested in the Factor XIa assay are considered to be active if they exhibit a $K_i$ of equal to or less than 15 μM. Preferred compounds of the present invention have $K_i$'s of equal to or less than 1 μM. More preferred compounds of the present invention have $K_i$'s of equal to or less than 0.1 μM. Even more preferred compounds of the present invention have $K_i$'s of equal to or less than 0.01 μM. Compounds of the present invention have demonstrated $K_i$ values of equal to or less than 15 μM in the assay for Factor XIa, thereby confirming the utility of the compounds of the present invention as effective inhibitors of coagulation Factor XIa.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. Compounds tested in the Factor VIIa assay are considered to be active if they exhibit a $K_i$ of equal to or less than 15 μM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCDCA2100-B (CenterChem) or Pefafluor IXa 3688 (H-D-Leu-Ph'Gly-Arg-AMC; CenterChem) at a concentration of 0.0004-0.0005 M. Compounds tested in the Factor IXa assay are considered to be active if they exhibit a $K_i$ of equal to or less than 15 μM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.0003 M. Compounds tested in the Factor Xa assay are considered to be active if they exhibit a $K_i$ of equal to or less than 15 μM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M.

Compounds tested in the plasma kallikrein assay are considered to be active if they exhibit a $K_i$ of equal to or less than 15 µM. Preferred compounds of the present invention have $K_i$'s of equal to or less than 1 µM. More preferred compounds of the present invention have $K_i$'s of equal to or less than 0.1 µM. Even more preferred compounds of the present invention have $K_i$'s of equal to or less than 0.01 µM. Compounds of the present invention have demonstrated $K_i$ values of equal to or less than 15 µM in the assay for plasma kallikrein, thereby confirming the utility of the compounds of the present invention as effective inhibitors of plasma kallikrein.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. Compounds tested in the thrombin assay are considered to be active if they exhibit a $K_i$ of equal to or less than 15 µM.

Compounds of the present invention have demonstrated $K_i$ values of equal to or less than 15 µM in at least one of the above assays, thereby confirming the utility of the compounds of the present invention as effective inhibitors of the coagulation cascade and/or contact activation system, and useful as anticoagulants for the prevention or treatment of thromboembolic disorders in mammals and/or as anti-inflammatory agents for the prevention or treatment of inflammatory disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o-v_s)/v_s=I/(K_i(1+S/K_m)) \text{ for a competitive inhibitor with one binding site; or}$$

$$v_s/v_o=A+((B-A)/1+((IC_{50}/(I)^n))) \text{ and}$$

$$K_i=IC_{50}/(1+S/K_m) \text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The effectiveness of compounds of the present invention as inhibitors of the coagulation factors XIa, VIIa, IXa, Xa, or thrombin, can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-Venous Shunt Thrombosis Model:

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The anti-inflammatory effect of these compounds can be demonstrated in an Evans Blue dye extravasation assay using C1-esterase inhibitor deficient mice. In this model, mice are dosed with a compound of the present invention, Evans Blue is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The utility of the compounds of the current invention to reduce or prevent the morbidity and/or mortality of sepsis can be assessed by injecting a mammalian host with bacteria or viruses or extracts there of and compounds of the present invention. Typical read-outs of the efficacy include changes in the LD50 and blood pressure preservation.

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, anti-inflammatory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Other anticoagulant agents (or coagulation inhibitory agents) that may be used in combination with the compounds of this invention include warfarin, heparin (either unfractionated heparin or any commercially available low molecular weight heparin, for example LOVENOX™), aprotinin, synthetic pentasaccharide, direct acting thrombin inhibitors including hirudin and argatroban, as well as other factor VIIa, VIIIa, IXa, Xa, XIa, thrombin, TAFI, and fibrinogen inhibitors known in the art.

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with P2y12 being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K⁺channel openers such as $I_{Ach}$ inhibitors, and $I_{Kur}$ inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril); angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat, gemopatrilat, nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformnin); glucosidase inhibitors (e.g., acarbose); insulins (including insulin secretagogues or insulin sensitizers); meglitini des (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic and/or inflammatory disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or admin-

What is claimed is:

1. A compound of Formula (Ib):

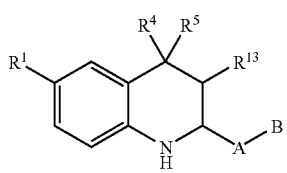

(Ib)

or a stereoisomer or a pharmaceutically acceptable salt thereof, wherein:

A is 5-NHCO(tetrazol-5-yl)-1,3-phenylene, 5-NHCOCH$_2$(tetrazol-5-yl)-1,3-phenylene, or 5-NHCO(CH$_2$)$_2$(tetrazol-5-yl)-1,3-phenylene;

B is phenyl substituted with 0-2 R$^{11}$ and 0-1 R$^{12}$;

R$^1$ is H, F, Cl, —C(=NH)NH$_2$, —CH$_2$NH$_2$, —C(O)NR$^{7a}$R$^8$, OMe, or CN;

R$^4$ is phenyl substituted with 0-3 R$^{4b}$;

each R$^{4b}$ is, independently at each occurrence, H, OH, Cl, F, Cl, Br, CN, NO$_2$, CF$_3$, C(O)OR$^a$, SO$_2$R$^c$, —NR$^7$R$^8$, C$_1$-C$_4$ alkyl, C$_2$-C$_4$ alkenyl, C$_2$-C$_4$ alkynyl, C$_3$-C$_6$ cycloalkyl, C$_1$-C$_4$ haloalkyl, C$_1$-C$_4$ haloalkyloxy-, C$_1$-C$_4$ alkyloxy-, C$_1$-C$_4$ alkylthio-, C$_1$-C$_4$ alkyl-C(O)—, or C$_1$-C$_4$ alkyl-C(O)NH—;

R$^5$ is H or C$_1$-C$_3$ alkyl;

each R$^7$ is, independently at each occurrence, H, C$_{1-6}$ alkyl, or benzyl;

each R$^{7a}$ is, independently at each occurrence, H, C$_{1-4}$ alkyl substituted with 0-1 R$^{7b}$ or 0-1 R$^{7c}$, —(CH$_2$)$_r$—C$_{3-7}$ cycloalkyl substituted with 0-1 R$^f$, or —(CH$_2$)$_r$-phenyl substituted with 0-2 R$^f$;

R$^{7b}$ is OR$^g$, F, CN, —NR$^7$R$^8$, —C(O)R$^g$, —C(O)OR$^g$, —NR$^8$C(O)R$^g$, —C(O)NR$^8$R$^9$, —SO$_2$NR$^8$R$^9$, or —NR$^8$SO$_2$—C$_{1-4}$ alkyl;

R$^{7c}$ is C$_{3-7}$ cycloalkyl substituted with 0-1 R$^f$, phenyl substituted with 0-2 R$^f$, or a 5-6 membered heterocycle consisting of: carbon atoms and 1-4 heteroatoms selected from the group consisting of N, O, and S(O)$_p$, and substituted 0-2 R$^f$;

R$^{7d}$ is —(CH$_2$)$_r$-5-6 membered heterocycle consisting of: carbon atoms and 1-4 heteroatoms selected from the group consisting of N, O, and S(O)$_p$, and substituted 0-2 R$^f$;

each R$^8$ is, independently at each occurrence, H, C$_{1-6}$ alkyl, or benzyl;

each R$^9$ is, independently at each occurrence, H, C$_{1-6}$ alkyl, or benzyl;

each R$^{11}$ is, independently at each occurrence, H, F, —(CH$_2$)$_r$—OR$^a$, CN, —(CH$_2$)$_r$—NR$^7$R$^8$, C(O)OR$^a$, NR$^8$C(O)R$^a$, NR$^8$C(O)OR$^a$, C(O)NR$^{7a}$R$^8$, —NR$^8$C(O)NR$^8$R$^9$, —SO$_2$NR$^8$R$^9$, or —NR$^8$SO$_2$—C$_{1-4}$ alkyl;

R$^{12}$ is C(O)NR$^{7a}$R$^8$, —(CH$_2$)$_r$CO$_2$R$^{12a}$, SO$_2$NHR$^{12a}$, —CONHSO$_2$NHR$^{12a}$, —SO$_2$NHCOR$^{12a}$, —SO$_2$NHCO$_2$R$^{12a}$, —CONHSO$_2$R$^{12b}$, NHSO$_2$R$^{12b}$, CONHSO$_2$R$^{12b}$, —CONHOR$^{12b}$, or —(CH$_2$)$_r$-5-tetrazolyl-;

each R$^{12a}$ is, independently at each occurrence, H or C$_{1-6}$ alkyl;

each R$^{12b}$ is, independently at each occurrence, C$_1$-C$_4$ alkyl substituted with 0-1 R$^{12c}$, C$_2$-C$_4$ alkenyl substituted with 0-1 R$^{12c}$, C$_2$-C$_4$ alkynyl substituted with 0-1 R$^{12c}$, —(CH$_2$)$_r$—C$_3$-C$_7$ carbocycle substituted with 0-2 R$^{12c}$, or —(CH$_2$)$_r$-5-6 membered heterocycle consisting of: carbon atoms and 1-4 heteroatoms selected from the group consisting of N, O, and S(O)$_p$, and substituted with 0-2 R$^{12c}$;

each R$^{12c}$ is, independently at each occurrence, H, F, Cl, Br, I, CF$_3$, OCF$_3$, CN, NO$_2$, OR$^a$, —CO$_2$R$^a$, —NR$^7$R$^8$, SO$_2$R$^c$, C$_1$-C$_6$ alkyl, C$_2$-C$_6$ alkenyl, C$_2$-C$_6$ alkynyl, —(CH$_2$)$_r$—C$_{3-10}$ carbocycle substituted with 0-3 R$^d$; or —(CH$_2$)$_r$-5-10 membered heterocycle consisting of carbon atoms and 1-4 heteroatoms selected from the group consisting of N, O, and S(O)$_p$, and substituted with 0-3 R$^d$;

R$^{13}$ is H or C$_1$-C$_4$ alkyl;

each R$^a$ is, independently at each occurrence, H, C$_{1-4}$ alkyl, —(CH$_2$)$_r$—CO$_2$R$^g$, —(CH$_2$)$_r$—C$_{3-7}$ cycloalkyl, or —(CH$_2$)$_r$—C$_{6-10}$ aryl;

each R$^{a1}$ is, independently at each occurrence, a heteroaryl substituted with 0-2 R$^f$ and selected from the group: tetrazolyl, imidazolyl, thiazolyl, thienyl, oxazolyl, isoxazolyl, triazolyl, pyrazolyl, thiadiazolyl, oxadiazolyl, pyridinyl, pyrimidinyl, pyrazinyl, pyridazinyl, and triazinyl;

each R$^f$ is, independently at each occurrence, H, =O, OR$^g$, F, Cl, Br, CF$_3$, CN, NO$_2$, —NR$^8$R$^9$, —C(O)R$^g$, —C(O)OR$^g$, —NR$^8$C(O)R$^g$, —C(O)NR$^8$R$^9$, —SO$_2$NR$^8$R$^9$, —NR$^8$SO$_2$—C$_{1-4}$ alkyl, —NR$^8$SO$_2$CF$_3$, —S(O)$_2$CF$_3$, —S(O)—C$_{1-4}$ alkyl, C$_1$-C$_6$ alkyl, C$_2$-C$_6$ alkenyl, or C$_2$-C$_6$ alkynyl;

each R$^g$ is, independently at each occurrence, H or C$_{1-4}$ alkyl;

p, at each occurrence, is selected from 0, 1, and 2; and r, at each occurrence, is selected from 0, 1, 2, 3, and 4.

2. A compound according to claim 1, wherein:

B is phenyl substituted with 0-2 R$^{11}$ and 0-1 R$^{12}$;

R$^1$ is —C(=NH)NH$_2$, —C(=O)NH$_2$, —CH$_2$NH$_2$, or OMe;

R$^4$ is phenyl substituted with 0-1 R$^{4b}$;

R$^{4b}$ is H, OH, or F;

R$^5$ is H, Me, Et, or Pr;

each R$^{11}$ is, independently at each occurrence, H, F, OH, OMe, CN, —NH$_2$, —CH$_2$OH, —CO$_2$H, —CO$_2$Me, —NHCOMe, —NHCOEt, —NHCOPr, —NHCO(i-Pr), —NHCO(i-Bu), —NHCO(cyclopropyl), —NHCO(phenyl), —NHCO(2-CO$_2$H-phenyl), —NHCO(3-CO$_2$H-phenyl), —NHCO(4-CO$_2$H-phenyl), —NHCO(3,5-(CO$_2$H)$_2$-phenyl)-, —NHCO(3,5-(CF$_3$)$_2$-phenyl), —NHCO(3-Me-5-CO$_2$H-phenyl), —NHCO(3-(t-Bu)-5-CO$_2$H-phenyl), —NHCO(3-CONH$_2$-5-CO$_2$H-phenyl), —NHCO(3-NH$_2$-5-CO$_2$H-phenyl), —NHCO(benzyl), —NHCO(phenethyl), —NHCO(phenylpropyl), —NHCO [2-(2-pyridyl)-ethyl], —NHCO(tetrazol-5-yl), —NHCOCH$_2$(tetrazol-5-yl), —NHCO(CH$_2$)$_2$(tetrazol-5-yl), —CONH$_2$, —CONHMe, —CONH(i-Pr), —CONH(i-Bu), —CONH(t-Bu), —CONH(benzyl), —CONH(phenethyl), —CONH(phenylpropyl), —CONH[2-(2-pyridyl)-ethyl], —NHCONHMe, —NHCONHLt, —NHCH$_2$CO$_2$H, —NHCOCO$_2$H, —NHCOCH$_2$CO$_2$H, —NHCO(CH$_2$)$_2$CO$_2$H, —NHCO(CH$_2$)$_3$CO$_2$H, —NHSO$_2$Me, —NHSO$_2$Et, or —CH$_2$NMe$_2$;

R$^{12}$ is —CO$_2$H, —CH$_2$(CO$_2$H), —CO$_2$Me, —SO$_2$NH$_2$, or —CONH$_2$; and R$^{13}$ is H or Me.

3. A compound according to claim 2, wherein:

A is 5-NHCO(tetrazol-5-yl)-1,3-phenylene, 5-NHCOCH$_2$(tetrazol-5-yl)-1,3-phenylene, or 5-NHCO(CH$_2$)$_2$(tetrazol-5-yl)-1,3-phenylene;

B is 2-CO$_2$H-phenyl, 4-CO$_2$H-phenyl, 2-SO$_2$NH$_2$-phenyl, 3-CH$_2$(CO$_2$H)-phenyl, 2,4-(CO$_2$H)$_2$-phenyl, 2,4-(CO$_2$Me)$_2$-phenyl, 2,4-(CONH$_2$)$_2$-phenyl, 2-CO$_2$H-4-CO$_2$Me-phenyl, 2-CO$_2$H-4-NH$_2$-phenyl, 2-CO$_2$H-4-CN-phenyl, 2-CO$_2$H-4-OMe-phenyl, 2-CO$_2$H-4-NHAc-phenyl, 2-CO$_2$H-4-CONH$_2$-phenyl, 2-CO$_2$H-4-CONH(i-Pr)-phenyl, 2-CO$_2$H-4-C(O)NH(i-Bu)-phenyl, 2-CO$_2$H-4-C(O)NH(t-Bu)-phenyl, 2-CO$_2$H-4-NHCOMe-phenyl, 2-CO$_2$H-4-NHCONHMe-phenyl, 2-CO$_2$H-4-CH$_2$NMe$_2$-phenyl, or 2-CO$_2$H-4-NHSO$_2$Me-phenyl;

R$^1$ is —C(=NH)NH$_2$, —C(=O)NH$_2$, —CH$_2$NH$_2$, or OMe;

R$^4$ is phenyl, 4-OH-phenyl or 4-F-phenyl;

R$^5$ is H, Me, Et, or Pr; and

R$^{13}$ is H or Me.

4. A compound of claim 1 selected from:

3'-(6-carbamimidoyl-4-methyl-4-phenyl-1,2,3,4-tetrahydro-quinolin-2-yl)-4-carbamoyl-5'-[(5-tetrazolyl)methylcarbonylamino]-biphenyl-2-carboxylic acid;

3'-(6-carbamimidoyl-4-methyl-4-phenyl-1,2,3,4-tetrahydro-quinolin-2-yl)-4-carbamoyl-5'-[(5-tetrazoyl)carbonylamino]-biphenyl-2-carboxylic acid; and 3'-(6-carbamimidoyl-4-methyl-4-phenyl-1,2,3,4-tetrahydro-quinolin-2-yl)-4-carbamoyl-5'-[2-(5-tetrazolyl)ethylcarbonylamino]-biphenyl-2-carboxylic acid;

or a stereoisomer or a pharmaceutically acceptable salt thereof.

5. A pharmaceutical composition, comprising: a pharmaceutically acceptable carrier and a therapeutically effective amount of a compound of claim 2 or a pharmaceutically acceptable salt thereof.

6. A pharmaceutical composition, comprising: a pharmaceutically acceptable carrier and a therapeutically effective amount of a compound of claim 3 or a pharmaceutically acceptable salt thereof.

7. A pharmaceutical composition, comprising: a pharmaceutically acceptable carrier and a therapeutically effective amount of a compound of claim 4 or a pharmaceutically acceptable salt thereof.

8. A pharmaceutical composition, comprising: a pharmaceutically acceptable carrier and a therapeutically effective amount of a compound of claim 1 or a pharmaceutically acceptable salt thereof.

* * * * *

UNITED STATES PATENT AND TRADEMARK OFFICE
CERTIFICATE OF CORRECTION

PATENT NO. : 7,709,646 B2
APPLICATION NO. : 11/430588
DATED : May 4, 2010
INVENTOR(S) : Mimi L. Quan et al.

It is certified that error appears in the above-identified patent and that said Letters Patent is hereby corrected as shown below:

Column 74

Line 29, "—S(O)—$C_{1-4}$ alkyl," should read -- —S(O)$_p$—$C_{1-4}$ alkyl, --; and
Line 60, "—NHCONHLt," should read -- —NHCONHEt, --.

Signed and Sealed this

Twenty-first Day of September, 2010

David J. Kappos
*Director of the United States Patent and Trademark Office*